(12) United States Patent
Singer et al.

(10) Patent No.: US 10,794,859 B2
(45) Date of Patent: Oct. 6, 2020

(54) ELECTROPHORESIS ASSISTED METHOD AND DEVICE FOR PURIFYING A CHARGED TARGET MOLECULE FROM A SAMPLE

(71) Applicant: QIAGEN GMBH, Hilden (DE)

(72) Inventors: Thorsten Singer, Hilden (DE); Sarah Fakih, Hilden (DE); Sabine Kuchler, Hilden (DE); Corinna Küppers, Hilden (DE); Lother Breitkopf, Hilden (DE); Maximilian Focke, Hilden (DE); Nicole Seip, Hilden (DE)

(73) Assignee: Qiagen GmbH, Hidlen (DE)

( * ) Notice: Subject to any disclaimer, the term of this patent is extended or adjusted under 35 U.S.C. 154(b) by 280 days.

(21) Appl. No.: 15/576,310

(22) PCT Filed: Jun. 1, 2016

(86) PCT No.: PCT/EP2016/062328
§ 371 (c)(1),
(2) Date: Nov. 22, 2017

(87) PCT Pub. No.: WO2016/193281
PCT Pub. Date: Dec. 8, 2016

(65) Prior Publication Data
US 2018/0202968 A1 Jul. 19, 2018

(30) Foreign Application Priority Data

Jun. 1, 2015 (EP) .................................... 15170148
Jun. 1, 2015 (EP) .................................... 15170159

(51) Int. Cl.
*G01N 27/447* (2006.01)
*C12N 15/10* (2006.01)

(52) U.S. Cl.
CPC ..... *G01N 27/44739* (2013.01); *C12N 15/101* (2013.01); *G01N 27/44747* (2013.01)

(58) Field of Classification Search
CPC .................. G01N 27/44739; G01N 27/44704
See application file for complete search history.

(56) References Cited

U.S. PATENT DOCUMENTS

| | | | |
|---|---|---|---|
| 4,608,147 A * | 8/1986 | Clad ...................... | B01D 57/02 204/613 |
| 5,340,449 A | 8/1994 | Shukla | |

(Continued)

FOREIGN PATENT DOCUMENTS

| | | | |
|---|---|---|---|
| JP | 63-222254 A * | 9/1988 | ............. G01N 27/26 |
| JP | 2009036719 A | 2/2009 | |

(Continued)

OTHER PUBLICATIONS

Full English language translation of Koichi Yoshinaga JP 63-222254 A, patent published Sep. 16, 1988 (Year: 1988).*

(Continued)

*Primary Examiner* — Alexander S Noguerola
(74) *Attorney, Agent, or Firm* — McBee Moore & Vanik IP, LLC

(57) ABSTRACT

The invention inter alia pertains to an electrophoresis assisted method for purifying at least one charged target molecule, preferably a nucleic acid, from a sample. Moreover, a device for use in a method for purifying a charged target molecule by electrophoresis is provided.

12 Claims, 19 Drawing Sheets

(56) References Cited

U.S. PATENT DOCUMENTS

| | | |
|---|---|---|
| 6,129,828 A | 10/2000 | Sheldon, III et al. |
| 2010/0326827 A1 | 12/2010 | Lin et al. |
| 2011/0011742 A1* | 1/2011 | Mathers ............... C07K 1/26 204/462 |
| 2013/0020201 A1 | 1/2013 | Yotoriyama et al. |

FOREIGN PATENT DOCUMENTS

| | | |
|---|---|---|
| WO | 0178876 A1 | 10/2001 |
| WO | 0224314 A1 | 3/2002 |
| WO | 2005/040782 A1 | 5/2005 |

OTHER PUBLICATIONS

Monaghan et al., "A Comparison of the Electrophoretic Velocities of Cellophane and Colloidion Suspensions with Electroosmotic Velocities through Membranes of the same Material," The Journal of General Physiology, Mar. 20, 1935, pp. 523-530 (Year: 1935).*
PCT International Search Report for PCT/EP2016/062328, dated Jul. 15, 2016.

* cited by examiner

Cathode

Anode

Cathode

Anode

30kD membrane    50kD membrane

ELECTROPHORESIS ASSISTED METHOD AND DEVICE FOR PURIFYING A CHARGED TARGET MOLECULE FROM A SAMPLE

CROSS-REFERENCE TO RELATED APPLICATIONS

This application is a National Stage entry of International Application No. PCT/EP2016/062328, filed Jun. 1, 2016, which claims priority to European Patent Application No. 15170148.9, filed Jun. 1, 2015 and European Patent Application No. 15170159.6, filed Jun. 1, 2015.

BACKGROUND

Field of Invention

The invention pertains inter alia to a method for purifying a charged target molecule, such as a nucleic acid, which involves electrophoresis and to a device that can be used for purifying a charged target molecule by electrophoresis.

Description of Related Art

The isolation of charged target molecules, in particular negatively charged target molecules such as nucleic acids is of great interest. State of the art nucleic acid isolation methods are mainly based on solid phase extraction. Nucleic acids are, were necessary, released from the sample and bound under appropriate binding conditions to a solid phase. Different principles are commonly used such as binding the nucleic acids to an anion exchange surface or binding the nucleic acids in the presence of salt and/or a water-miscible organic solvent (such as an alcohol) to a solid phase, such as in particular a silica solid phase. Methods that use a chaotropic salt in order to bind nucleic acids to a silica solid phase (e.g. a membrane or magnetic silica particles) are widely used and many commercial kits are based on this principle. These known protocols require a number of hands-on interactions after the nucleic acids were bound to the solid phase. These interactions include performing one or more washing steps and eluting the nucleic acids. The individual steps require e.g. the assembly/disassembly of spin columns and collection tubes or the resuspension/collection of magnetic beads. Especially when processing a larger number of samples successively or in parallel, these known protocols are time-consuming and cumbersome. Automated protocols require complex and expensive instrumentation with a large number of moving parts making these machines prone to mechanical disturbances.

Electric field based methods (e.g. electrophoresis, electroelution, etc.) are well known and widely used in biological labs. Agarose- and polyacrylamide electrophoresis are textbook methods. However, both methods, including their modifications and specific variations, are primarily used for analytical purposes. Preparative gel electrophoresis typically requires an additional step to recover the target molecule from the gel matrix which in turn requires more or less an additional nucleic acid isolation procedure. Preparative electrophoresis is applicable for low concentrations of target molecules due to the separation capacity of the gel matrix. For example, overloading an agarose gel results in broadened and smeared bands, leading to the co-isolation of unwanted sample components and thus contaminated products.

Preparative systems were developed which use electrophoresis in a more or less complicated set-up for the isolation of nucleic acids such as DNA. Such system is described in U.S. Pat. No. 8,568,580 and describes a non-linear 2D electrophoresis to concentrate DNA in the centre of a matrix from where it can be collected. The limitations of this system are inter alia its instrument price and long processing times (~4 hours). Another system is disclosed in U.S. Pat. No. 5,217,593 which was originally designed for plasmid isolation directly from E. coli culture. An electrophoresis based instrument is also known from U.S. Pat. No. 5,340,449 which discloses a relatively open system consisting of a large electrophoresis chamber in which a sample device is mounted. The sample device is a modular piece where "link chambers", caps and membranes can be assembled in different combinations, depending on the desired applications.

WO 00/71999 describes a method for isolating nucleic acids which includes an electric field based separation step. The method uses a device, which comprises a cathode chamber and an anode chamber. In-between, an intermediate assembly is present through which the nucleic acids pass on their way to the anode. A stabilized gel, such as an agarose gel or a fiber can be used as intermediate assembly. In WO 00/71999 A1 an intermediate assembly is placed in a passage between two membranes, each of the membranes closing an electrode chamber. This document discusses the problems and challenges that occur when undesired flows occur in the device which can result in that chambers run empty, thereby disrupting the electric field. In WO 00/71999 A1 it is taught that the design of the intermediate assembly is responsible for controlling the electroosmotic flow inside a passage of a cartridge and should be adequately designed to achieve the type of electroosmotic flow desired in WO 00/71999 A1. WO 00/71999 teaches that this intermediate assembly shall in particular reduce the electroosmotic flow to a minimum and therefore, provides a barrier against the electroosmotic flow. The intermediate assembly functions as a semipermeable membrane and therefore allows the use of different buffers in the anode and cathode chamber.

U.S. Pat. No. 6,264,814 describes an apparatus and method for isolating nucleic acids which is based on the principle of electroelution. The nucleic acids are eluted using an electric field from different solid phases. The nucleic acids can migrate through a gel to the anode which can be shielded from the nucleic acids by a semipermeable membrane. WO 98/10277 discloses an electric field based nucleic acid isolation method. The nucleic acids migrate from the sample chamber to the anode, thereby passing a spacer region which provides a trap having a differential effect on desired materials. WO 97/34908 teaches a nucleic acid separation method which is based on electroelution. In the described apparatus, the anode and cathode can be shielded by membranes.

One object of the present invention is to provide an electrophoresis based method for purifying a target nucleic acid. A further object is to provide a method that is suitable to purify a target nucleic acid on a larger preparative scale from a wide variety of samples which reduces handling steps. Moreover, it is one object to provide a device for use in a method for purifying a target nucleic acid by electrophoresis that avoids prior art drawbacks. In particular, it is an object to provide a cost-efficient device that is simple in its design but allows an efficient purification of a target nucleic acid.

SUMMARY OF THE INVENTION

According to a first aspect, the present invention provides an electrophoresis assisted method for purifying a charged target molecule, comprising placing the target molecule to be purified into the passage of a device, wherein said passage is closed at one end by a liquid permeable collection matrix;

generating an electric field between a cathode and an anode in a running solution that conducts the electric current to impose a force onto the target molecule comprised in the passage, wherein the collection matrix forms a barrier for the target molecule;

collecting the purified target molecule.

The charged target molecule can be a negatively charged molecule and preferably is a nucleic acid.

According to a second aspect, a device suitable to be placed in an electrophoresis chamber for use in a method for purifying a charged target molecule, preferably a nucleic acid, by electrophoresis is provided, the device comprising a first end region and a second end region and a passage between the first end region and the second end region wherein the passage is closed at the second end region by a liquid permeable collection matrix. The device is placed for electrophoresis in an electrophoresis chamber. According to the preferred embodiment, the device is a cartridge and more preferably, does not comprise electrodes for generating the electric field.

In a third aspect, the present invention pertains to the use of the device according to the second aspect for purifying a charged target molecule, preferably a nucleic acid, using electrophoresis, wherein the device is placed in an electrophoresis chamber for electrophoresis and wherein the electrophoresis chamber comprises the electrodes for generating the electric field.

In a fourth aspect, an assembly set for a device for use in a method for separating a charged target molecule, preferably a nucleic acid, by electrophoresis is provided, wherein the assembly set comprises at least two containers, each of the at least two containers having at least two openings, wherein the at least two containers are connectable to form a passage, one of the containers comprising a liquid-permeable separation matrix and/or a liquid-permeable collection matrix and the other container comprising a liquid permeable closing matrix.

In a fifth aspect, a method for purifying a charged target molecule, preferably a nucleic acid, by electrophoresis is provided, comprising the step of inserting a device according to the second aspect or a device assembled from the assembly set according to the fourth aspect into an electrophoresis chamber which is prefilled or adapted to be filled with a running solution and which comprises electrodes for generating an electric field.

In a sixth aspect, a system is provided comprising the device according to the second aspect or an assembly set for a device according to the fourth aspect and an electrophoresis chamber which comprises electrodes for generating the electric field.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF A PREFERRED EMBODIMENT

Figure 1:
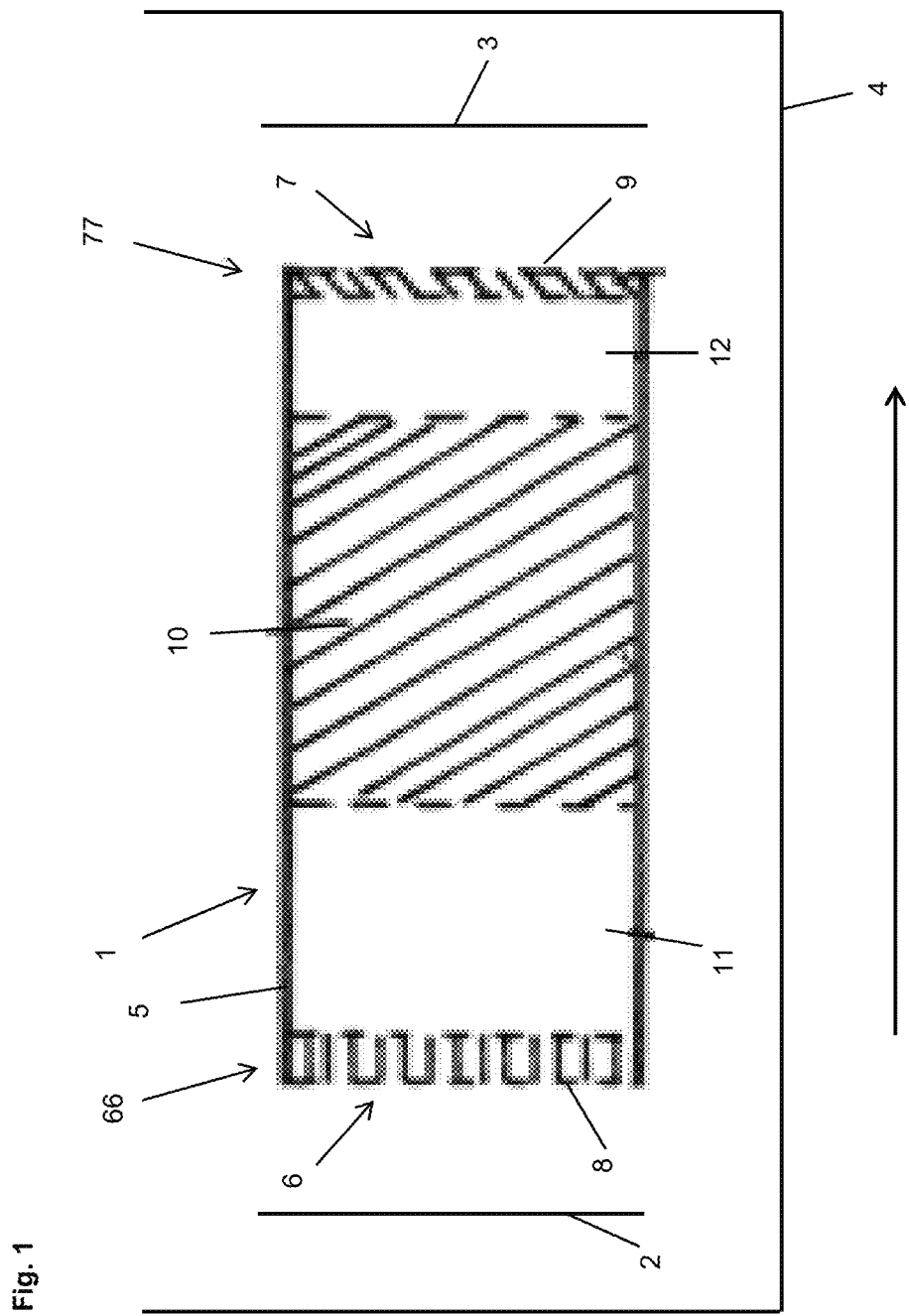
FIGS. 1-32 depict embodiments as described herein.

The present invention pertains inter alia to methods and devices for performing an electrophoresis assisted method for purifying a charged target molecule, such as a target nucleic acid. The used device comprises a passage into which the charged target molecule to be purified is placed for purification. A running solution can enter and exit the passage, thereby allowing to generate an electric field between a cathode and an anode that imposes a force onto the charged target molecule comprised in the passage. This force can induce e.g. the migration of the target molecule in the passage towards the anode or cathode, depending on the charge of the target molecule. A negatively charged target molecule, such as a nucleic acid, will migrate to the anode. A positively charged target molecule, e.g. a protein, will migrate to the cathode. The passage of the device is closed at one end by a liquid permeable collection matrix. In case a negatively charged target molecule such as a nucleic acid is purified, the collection matrix is oriented in use towards the anode. In case a positively charged target molecule is purified, the collection matrix is oriented in use towards the cathode. The collection matrix forms a barrier for the target molecule and prevents e.g. that the target molecule contacts the electrode during purification.

The inventors have surprisingly found that the collection matrix has a significant influence on the fluid flow in the passage during electrophoresis. Thus, besides having a mere shielding function to prevent a contact between the target molecule and the electrode, it can act like a "pump" that has a significant influence on the running solution that is comprised in the passage. The inventors have found that the collection matrix can induce a flow, which is believed to be an electroosmotic flow. This can create as is demonstrated by the examples a flow within the passage of the device that is e.g. directed towards the cathode and thus provides a force that opposes the direction of the force created on a negatively charged target molecule by the electric field. In case a positively charged target molecule is purified, the flow would support in a corresponding set-up the migration of the target molecule to the cathode. This flow inducing effect was seen with various types of collection matrixes, including ultrafiltration membranes what was highly surprising. Because of this unexpected significant influence of the collection matrix on the flow properties in the passage of the device, the design process of the device should consider and e.g. start with the choice of the collection matrix. The inventors found that the strength of this flow that is induced by the collection matrix can be adjusted and/or compensated and hence can be controlled according to the desired needs by various parameters described herein, such as in particular the choice of the pore size of the collection matrix and/or the collection matrix material and furthermore, the applied electric field, in particular the field strength. These parameters can be used to ensure that the device behaves in a desired way when conducting the electrophoresis assisted method. As will be shown further below, the possible existence of further matrixes in the passage of the device, such as a liquid permeable closing matrix and/or a liquid permeable separation matrix, additionally contributes to and hence can be used to adjust and control the flow-behaviour in the passage in the desired way. The method is advantageous and allows separating a target molecule according to its charge and/or charge density depending on the flow characteristics that are established in the passage. In addition, by adjusting and controlling the flow behaviour within the passage it can be prevented that e.g. a loading chamber or a collection chamber provided in the passage runs empty or overflows with running solution during the electric field based purification which would be detrimental to the purification process, as the electric field can break down or target molecules can get lost.

As is demonstrated by the examples, according to one sub-aspect, the collection matrix causes a flow in the running solution comprised in the passage that is directed in the opposite direction than the target molecule is directed to by the electric field. E.g. in case a negatively charged target molecule such as a nucleic acid is purified, the collection matrix is orientated at the anode and said induced flow goes towards the cathode. The strength of the flow in the passage, which is believed to be the result of an electroosmotic flow induced by the collection matrix, can be adjusted using the parameters described herein. The charged target molecule is retained in the passage by the applied electric field due to its charge and also charge density. The force acting on the charged target molecule due to the electric field is larger than the force acting on the target molecule due to the induced flow in the running solution that moves into the opposite direction than the target molecule migrates in the electric field. The electro-kinetic force exerted by the applied electric field is substantially strong enough
- to hold the charged target molecule in place,
- to at least slow down sufficiently the movement of the charged target molecule into the opposite direction (e.g. towards the cathode in case a negatively charged target molecule is purified) so that it is not flushed out of the passage in the time that the electric field is being applied or
- preferably, to induce migration of the charged target molecule towards the collection matrix where the target molecule is retained.

E.g. a negatively charged target molecule is thereby retained in place in the passage or preferably migrates due to the applied electric field towards the anode where it is then retained at the collection matrix. This prevents an unwanted loss of target molecule, even though a flow into the direction of the cathode occurs. Furthermore, it is to be noted that the flow that is created in the passage, if adjusted appropriately, is advantageous as is demonstrated by the examples. This flow that moves into the direction of the cathode is capable of removing impurities from the negatively charged target molecule, e.g. by flushing out at least some unwanted further elements such as impurities out of the passage at the side oriented towards the cathode. As is shown by the examples, even negatively charged molecules having a lower charge density than the negatively charged target molecule can be separated thereby from the target molecule. The method therefore also allows to separate molecules according to their charge density in the same run. In addition to the separation of the negatively charged target molecule, such as a nucleic acid, from positively charged or neutral contaminations in the electric field, molecules with a charge density smaller than the negatively charged target molecule are flushed through the rear even if they were in total negatively charged. This may improve the purity what is advantageous, in particular when being confronted with challenging samples from which e.g. a negatively charged target molecule shall be purified as it is often the case with biomolecules, such as in particular nucleic acids. Smaller molecules with a negative charge density identical or even larger than the target molecule are removed e.g. by passing the collection membrane.

This sub-aspect of the invention can be considered to be and is also described herein as the "flow-assisted" sub-aspect, where the choice of the collection matrix and optionally other parameters as described herein is made to create a flow within the passage that is sufficiently strong to have a desired effect on the unwanted elements in the passage, such as impurities. The role of the electric field with regard to the target molecule is in particular to avoid that the target molecule gets lost because of this flow and preferably, to induce migration of the charged target molecule towards the collection matrix.

As is demonstrated by the examples, according to a further sub-aspect, the used collection matrix is also capable of causing a flow, which is as described believed to be an electroosmotic flow, that is directed in the opposite direction than the target molecule is directed to by the electric field. E.g. in case a negatively charged target molecule such as a nucleic acid is purified, the collection matrix is orientated at the anode and said induced flow would go towards the cathode. However, in this sub-aspect, a substantial flow within the passage of the device that is directed to the opposite direction (e.g. towards the cathode in case a negatively charged target molecule is purified) is substantially prevented by the design of the device and/or the applied electric field strength. Thus, in this sub-aspect, a flow that is induced and hence caused by the collection matrix is compensated within the passage, thereby allowing an electro-kinetic separation according to the charge of the target molecule that is substantially undisturbed by any flow effects that go into the opposite direction. Such flow effects within the passage of the device are according this sub-aspect preferably minimized and hence substantially eliminated as force that acts on the charged target molecule and optionally other equally charged molecules. Suitable parameters to achieve such flow compensation within the passage are described herein. This aspect of the invention can be considered to be the "electro-kinetic" aspect, where the choice of the collection matrix, other device elements (such as e.g. the presence of a closing matrix) and/or the electric field strength is made to adjust that flows, in particular visible flows, within the passage are sufficiently reduced and preferably are minimized inside the passage to not disturb the electro-kinetic driven migration of the charged target molecule and optionally other equally charged molecules towards the collection matrix.

Combinations of the two sub-aspects of the invention are also feasible, depending e.g. on the target molecule, such as e.g. its charge, charge density and/or the composition and complexity of the target molecule containing sample, and these sub-aspects may also overlap depending on the strength of the flow that is induced by the collection matrix. According to one embodiment, a flow is created in the passage that is sufficiently strong to have an desired effect on unwanted elements that are equally charged as the target molecule while at the same time the electric field is sufficiently strong to effect the movement of charged target molecule into the direction of the collection matrix and thus against the induced flow.

The technology of the present invention can be used to purify a charged target molecule, such as in particular a biomolecule. The target molecule can be negatively or positively charged and preferably is negatively charged. A key application field of the present method is the purification of a target nucleic acid. As is evident from the examples, the present technology allows the purification of different types of target nucleic acids such as DNA and/or RNA from various sample sources. The purification is fast, simple and requires only few handling steps. It can be combined with established chemistries for processing the samples such as e.g. an existing and proven lysis and/or binding chemistry, e.g. involving a chaotropic salt. A major advantage compared to common isolation protocols is the possible omission of extra pipetting and handling steps like the addition of washing and elution buffers or waste removal after the target nucleic acid was bound to the solid phase in embodiments, the lysate can be directly processed in the device. Manual interactions can be significantly reduced. In case of automation the workflow of the invention requires significantly less movable parts thereby significantly reducing cost of goods in production, reducing maintenance cost, and elongating maintenance intervals due to the minimized mechanical stress. The purified target molecule that is retained at the collection matrix can be easily removed from the device using e.g. a pipette. In case multiple samples are processed in parallel, the processing time increases less in relation to the sample number as it does e.g. in case of common spin column based protocols because time consuming liquid and transfer steps are reduced with the present technology. When the target molecule is loaded into the passage of the device and subjected to the electric field, processing time may be fixed regardless of the amount of the amount of target molecule or the original size and volume of the sample which is especially useful for large volume liquid samples. This is convenient and reduces handling errors.

In the present description, design elements of the device will be explained that is used e.g. in the method according to the first aspect, is provided by the second aspect of the present invention and also forms part of other aspects of the present invention. The description of any design elements of the device, including e.g. suitable and preferred combinations of the collection matrix with a closing matrix and/or a separation matrix, apply to the device that is used in the method according to the first aspect as well as to the device that is provided by the second or other aspects of the invention. A key field of use for the device will be in a method for purifying a charged target molecule, such as a target nucleic acid, by electrophoresis. The advantages obtained with one or the other feature of the device might be explained with reference to the possible use of the device in such a method without limiting the use of the device to such a method.

Subsequently, the invention will be explained predominantly referring to the preferred embodiment, wherein a negatively charged target molecule, in particular a nucleic acid, is purified. This disclosure applies however mutatis mutandis to the purification of a charged target molecule in general and to the purification of a positively charged target molecule such as a protein. Embodiments described herein by referring to a target molecule, a charged target molecule or a negatively charged target molecule in general, in particular relate to and hence refer to the purification of a target nucleic acid as preferred embodiment of the present invention.

Method

According to a first aspect, an electrophoresis assisted method for purifying a charged target molecule is provided, comprising placing the target molecule to be purified into the passage of a device, wherein said passage is closed at one end by a liquid permeable collection matrix;

generating an electric field between a cathode and an anode in a running solution that conducts the electric current to impose a force onto the target molecule comprised in the passage, wherein the collection matrix forms a barrier for the target molecule;

collecting the purified target molecule.

The method according to the first aspect provides an electrophoresis assisted method for purifying at least one charged target molecule from a sample that contains the target molecule. The method allows to separate the target molecule from impurities according to its charge and/or its charge density as is demonstrated by the examples. The target molecule is preferably a biomolecule, more preferably a negatively charged biomolecule such as a nucleic acid. Suitable and preferred characteristics of the device in which the purification of a charged target molecule by electrophoresis occurs are described in the following. It is particularly preferred to use a device according to the second aspect of the invention in the method according to the first aspect.

The passage of the device which receives the charged target molecule to be purified is closed at one end by a liquid permeable matrix, herein referred to as "collection matrix". The passage may comprise e.g. two end openings, wherein one end opening is closed by the collection matrix (also referred to herein as "front end" or "collection end"). The other end opening (also referred to herein as "rear end" or "loading end") may be closed by a closing matrix, as will be explained in further detail below.

The work of the inventors has shown that the collection matrix can act as "a pump" that depending of the arrangement of the electrodes either pumps running solution into the passage or out of the passage. In case the collection matrix is located at the anode, it allows e.g. to control the inflow of fluid arranged outside the passage into the passage. If in the key field of use the device is e.g. placed in an electrophoresis chamber comprising a running solution, the collection matrix can upon application of an electric field be used as a pump. In case the collection matrix is located at the anode and induces a flow into the direction of cathode, it can bring in running solution from outside the device into the passage. In case the collection matrix is located at the cathode, it allows e.g. to control the exit of fluid arranged inside the passage of the device out of the passage.

Without wishing to be bound in theory, it is believed that upon application of an electric field an electroosmotic flow is created in fluid-passages inside the material of the collection matrix. This effect was seen even with ultrafiltration membranes. This electroosmotic flow will lead to a flow of fluid through the collection matrix which will then have an effect on the flow inside the passage of the device. By choosing an appropriate collection matrix and an appropriate electric field, the electroosmotic flow inside the fluid-passages inside the collection matrix can be influenced and hence the amount of fluid being "pumped" by the collection matrix. This allows to control the flow characteristics inside the passage. As is described herein, this effect can also be used to assist the purification of the charged target molecule, in particular a negatively charged target nucleic acid.

In addition, the collection matrix is used to retain the charged target molecule and to prevent that it exits the passage of the device. The collection matrix can allow the passage of liquids and small ions but may retain the target molecule. The collection matrix thus forms a barrier for the target molecule and may hold back physically the target molecule, such as a desired nucleic acid. This is advantageous, because there is no need to monitor the run time in order to avoid loss of target molecule. The purified target molecule is retained by the collection matrix and can be collected and removed from the device. As discussed herein, the purified target molecule is comprised in the running solution. It is preferred that the collection matrix does not bind the target molecule under the conditions that are used for electrophoretic purification. The collection matrix also shields the target molecule from the electrode. In the preferred embodiment described herein, wherein the target molecule is a nucleic acid, it shields the target nucleic acid from the anode, thereby preventing damage to the target nucleic acid.

The collection matrix is hydrophilic to ensure a continuous liquid bridge for charge transportation. The material of the collection matrix can be treated and in particular can be functionalized with suitable groups to ensure hydrophilicity. E.g. hydrophobic materials can be treated with surfactants or can be functionalized with appropriate groups to ensure wettability.

The collection matrix may comprise or consist of a charged, polarizable and/or dielectric material. Preferably, it comprises or consists of a negatively charged, negatively polarizable and/or dielectric material. This embodiment is particularly suitable in case a negatively charged target molecule, such as a nucleic acid, is purified. As described herein, the collection matrix can induce a flow in the running solution comprised in the passage of the device. Said flow may oppose the migration direction of the target molecule along the electric field lines and e.g. flows towards the cathode in case a negatively charged target molecule is purified which migrates in the electric field towards the anode where it is retained by the collection matrix.

The collection matrix is preferably porous. It can be provided by a porous filter or membrane. Also a combination of filters and/or membranes can be used as collection matrix, which may have the same or different characteristics with respect to material, charge, polarity and/or pore size. E.g. a positively charged or a positively polarizable filter or membrane can be used in combination with a negatively charged or negatively polarizable filter or membrane. If placed in close proximity to each other, e.g. directly adjacent to each other and hence apposing, the flow characteristics are modulated by both membranes in combination so that said combination can provide the collection matrix. In case the collection matrix is located at the anode, what is preferred, the negatively charged or negatively polarizable filter or membrane will pump liquid into the passage while the positively charged or a positively polarizable filter or membrane pumps liquid out of the passage. Thereby, the positively charged or positively polarizable filter or membrane can be used to attenuate a strong flow, respectively electroosmotic flow, that is induced by the negatively charged or negatively polarizable filter or membrane. This allows adjusting the flow that is created in the passage by the chosen material of the collection matrix, here a combination of two filters or membranes.

Filters or membranes can have what is perceived to be a "shiny surface" (a surface with a more smooth surface) and a rough surface which is due to the production process. Likewise, with a fleece one can have a side with a more rough and a different side with a smoother surface. In one embodiment, the more smooth surface is arranged facing inwards the passage and the more rough surface is arranged facing outwards.

The collection matrix is preferably an ultrafiltration membrane.

Porous filters and membranes are often characterized by their exclusion limit or "cut-off". The Molecular Weight Cut Off (MWCO) is usually defined in Dalton. It can be defined as the minimum molecular weight of a globular molecule that is retained to 90% by the membrane or filter. The MWCO is chosen such that the target molecule is retained by the collection matrix. According to one embodiment, the collection matrix has a MWCO that lies in the range selected from 1 kDa to 500 kDa, 3 kDa to 300 kDa, 5 kDa to 200 kDa, 5 kDa to 100 kDa and 10 kDa to 50 kDa.

The collection matrix may comprise or consist of a material selected from cellulose materials, such as cellulose, regenerated cellulose (RC), cellulose esters, preferably the cellulose materials are selected from cellulose acetate materials such as cellulose acetate, cellulose diacetate and cellulose triacetate and cellulose nitrate, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide. Preferably, the collection matrix comprises or consists of a material selected from a cellulose material (such as a cellulose material selected from cellulose acetate materials, such as cellulose acetate, cellulose diacetate and cellulose triacetate and cellulose nitrate), PES, nylon and PVDF. More preferably, the collection matrix comprises or consists of PES, regenerated cellulose, or a cellulose acetate material, such as cellulose triacetate. Hydrophobic materials such as e.g. PE and PP can be treated in order to render them hydrophilic. This can be achieved e.g. by functionalization with suitable groups. Respective hydrophobic materials that are rendered hydrophilic are also commercially available.

According to one embodiment, an ultrafiltration membrane is used as collection matrix which has a MWCO in the range of 1 kDa to 300 kDa, 1 kDa to 200 kDa, 3 kDa to 100 kDa or 5 kDa to 50 kDa. For isolating RNA an ultrafiltration membrane is preferably used, having e.g. a MWCO in the range selected from 1 kDa to 50 kDa, 3 kDa to 20 kDa, e.g. 5 kDa to 10 kDa. Preferred materials for such ultrafiltration membrane that is used as collection matrix include, but are not limited to CA, CTA, PES and RC.

As described, the collection matrix may induce a flow in the running solution comprised in the passage that opposes the migration direction of the charged target molecule in the electric field. According to one embodiment, a negatively charged target molecule is purified and the collection matrix is located at the anode and induces a flow in the running solution comprised in the passage that is directed towards the cathode. The target molecule is retained in the passage by the applied electric field due to its negative charge and/or charge density, and preferably migrates to the collection matrix. According to the flow driven sub-aspect of the present method, the induced flow flushes impurities out of the passage, e.g. also negatively charged impurities that have a charge density that is lower than the charged density of the target molecule.

According to one embodiment, the flow within the passage is adjusted and/or compensated by the choice of one or more of parameters selected from the group consisting of the collection matrix material (which includes also combinations of materials), the pore size of the collection matrix material and/or the applied electric field strength. As is demonstrated by the examples, these parameters allow adjusting and thus controlling the flow within the passage.

Additionally, the collection matrix can be used in order to determine which type of target molecule, for example target nucleic acid, with respect to its size or topoisomerism, is retained at the collection matrix as is demonstrated by the examples.

According to one embodiment, more than one collection matrix is arranged in the passage in the order of decreasing pore size towards the collection end of the device to allow recovery of different target molecules, such as different target nucleic acids according to their size and/or configuration in different compartments of the device.

According to one embodiment, the other end of the passage, also referred to as rear end or loading end, is left open. According to a preferred embodiment, the passage of the device is closed at the rear end by a liquid permeable closing matrix. The closing matrix is permeable for the liquids in and outside the device and thus allows e.g. the running solution to enter and exit the device.

The closing matrix assists to prevent that the charged target molecule escapes the passage of the device through the rear end opening, e.g. by confining the target molecule to the passage, e.g. to a loading chamber as will be explained in further detail herein. In case a hollow elongated body with openings at both ends is used as device, the closing matrix can provide a rear closing. The closing matrix can shield the target molecule from the electrode, e.g. the cathode in case a negatively charged target molecule such as a nucleic acid is purified, and may prevent that the target molecule exits the device e.g. before the electric field is applied. As described above, the passage of the device preferably comprises two end openings, wherein one end opening is closed by the collection matrix and the other end opening is closed by the closing matrix. The end openings preferably oppose each other.

Depending on the desired field of use the method can be practiced by either having no separation matrix placed in the passage or by having at least one separation matrix placed in the passage. Preferably, a separation matrix is placed in the passage between the rear end that is closed by the closing matrix and the front end that is closed by the collection matrix. The possible uses and embodiments of such a separation matrix in the passage are described elsewhere of this description.

The closing matrix can be used in conjunction with the collection matrix to control flows within the passage. It can affect the flow inside the passage as is also demonstrated by the examples. The closing matrix can thus be additionally used to adjust and/or compensate and hence control induced flows within the passage of the device in combination with the collection matrix. Thus, according to one embodiment, a flow in the running solution comprised in the passage of the device that is directed to the cathode is adjusted and/or compensated by the choice the closing matrix material and/or the pore size of the closing matrix and additionally one or more parameters selected from the group consisting of the collection matrix material, the pore size of the collection matrix material and/or the applied electric field strength.

The closing matrix can be used e.g. as resistor to reduce the flow of fluid out of the passage through the rear end opening comprising the closing matrix. The closing matrix can thus be used to reduce the flow inside the passage towards the rear end opening. This even if the collection matrix induces an electroosmotic flow as is demonstrated by the examples. This is advantageous in case the flow within the passage is intended to be minimized what is e.g. preferred in certain embodiments described herein, such as the electro-kinetic sub-aspect of the present method.

The closing matrix can also be used to adjust the flow within the passage to a level so that impurities are flushed out of the passage at the rear end opening, while the target molecule is retained inside the passage and preferably migrates towards the collection matrix due to the applied electrical field according to its charge and/or charge density. E.g. a large pore size of the closing matrix may support the flow-assisted sub-aspect of the present method. As is demonstrated by the examples, with the flow-assisted sub-aspect the formation of membrane potentials can be avoided even if the target molecule is introduced in a high salt/high conductivity sample, such as a lysate comprising a chaotropic salt. This allows the direct purification of a charged biomolecule such as a nucleic acid from a lysate.

The closing matrix can be designed as an additional "pump" to supplement and hence assist the flow that is induced by the collection matrix and goes towards the rear end. For this an appropriate matrix is chosen to create what is believed to be an electroosmotic flow in fluid-passages inside the material of the closing matrix upon application of an electric field. This electroosmotic flow will lead to a flow of fluid through the closing matrix out of the passage in case the closing matrix is oriented towards the cathode, which will then have an effect on the flow inside the passage of the cartridge. By choosing an appropriate matrix and an appropriate electric field, what is believed to be an electroosmotic flow inside the fluid-passages inside the closing matrix can be influenced and hence the amount of fluid being "pumped" by the closing matrix. This effect can either be used to pump fluid from outside the cartridge through the opening that is closed by the closing matrix into the passage with a certain choice of closing matrix material and electric field. With a different choice of closing matrix and electric field this effect can be used to pump fluid from inside the passage through the opening comprising the closing matrix to the outside surrounding. In this embodiment, the closing matrix supports and may enhance the flow that is induced by the collection matrix. This embodiment has advantages in conjunction with the flow-assisted sub-aspect. The closing matrix preferably is oriented at the cathode.

The closing matrix is hydrophilic. The closing matrix may comprise or consist of a charged, polarizable and/or dielectric material. Preferably, it comprises or consists of a negatively charged, negatively polarizable and/or dielectric material. This embodiment is particularly suitable in case a negatively charged target molecule, such as a nucleic acid, is purified. In this embodiment, the closing matrix is oriented at the cathode.

The closing matrix is preferably porous. According to one embodiment, the porous closing matrix has a pore size selected from the range of 0.1 µm to 100 µm, 0.25 µm to 50 µm, 0.5 µm to 20 µm, 0.6 µm to 15 µm, 0.7 µm to 10 µm, 0.8 µm to 7.5 µm, 0.9 µm to 5 µm and 1 µm to 5 µm. Such pore sizes are particularly suitable in case the closing matrix is made of a silicon containing material, which preferably is a siliceous material, such as silica and/or glass.

According to one embodiment, the closing matrix has a MWCO that lies in the range selected from 1 kDa to 500 kDa, 5 kDa to 300 kDa, 10 kDa to 200 kDa, 10 kDa to 100 kDa and 10 kDa to 50 kDa.

According to one embodiment, the closing matrix, which preferably is porous, is a filter or membrane, preferably a membrane. It can be an ultrafiltration membrane or a microfiltration membrane as is demonstrated by the examples. In addition, deep bed filters may be used as closing matrix.

The closing matrix can comprise or consist of the same material as the collection matrix. Suitable materials were described above and it is referred to the respective disclosure which also applies with respect to the closing matrix. A material can be rendered hydrophilic by appropriate treatments, such as e.g. functionalization. Respective hydrophobic materials that are rendered hydrophilic are also commercially available. Preferably, the closing matrix comprises or consists of a material selected from cellulose materials (such as a cellulose material selected from cellulose acetate materials, such as cellulose acetate, cellulose diacetate and cellulose triacetate and cellulose nitrate), polyethersulfone (PES), a mineral oxide and silicon containing materials, such as siliceous materials, preferably silica and/or glass. More preferably, the closing matrix comprises or consists of regenerated cellulose (RC), a cellulose acetate material or a siliceous material such as silica or glass.

According to one embodiment, a siliceous fiber membrane, also referred to as fiber fleece, e.g. made of silica or glass, is used as closing matrix. It may have an average pore size that lies in a range selected from 0.5 µm to 10 µm, 0.75 µm to 5 µm and 1 µm to 3.5 µm. This embodiment is preferred when isolating a nucleic acid as target molecule. This embodiment is particularly preferred when isolating the target molecule according to the electro-kinetic sub-aspect of the invention but can also be used in the flow-assisted sub-aspect of the invention.

According to one embodiment, the closing matrix has a pore size that is larger than the pore size of the collection matrix. Having a closing matrix with a larger pore size can support the pressure equalization in the passage (e.g. in the loading chamber) which assists in that an overflow of running solution out of the passage is prevented. This embodiment is e.g. advantageous in conjunction with the flow assisted sub-aspect of the present method as it supports the flow assisted purification process, in particular when purifying a negatively charged target molecule. The closing matrix is here preferably made of a cellulose acetate material, e.g. cellulose acetate or a siliceous material. Suitable embodiments and pore sizes were described above.

According to one embodiment, the closing matrix is made of a siliceous material, preferably silica or glass, and has a pore size that lies in the range of 0.5 µm to 10 µm, 0.75 µm to 7.5 µm, 0.75 µm to 5 µm and preferably 1 µm to 3.5 µm. This embodiment can be used in conjunction with the flow-assisted and the electrokinetic sub-aspect as is demonstrated by the examples by using e.g. an appropriately balanced collection matrix in combination.

According to a further embodiment, the closing matrix has a pore size that lies in the same range as the pore size of the collection matrix and wherein the closing matrix and the collection matrix have a MWCO in a range between 1 kDa and 300 kDa, preferably 3 kDa and 200 kDa, more preferred 5 kDa to 150 kDa, such as 10 kDa to 100 kDa. As is demonstrated by the examples, this embodiment has advantages in conjunction with the electro-kinetic sub-aspect of the present method, wherein a negatively charged target molecule such as a nucleic acid is purified. This combination of closing matrix and collection matrix helps to suppress flows within the passage thereby allowing a substantially unhindered purification along the electric field lines.

According to one embodiment the passage of the device at least in part is filled with a fluid, e.g. the running solution, during loading of the target molecule to be purified. This can even be the case, if the device is handled by its own and outside of other devices, for example outside an electrophoresis chamber. In such an embodiment, the closing matrix supports to prevent that the fluid, respectively contained target molecules, flow out of the passage while the device is being handled. The closing matrix can prevent that fluid or target molecules from flowing out of the passage e.g. before an electric field is applied.

In a preferred embodiment, wherein the device is placed in an electrophoresis chamber with the closing matrix facing the cathode, the closing matrix preferably allows positively charged inhibitors that are small enough to pass through the closing matrix to exit the device through the closing matrix when the electric field is applied. Moreover, in case a flow assisted purification is performed, also negatively charged inhibitors/impurities can exit the passage through the closing matrix, if their charge density is sufficiently small to prevent migration of these negatively charged inhibitors/impurities against the induced flow towards the anode in the applied electrical field.

According to a preferred embodiment, the passage comprises a liquid permeable separation matrix. In case the passage is closed by a liquid permeable closing matrix, what is as described preferred, the liquid permeable separation matrix is placed between the closing matrix and the collection matrix. The separation matrix is permeable for the running solution and the target molecule. The separation matrix allows the charged target molecule to move preferably unhindered along the electric field lines. Upon application of the electric field, a charged target molecule begins to migrate towards the corresponding electrode, i.e. the anode in case of a negatively charged target molecule, and passes the liquid permeable separation matrix.

The use of a separation matrix is preferred because it forms a barrier in the passage and thereby can achieve that macroscopic compounds such as e.g. a solid phase (e.g. magnetic beads) and/or cellular debris cannot pass the separation matrix but are retained e.g. in the loading chamber as will be described in further detail herein. This improves the purification result. When the purified target molecule is collected from the passage (e.g. from the collection chamber), the separation matrix prevents that cellular debris or other macromolecular contaminants or a solid phase present in front of the separation matrix (e.g. in the loading chamber of the device) are being collected together with the purified target molecule. The porous separation matrix can thus function as a filter. The pores of the separation matrix are sufficiently small, so that undesired solid compounds cannot pass the separation matrix. The separation matrix may also assist in the depletion of inhibitors of downstream applications of the target molecule, thereby assisting the purification result. For this purpose, the separation matrix can also provide a functionalized surface to specifically bind certain substances.

According to one embodiment, a negatively charged target molecule is purified and negatively charged inhibitors of appropriate size may pass the separation matrix and depending on the pore size of the collection matrix can exit the device through the collection matrix, whereby the purity of the target molecule, e.g. a nucleic acid, is increased. This embodiment is e.g. feasible in conjunction with the electro-kinetic sub-aspect of the invention.

The separation matrix preferably does not provide a substantial barrier to flow effects within the device. In prior art devices, the separation matrix is designed such that it reduces the electroosmotic flow within the device. Accordingly, in such devices, the separation matrix provides a barrier to electroosmotic flows which can go into the opposite direction than the target molecule (such as a nucleic acid) migrates in the electric field. As is described herein and shown by the examples, induced flows (e.g. due to an electroosmotic flow) can induce migration of a negatively charged target molecule (such as a nucleic acid) into the direction of the cathode which can result in an unwanted loss of nucleic acids. The prior art which uses a separation matrix which minimizes and thus suppresses such unwanted flows within the passage of the device is confronted with problems. If the separation matrix provides a substantial barrier to such flows that occur within the device, this can have the effect, that e.g. the collection chamber overflows or that the separation matrix is pushed through the device. In a preferred embodiment of the invention, a different principle is applied. In this embodiment, the separation matrix does not substantially disturb flows within the passage and accordingly, does not form a barrier for such flows. Instead, the collection matrix, optionally in combination with the closing matrix and/or the electric field strength, have the task to adjust and hence control such flows by controlling the entry and exit of liquid into and out of the passage of the device. In one embodiment, the collection matrix and optionally the closing matrix if present, are therefore the elements with the highest flow resistance and therefore control the entry and exit of liquid into and out of the passage of the device. Flows within the passage of the device, such as in particular induced by an electroosmotic flow, can thus be minimized by a careful choice/adaption of the closing and collection matrices as is demonstrated by the examples. However, the separation matrix is preferably not designed to present a flow barrier, thereby supporting to prevent undesired leakage of liquid and hence target molecule out of the passage. As is shown herein, e.g. an overflow of the eluate chamber and/or the loading chamber can be prevented and it supports that the fluid level within the passage remains substantially equal during operation. This allows e.g. an efficient separation of the target molecule according to its charge and/or charge density by the applied electric field.

The separation matrix may extend within the passage of the device over a length of 0.1 mm to 25 mm, 0.5 mm to 20 mm, 1 mm to 15 mm or 1.5 mm to 10 mm. According to one embodiment, the separation matrix extends within the passage over a length of 2 mm to 20 mm, 3 mm to 15 mm or 4 mm to 10 mm. In embodiments, the separation matrix has a length of 10 mm or less, preferably 7.5 mm or less. This also depends on the used material. It is an advantage that the device can be designed small.

A suitable material for the separation matrix has to be hydrophilic to ensure a continuous liquid bridge for charge transportation. The separation matrix is preferably porous. According to a preferred embodiment, a porous filter or membrane is used as separation matrix.

The separation matrix can comprise or consist of the same material as the collection matrix. Suitable materials were described above in conjunction with the collection matrix and it is referred to the respective disclosure which also applies with respect to the separation matrix. According to one embodiment, the separation matrix is provided by a packed bed to provide a filter function. Preferably, the separation matrix comprises or consists of a material selected from cellulose materials (examples were described above), PP, PE, nylon or PVDF. More preferably it comprises or consists of cellulose acetate or PE. It can be provided by a cigarette filter material. According to one embodiment the separation matrix is provided by a hydrophilic PE filter such as a PE frit. Hydrophobic materials such as e.g. PE and PP can be treated in order to render them hydrophilic. Suitable means to achieve hydrophilic properties are known to the skilled person and respective hydrophobic base materials that are rendered hydrophilic are also commercially available.

As described, the separation matrix is preferably porous and does not present a substantial barrier to flow effects within the passage, thereby preventing e.g. an undesired overflow of the running solution from the passage. According to one embodiment such porous, liquid permeable separation matrix is provided by choosing an appropriate porous material for providing the separation matrix. This option is preferred and suitable examples are described above. Alternatively or additionally, one or more pressure equalization channels can be formed within the separation matrix in order to allow pressure equalization in case flows occur within the passage of the device. Such channels are provided preferably in the upper third or quarter of the separation matrix. This supports to prevent that contaminants such as cellular debris contaminate the purified target molecule when it is removed e.g. from the collection chamber. According to one embodiment, no pressure equalization channels are provided.

Classical electrophoretic separation materials such as agarose or PAA are not well suitable materials for providing a separation matrix that can be used in conjunction with the invention as they represent a barrier to flows that occur within the passage, in particular the flow that can be induced by the collection matrix. It was found that such materials pose a risk that the sample leaks out of the device due to flow effects, such as electroosmotic flow. This particularly, if no means for pressure equalization, such as channels in the matrix, are provided as is shown in example 9. Therefore, preferably, no gel is used as material for the separation matrix. According to one embodiment, the separation matrix does not substantially induce or support a flow effect within the passage, such as in particular an electroosmotic flow. According to one embodiment, the separation matrix neither comprises a gel. According to one embodiment, no matrix of the device, i.e. neither the closing matrix, the separation matrix nor the collection matrix, is a gel or comprises a gel.

According to one embodiment, the separation matrix is a removable discrete body that can be inserted into the passage of the device. The portion of the passage that comprises the separation matrix is also referred to herein as separation section. According to one embodiment, the device comprises more than one separation matrix. According to one embodiment, closing matrix and separation matrix are provided by the same element which may function e.g. as a loading pad. Details are described elsewhere herein. Preferably, however, the separation matrix and the closing matrix are provided as separate elements in the device, thereby forming a loading chamber.

According to the invention, one end of the passage formed in the device, the front end, is closed by a liquid permeable collection matrix and in a preferred embodiment the other end of the passage, the rear end, is closed by a liquid permeable closing matrix. Preferably, the choice of material for the collection matrix and the closing matrix is such that when the thus obtained device is used in the method, wherein an electric field of a predetermined strength is being applied, a desired flow of running solution is generated in the passage. Details were already described above.

As described above, one desired flow of running solution relates to the "flow-assisted" sub-aspect of the invention, where the choice of the collection matrix and electric field strength is made to create a flow sufficiently strong to have an desired effect on the unwanted elements in the passage (e.g. impurities), while the role of the electric field with regard to the target biomolecule predominantly is to avoid that target molecule is flushed out of the passage. As described, the electric field is preferably sufficiently strong to induce migration of the charged target molecule to the collection matrix, whereby the target molecule passes the separation matrix, if a separation matrix is present in the passage. This embodiment is particularly suitable for isolating a negatively charged target molecule such as DNA from different biological samples, including challenging samples such as blood.

According to one embodiment, an ultrafiltration membrane is used as collection matrix which has a MWCO in the range of 1 kDa to 300 kDa, 1 kDa to 200 kDa, 3 kDa to 100 kDa or 5 kDa to 50 kDa. Preferred materials for the ultrafiltration membrane that is used as collection matrix include, but are not limited to CA, CTA, RC and PES. The closing matrix that is used in combination can be made of a porous siliceous material and can e.g. be provided by a silica or glass, e.g. in form of a fleece or membrane. The pore size of the closing matrix can be larger than the pore size of the collection matrix as was described in detail above.

According to one embodiment, the separation matrix is made of the same material as the closing matrix. This embodiment is e.g. feasible for use in the flow-assisted sub-aspect of the invention. According to one embodiment, the separation matrix and the closing matrix comprises or consists of a material selected from cellulose materials (examples were described above), PP, PE, nylon or PVDF. Preferably they comprise or consist of cellulose acetate or PE. According to one embodiment the separation matrix and the closing matrix is provided by a hydrophilic filter made of cellulose acetate or PE, such as e.g. a hydrophilic PE frit. The closing matrix and the separation matrix can be provided e.g. by a cigarette filter material (cellulose acetate) as is demonstrated by the examples.

Suitable combinations of collection matrix, closing matrix and separation matrix, if present, that can be used in conjunction with the flow-assisted aspect are also described in the examples and are also listed in the below table.

As described above, a further desired flow of running solution relates to the "electrokinetic" sub-aspect, where the choice of the collection matrix, preferably in combination with a closing matrix, and electric field strength is made to create a flow sufficiently reduced within the passage to not disturb the electric-field driven transport of the charged target molecule and optionally other equally charged molecules towards the collection matrix. To optimize the flow characteristics within the device, the closing matrix and the collection matrix can be adapted such that the flow of the running solution through the device is substantially static. In a preferred embodiment, the closing matrix and the collection matrix are matched in order to prevent that the passage or sections thereof, e.g. the loading chamber or the collection chamber, run empty during operation, i.e. run empty when the electric field is applied, or overflow. The loading chamber can run e.g. empty, if the flow through the closing matrix and out of the passage is stronger than the flow through the collection matrix and into the passage. The examples show using a negatively charged dye as test molecule how induced flows such as the electroosmotic flow and the electrical field can oppose each other. In principle, the negatively charged dye should migrate to the anode because of the applied electric field. However, if induced flows within the cartridge are too strong, the negatively charged dye is pushed into the opposite direction, i.e. into the direction of the cathode. Thus, the induced flow, presumably being the result of an electroosmotic flow generated by the collection matrix, is stronger than the electric field. This can, if too strong, counteract an efficient separation of the target molecule based on charge. Moreover, if the flow resistance/current resistance within the passage is too high, this creates a risk that the target molecule leaks out of the device, e.g. the eluate chamber, as is demonstrated by the examples. On the other hand, as is demonstrated by the

| Closing Matrix | Separation Matrix | Collection Matrix | |
|---|---|---|---|
| Cellulose material, preferably a cellulose acetate material, more preferably a CA filter; or a porous, siliceous material, preferably a silica or glass fiber filter or membrane. The pore size of the siliceous material is according to one embodiment 0.5 µm to 10 µm, 0.75 µm to 5 µm, preferably 1 µm to 3 µm, more preferred 1 µm. | Cellulose material, preferably a cellulose acetate material, more preferably a CA filter; or a hydrophilic PE filter | MWCO: 1 kDa to 300 kDa, preferably 5 kDa to 100 kDa | PES or a cellulose material, preferably RC or a cellulose acetate material, more preferably CTA. |
| Porous, siliceous material, preferably a silica or glass fiber filter or membrane. The pore size is according to one embodiment 0.5 µm to 10 µm, 0.75 µm to 5 µm, preferably 1 µm to 3 µm, more preferred 1 µm. | Cellulose material, preferably a cellulose acetate material, more preferably a CA filter; or a hydrophilic PE-filter | MWCO: 1 kDa to 100 kDa, preferably 5 kDa to 50 kDa, e.g. 10 kDa | CTA, RC or PES |
| Porous, siliceous material, preferably a silica or glass fiber filter or membrane. The pore size is according to one embodiment 0.5 µm to 10 µm, 0.75 µm to 5 µm, preferably 1 µm to 3 µm, more preferred 1 µm. | Hydrophilic PE-filter or a cellulose material, preferably a cellulose acetate material, more preferably a CA filter | MWCO: 1 kDa to 200 kDa, preferably 5 kDa to 50 kDa, e.g. 10 kDa | PES |
| Porous, siliceous material, preferably a silica or glass fiber filter or membrane. The pore size is according to one embodiment 0.5 µm to 10 µm, 0.75 µm to 5 µm, preferably 1 µm to 3 µm, more preferred 1 µm. | Cellulose material, preferably a cellulose acetate material, more preferably a CA filter; or a hydrophilic PE filter | MWCO: 1 to 50 kDa, e.g. 1, 3, 5 or 10 kDa | Cellulose material, preferably RC | flow-assisted sub-aspect, this induced flow can, properly adjusted, be used in order to support the purification result as is can be used to flush out impurities, including negatively charged impurities, that have a lower charge density than the target molecule.

The separation matrix, the collection matrix and the closing matrix can be adapted to each other as described herein to allow pressure equalization e.g. in case an electroosmotic flow occurs. The flow-through characteristics can be modulated to allow pressure equalization which can also prevent running buffer overflow in the chambers. In the electro-kinetic sub-aspect of the invention, the collection matrix and the closing matrix are adapted to each other with regard to porosity and/or material in order to prevent migration of a negatively charged target molecule and optionally other molecules of equal charge into the direction of the cathode when the cartridge is in use. The collection matrix and the closing matrix are in embodiments those elements with the highest flow resistance and therefore control the entry and exit of liquid into and out of the passage. In order to suppress inner-tube flow effects, a matrix having a small pore size is used in one embodiment as closing matrix and as collection matrix. E.g. an ultrafiltration membrane can be used as closing matrix and as collection matrix. The ultrafiltration membrane may have a MWCO in the range of 1 kDa to 300 kDa, 1 kDa to 200 kDa, 3 kDa to 100 kDa or 5 kDa to 50 kDa, such as 10 kDa. For isolating RNA an ultrafiltration membrane is preferably used as collection matrix having e.g. a MWCO in the range selected from 1 kDa to 50 kDa, 3 kDa to 20 kDa, e.g. 5 kDa to 10 kDa. Preferred materials for the ultrafiltration membrane include, but are not limited to CA, CTA, RC and PES. Such ultrafiltration membranes are preferably used in combination with a separation matrix which has macropores in the micrometer range and therefore allows a substantially unhindered flow within the passage. Using an ultrafiltration membrane as closing matrix and as collection matrix is advantageous, because it allows to reduce and hence suppress flows within the passage, thereby allowing an efficient electro-kinetic separation based on charge as is demonstrated by the examples.

According to a further embodiment, an ultrafiltration membrane is used as collection matrix which has a MWCO in the range of 1 kDa to 300 kDa, 1 kDa to 200 kDa, 3 kDa to 100 kDa or 5 kDa to 50 kDa. Preferred materials for the ultrafiltration membrane that is used as collection matrix include, but are not limited to CA, CTA, RC and PES. The closing matrix that is used in combination is made of a porous siliceous material and can e.g. be provided by a silica or glass, e.g. in form of a fleece or membrane. The pore size of the closing matrix can be larger than the pore size of the collection matrix as was described above. Also this embodiment allows an efficient purification of a charged target molecule, in particular a negatively charged target molecule such as a nucleic acid using the electro-kinetic sub-aspect of the invention as is demonstrated by the examples.

Suitable combinations of collection matrix, closing matrix and separation matrix, if present, that can be in particular used in conjunction with the electro-kinetic aspect are also described in the examples and are also listed in the below table.

| Closing Matrix | Separation Matrix | Collection Matrix | |
| --- | --- | --- | --- |
| CA, having a MWCO in the range of 10 kd-100 kDa, preferably 10 kDa | Cellulose material, preferably a cellulose acetate material, more preferably a CA-filter | 1 kDa to 300 kDa, preferably 5 kDa to 100 kDa, in particular 10 kDa. | CTA or PES, preferably CTA |
| Siliceous material, preferably a glass fiber fleece or silica membrane. The pore size is according to one embodiment 0.5 µm to 10 µm, 0.75 µm to 5 µm, preferably 1 µm to 3 µm, more preferred 1 µm. | Cellulose material, preferably a cellulose acetate material, more preferably CA-filter; or hydrophilic PE filter | 1 kDa to 300 kDa, preferably 5 kDa to 100 kDa, in particular 10 kDa. | PES or a cellulose material, preferably RC or a cellulose acetate material, more preferably CTA or PES, preferably PES |

The device can be prepared or pre-filled with the closing matrix, the separation matrix and the collection matrix. Closing matrix, separation matrix and the collection matrix can be fixed relative to each other. The closing matrix and the collection matrix form a barrier for the target molecule in the respective ends of the passage. This prevents a loss of target molecule. Closing matrix and collection matrix preferably terminate the passage with regard to the fluidic transfer into and out of the device and therefore control the liquid flow into and out of the passage.

In a preferred embodiment the length of the device is 1.25 cm to about 7 cm, preferred about 1.5 cm to about 6 cm, more preferred about 1.75 cm to 5 cm, and even more preferred about 2 cm to 4 cm, e.g. 2.5 cm to 3 cm. A small size simplifies the handling of the device and has advantages regarding the field strength that can be used.

The passage is preferably hollow. The passage is preferably elongated and comprises according to a preferred embodiment a liquid permeable closing matrix and/or a liquid permeable separation matrix in addition to the liquid permeable collection matrix. The target molecule to be purified is placed between the closing matrix and the separation matrix. Suitable embodiments for placing the target molecule into the passage are described herein. Preferably, a loading chamber is formed between the closing matrix and the separation matrix and/or a collection chamber is formed between the separation matrix and the collection matrix.

The passage that is formed in the device preferably has a cross section, preferably diameter, in the mm to cm range. E.g. the cross section can lie in the range selected from 1 mm to 30 mm, 1.5 mm to 25 mm, 2 mm to 20 mm, 2.5 mm to 15 mm and 3 mm to 10 mm. The device, respectively the provided passage, is preferably tube-shaped, so that the cross section refers to the diameter. The cross section can vary over the length of the passage and can e.g. be equal or reduced along the passage from the rear end to the front end (where the collection matrix is located).

As is described herein, the device is preferably a hollow, elongated body with openings at both ends, thereby forming a passage. The passage is likewise elongated. The closing matrix, if present, is positioned in one end region of the device and the collection matrix is positioned in another end region of the device. The elongated body can comprise further openings to simplify entry and removal of the target nucleic acid to and from the passage. The device can be a replaceable unit. According to one embodiment, it is a discrete body that can be placed into an electrophoresis chamber when performing the method and does not comprise electrodes. According to a further embodiment, the device is provided as integrated cartridge which comprises the electrodes and a reservoir for the running solution. In this embodiment, the device can also provide the functions of the electrophoresis chamber. Such device can be provided as closed system e.g. for diagnostic applications. It comprises openings for entry and removal of the target molecule and may comprise circuit points. Preferably, the device is a disposable consumable what is convenient for the user. As described, a device according to the second aspect is preferably used in the method.

The passage of the device is via the collection matrix and the closing matrix, if present, in fluid communication with the exterior, such as e.g. the electrophoresis chamber. The device is preferably a hollow, elongated tube wherein the closing matrix is located at one end region of the tube and the collection matrix is located at the other end region of the tube. It may comprise one or more openings at the top in order to simplify introduction and removal of the target molecule.

According to one embodiment, the device
comprises a loading chamber which is formed at least in part by the closing matrix and the separation matrix and wherein the target molecule is placed into the loading chamber; and
comprises a collection chamber which is formed at least in part by the separation matrix and the collection matrix and wherein the purified target molecule is collected from the collection chamber.

The loading chamber and the collection chamber are formed in the passage of the device. According to one embodiment, the collection matrix separates the collection chamber from the anode and the closing matrix separates the loading chamber from the cathode. This set-up is suitable for isolating a negatively charged target molecule such as a nucleic acid. At least during electrophoretic separation the loading chamber is located in the region of the cathode and the collection chamber is located in the region of the anode. During operation, the loading chamber and the collection chamber contain the running solution. During operation, positively charged inhibitors migrate to the cathode. Neutral inhibitors predominantly do not move and remain in the loading chamber. Small negatively charged inhibitors can pass the separation matrix and the collection matrix and exit the device and/or are flushed out of the passage at the cathodic side due to the induced flow. As is shown by the examples, in the flow-assisted sub-aspect, negatively charged inhibitors that have a smaller charge density than the target molecule can be flushed out at the cathodic side because of the induced flow which exerts a stronger force than the electric field. This allows the separation of equally charged molecules based on their charge density. Thereby, a thorough purification of the negatively charged target molecule is achieved as is demonstrated by the examples.

According to one embodiment, the loading chamber comprises at least one opening in order to facilitate introduction of the target molecule to be purified into the passage of the device. The collection chamber may comprise at least one opening in order to simplify removal of the purified target molecule. These openings are particularly advantageous if the device is provided as hollow body, such as in form of an elongated tube. The one or more openings are at the top of the device and may have a "collar" to balance volume variations e.g. due to temperature or flow effects.

According to one embodiment, the device has an elongated body, preferably tube-shaped, which comprises in the passage a loading chamber that is formed at least in part by a liquid permeable closing matrix and a liquid permeable separation matrix and wherein target nucleic acid is placed into the loading chamber, optionally while being bound to a solid phase, through an opening and wherein the device comprises in the passage a collection chamber that is formed at least in part by the separation matrix and the collection matrix and wherein the eluted target nucleic acid is collected from the collection chamber through an opening in the device.

Preferably, a device is used which does not comprise the electrodes for generating the electric field and accordingly, does not comprise a functional cathode and/or a functional anode. Instead, the device is placed in an electrophoresis chamber which comprises the electrodes for generating the electric field. This is preferred, because it allows designing the device as consumable that can be used in combination with an electrophoresis chamber. After use, the device can be disposed. This allows a cost-efficient design of the device. Hence, the device may be provided as a discrete body, preferably as cartridge, that does not comprise electrodes for generating the electric field and wherein the device is at least during the electrophoretic separation step placed into an electrophoresis chamber which comprises the electrodes for generating the electric field and is filed during operation with the running solution. The passage of the device is via the collection matrix and the closing matrix, if a closing matrix is present, in fluid communication with the electrophoresis chamber. The device, optionally already loaded with the target molecule, can be placed into the electrophoresis chamber. The electrophoresis chamber may be filled with running solution when the device is placed or mounted in the chamber or in advance thereto. The device and the electrophoresis chamber may comprise the same running solution. The prior art systems often use different buffers within the same cartridge and/or the electrophoresis chamber to prevent an overflow of chambers. Such systems are more complicated and prone to errors. Advantageously, the device of the invention can be operated with a single running solution. The electrophoresis chamber can retain an amount of running solution that is sufficiently large in order to maintain the pH value within an acceptable range. Thus, the running solution reservoir of the electrophoresis chamber and hence the size of the electrophoresis chamber is preferably adapted in order to allow maintenance of the pH value and hence prevents that the pH value during separation is lowered beyond an acceptable value. Suitable pH ranges are described herein.

The electrodes comprised in the electrophoresis chamber are preferably adapted in size and dimension to the device. This secures a maximal energy transfer (electric to kinetic) from electrode to the target molecule. Adjustment of both components results in minimal input of unused electric energy which will otherwise simply heat the chamber in which case cooling of the system might be required to avoid damage of the target nucleic acid. The method can be operated such that the electrophoresis chamber is not substantially heated during the electric field based purification. It is advantageous that a set-up is used wherein the temperature of the running solution remains within an acceptable range. The electrophoresis chamber may optionally comprise a temperature sensor.

In one embodiment, the electrodes have a size which corresponds to the size of an end opening of the device which faces the electrode. Thus, the size and dimension of the anode and the cathode that are located in the electrophoresis chamber are adapted to the size and dimension of the end openings of the device between which the passage is formed. They may also be adapted to the size and dimension of the closing matrix and separation matrix. This embodiment is particularly advantageous if the device is designed as hollow elongated tube with openings at both ends which comprise the closing matrix and the collection matrix. The electrodes are in one embodiment parallel to the closing matrix and the collection matrix. The electrodes of the electrophoresis chamber and the end regions of the device are thus in one embodiment adjusted on a substantially straight line towards each other. Additionally, the shape of the electrodes may correspond to the shape of the openings facing the electrode. The device is preferably a hollow tube. According to one embodiment, discoid electrodes are used. This is e.g. advantageous if a tube shaped device is used. According to one embodiment, disc-shaped (discoid) electrodes are provided in the electrophoresis chamber and are located near the end regions of the tube shaped device when the device is placed into the electrophoresis chamber. Thus, according to a preferred embodiment, the used device is a hollow tube and a liquid permeable closing matrix is located at one end region of the tube and the collection matrix is located at the other end region of the tube whereby the passage is formed between the closing matrix and the collection matrix and wherein the closing matrix is located in the region of the cathode and the collection matrix is located in the region of the anode and wherein optionally, the electrodes of the electrophoresis chamber are parallel to the closing matrix and the collection matrix of the device and wherein optionally, the electrodes are adapted in dimension and shape to fit the dimension and shape of the closing matrix and the collection matrix. In one embodiment, they are disc-shaped.

The electrodes are in one embodiment axial extensions of the device and may also have identical dimensions (diameter) to avoid unnecessary input of energy. The electrodes may have a small thickness, preferably less than 5 mm, more preferred less than 2 mm. In a preferred embodiment the electrodes are encapsulated exposing a face of the electrode which corresponds to the shape and the size of the opening of the device facing the electrode. In a preferred embodiment, the electrophoresis chamber comprises orientation members which allow orientating the device in the proper direction with regard to the polarization of the electrodes for applying the electric field.

The device is placed between the two electrodes of the electrophoresis chamber. It is advantageous that the device is small to keep the distance between the electrodes narrow. A maximal electrical current flow is desired. When the device is placed into the electrophoresis chamber, the anode is located in close proximity to the collection matrix and the cathode is located in close proximity to the closing matrix of the device if a negatively charged molecule is purified. The arrangement is reverse, if the target molecule is positively charged. According to one embodiment, the distance between the electrodes is 10 cm or less, 8 cm or less, 7 cm or less, 5 cm or less, 4.5 cm or less when the device is placed into the electrophoresis chamber. According to one embodiment, the minimum distance between the electrodes is at least 2 cm, at least 2.5 cm or preferably at least 3 cm. A corresponding small design of the device is advantageously possible with the device according to the second aspect of the present invention. A small distance between the electrodes advantageously allows a relatively high field strength by minimal applied voltage. The field strength is calculated based on the voltage and the distance between the electrodes. The electrodes should be placed in close proximately to each other in order to allow the use of a low voltage. According to one embodiment, the method is operated using a field strength selected from 1 to 20V/cm, 3V/cm to 17V/cm and 5V/cm to 15V/cm, preferably 10V per cm. For example, if the electrodes have a distance of 4 cm and the field strength is 10V per cm, this amounts to a voltage of 40V. Such low voltage is advantageous, because this low energy input avoids an undesired heating of the system as was confirmed for the method of the invention by temperature monitoring during the run. According to one embodiment, the voltage applied is in the range of about 20V to about 150V, preferred about 25V to about 100V, more preferred 25V to 75V, even more preferred 25 V to 50V to achieve the field strength described above. For constant input voltage for a given chamber/buffer system the power is $P=U*I$. The unit is 1 W (Watt)=1 J (Joule)/s. 1 J is the heat required to raise the temperature of 1 g of water by 0.24 K. So 1 W is the power required to raise the temperature of 1 g of water in 1 second by 0.24 K. Assuming constant current (identical buffer and flow-tube geometry) the voltage is directly proportional to the input power. For example, a typical electrophoresis chamber operates with an electrode distance of 15 cm. To achieve desired electric field strength of for example 10V/cm a five-fold higher power is necessary to achieve the same field strength. Therefore these known systems need external cooling or large buffer reservoirs. These drawbacks can be avoided by the method of the invention. Preferably, an electrophoresis chamber is used that is adapted to the dimension of the device.

It was found that the electroosmotic flow can be influenced by the distance of the electrodes even when employing a constant field strength. The smaller the distance between the electrodes at the same field strength, the smaller is the electroosmotic flow. This can be adjusted, if desired, by choosing a larger pore size for the collection membrane.

Even if the collection matrix does not bind the target molecule under the used conditions, the target molecule, such as a target nucleic acid may become because of the electric field nevertheless closely attached to the collection matrix. This can render a complete collection of the target molecule from the device difficult. To assist a substantially quantitative collection of the target molecule, it is advantageous to briefly reverse the electric field in order to induce migration of the target molecule away from the collection matrix. Thereby, the target molecule detaches from the collection matrix and can be easily collected. The reversal is sufficiently brief to prevent that the target molecule enters the separation matrix, if present. E.g. the reverse electric field can be applied for 1 to 60 s. This may also depend on the applied electric field strength. The target molecule can e.g. be collected from the collection chamber of the device through an opening at the top of the collection chamber what is preferred in case the device is a hollow body such as an elongated tube.

During performance of the method, the passage is or becomes filled with a running solution to allow an electrophoretic purification of the target nucleic acid. This principle is well-known in the art. The running solution conducts the electric current and therefore comprises ions. The running solution has an ionic strength that is high enough in order to ensure that the electric current is conducted. However, if the salt concentration is too high, this is disadvantageous, because either the electric tension or the electrical current flow is hindered which can disturb the quality of the purification result. A low salt concentration is furthermore advantageous, because the running solution purifies the target molecule as impurities are removed during the electric field based separation and the target molecule is collected in the running solution. A low salt concentration is therefore advantageous as it allows to use the purified target molecule, e.g. a nucleic acid, in many down-stream reactions without requiring e.g. a desalting step. E.g. buffers that are used in gel electrophoresis of nucleic acids can be used to provide ions that carry a current and to maintain the pH at a relatively constant value. In embodiments described herein the running solution additionally functions as elution solution.

According to one embodiment, the running solution has an ionic strength of an ionic compound of 1 mM to 200 mM, 5 mM to 150 mM, 10 mM to 100 mM, preferred 15 mM to 75 mM and especially preferred 20 mM to 50 mM. According to one embodiment, this refers to the overall ionic strength.

The pH of the running solution can lie e.g. in a range of 6 to 9.5, 6.5 to 9 and 7 to 8.5. The suitable pH also depends on the target molecule to be purified and can be chosen by the skilled person accordingly. Preferably, the running solution comprises a buffering agent. The buffering agent assists to maintain the pH during the electric field assisted purification in an acceptable range. E.g. when intending to purify a nucleic acid as target molecule, any biological buffer that is commonly used in nucleic acid elution solutions can be used as buffering agent in the running solution if it does not disturb the electric field based separation process. The buffering agent is preferably compatible with the intended downstream reaction, such as an amplification reaction. According to one embodiment, the buffer capacity of the buffering agent is such, that the pH is maintained during the electric field based purification process within 2 pH units, preferably within 1.5 pH units, more preferred within 1 pH unit.

The buffering agent may be e.g. selected from the group consisting of TRIS, MOPS, HEPES, MES, BIS-TRIS, glycine and carboxylic acids like acetate or citrate. Other biological buffers are also known to the skilled person that provide a buffering capacity in the desired pH range. According to one embodiment, the running solution comprises the buffering agent in a concentration of 7.5 mM to 150 mM, 10 mM to 100 mM, 15 mM to 75 mM, 20 mM to 70 mM, 20 mM to 65 mM, 25 mM to 60 mM and 30 mM to 55 mM.

According to one embodiment, the running solution comprises a salt, preferably an alkali metal salt, preferably in a concentration of 100 mM or less or 75 mM or less. According to one embodiment, the overall salt concentration in the running solution, including any buffering agent if present as a salt, is selected from 7.5 mM to 200 mM, 10 mM to 175 mM, 15 mM to 150 mM, 20 mM to 125 mM, 25 mM to 100 mM and 30 mM to 75 mM.

The inventors found that some classical electrophoretic solutions such as TBE buffer are less suitable as running solution because they may disturb because of their ingredients certain downstream reactions. As the target molecule is collected in the running solution it should not contain components) that could disturb the intended downstream application, such as for example an amplification reaction or an enzymatic digestion. Therefore, using a running buffer as it is described herein is advantageous for the purification result and the performance of the method.

According to a preferred embodiment, the running solution comprises as buffering agent Tris in a concentration of 7 mM to 100 mM, preferably 10 mM to 75 mM and has a pH in the range selected from 6.5 to 9, 7 to 8.75 and 7.5 to 8.5, preferably pH 8. The running solution may comprise Tris in a concentration of 30 mM to 60 mM, preferably 30 mM to 50 mM and may have a pH in the range of 7.5 to 8.5, preferably pH 8. As is demonstrated by the examples, such running buffer functions well in the method of the invention, in particular if DNA is isolated as target molecule. Preferably, it does not contain a further salt in a concentration above 50 mM, above 30 mM, above 25 mM, above 20 mM, above 15 mM or above 10 mM. Preferably, the running solution does not contain a salt in addition to Tris.

According to one embodiment, the buffering agent is MOPS. According to one embodiment, a running buffer comprising MOPS in a concentration of 5 mM to 50 mM, preferably 10 mM to 25 mM and having a pH in the range of 6.5 to 7.5 is used, wherein said running buffer optionally but preferably comprises a salt, preferably an alkali metal salt such as NaCl, in a concentration selected from 5 mM to 100 mM, 10 mM to 75 mM and 15 mM to 60 mM. This embodiment is particularly suitable for isolating RNA as target molecule. Also other running buffers used in RNA electrophoresis can be used.

Further suitable and preferred embodiments of the present method are described in the following.

According to a preferred embodiment, the method is for purifying a target nucleic acid as charged target molecule from a nucleic acid containing sample. The term "sample" is used herein in a broad sense and includes a variety of sources that contain nucleic acids. The sample may be a biological sample but the term also includes other, e.g. artificial samples which comprise nucleic acids. Preferably, the sample is a biological sample e.g. derived from a human, animal, plant, microorganism, virus or fungi. It can be a cell-containing sample. Exemplary samples include, but are not limited to body fluids and samples derived therefrom such as blood, serum, plasma, red blood cells, white blood cells, buffy coat, urine, furthermore cells, cell culture, tissues such as liver, spleen, kidney, lung, intestine, brain, heart, muscle, fat, pancreas; tumor cells, fetal cells, host and graft cells, swabs, sputum, saliva, semen, lymphatic fluid, liquor, amniotic fluid, cerebrospinal fluid, peritoneal effusions, pleural effusions, fluid from cysts, synovial fluid humor, bursa fluid, pulmonary lavage, lung aspirates, bone marrow aspirates, as well as lysates, extracts, or materials obtained therefrom. Materials obtained from clinical or forensic settings that contain or are suspected to contain nucleic acids are also within the intended meaning of the term sample. Furthermore, the skilled artisan will appreciate that lysates, extracts, or materials or portions thereof obtained from any of the above exemplary samples are also within the scope of the term sample.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. The method is suitable to purify DNA as well as RNA. DNA includes, but is not limited to all types of DNA, e.g. gDNA, circular DNA, plasmid DNA and circulating DNA. RNA includes but is not limited to hnRNA, mRNA extracellular RNA, noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA) and snRNA (small nuclear RNA). Preferably, the method is used for purifying DNA, preferably genomic DNA.

The target nucleic acid can be introduced by various means into the passage of the device.

In one embodiment, the target nucleic acid to be purified is placed into the passage of the device as part of a lysate. As is demonstrated by the examples, the method according to the invention allows the purification of nucleic acids, in particular DNA, directly from the lysate. The sample can be lysed using conventional chemistry and the lysate containing the target nucleic acid is then placed into the passage for the electric field assisted purification. Preferably, the nucleic acid is isolated from the lysate using the flow-assisted sub-aspect of the method as it is highly efficient and renders pure nucleic acids. Surprisingly, it was even possible to directly use a lysate comprising a high salt concentration as is demonstrated by the examples. According to one embodiment, the lysate comprises one or more salts, preferably chaotropic salts, in a concentration of at least 0.25M, at least 0.5M, at least 0.75M, at least 1M or at least 1.25M. The embodiment wherein directly the lysate is applied to the passage is advantageous, as it reduces hands on time and can be easily performed using an automated system. No binding to a solid phase is required which safes handling steps.

Lysis of the sample can be assisted by conventional means such as e.g. heating, mechanical disruption, ultrasound, enzymatic digestion and/or combinations thereof. E.g. one or more lytic enzymes and/or small particles can be added and agitated during lysis to support the disruption of the sample. In one embodiment, the salt concentration in the lysate is 2M or less, 1.75M or less, 1.5M or less, 1M or less, 0.75M or less, 0.6M or less, 0.5M or less, 0.4M or less or 0.3M or less. The lysate may also be diluted to adjust the salt concentration. The lysate may be optionally cleared to remove e.g. cell debris or other solid matter before transferring lysate into the passage of the device. The transferred lysate becomes diluted with the running solution which reduces the salt concentration. In one embodiment, the salt concentration is 0.5M or less, 0.35M or less, 0.3M or less, 0.25M or less, preferably 0.2M or less or 150 mM or less when the lysate is mixed with the running solution. In one embodiment, the ionic strength is 0.5M or less, 0.35M or less, 0.3M or less, 0.25M or less, preferably 0.2M or less or 150 mM or less when the lysate is mixed with the running solution. The suitable or optimal salt concentration or ionic strength can be identified e.g. by performing a dilution series with the lysate.

According to a preferred embodiment, the method combines binding of a target nucleic acid to a solid phase with the electric field purification procedure according to the invention. In this embodiment, the target nucleic acid contained in the sample is bound to a solid phase. A lysis step may be performed in advance or simultaneously to release the target nucleic acid if required. Advantageously, already existing and proven lysis and binding chemistry (e.g. chaotropic) can be used. Accordingly, the method of the invention may comprise binding the target nucleic acid contained in the sample to a solid phase, separating the bound nucleic acid from the sample and placing the target nucleic acid, optionally while being bound to the solid phase, into the passage of the device. Suitable embodiments for placing the target nucleic acid into the passage of the device are described below. The passage of the device preferably comprises a liquid permeable closing matrix and a liquid permeable separation matrix in addition to the liquid permeable collection matrix. The target nucleic acid is placed between the closing matrix and the separation matrix. Upon application of the electric field the target nucleic acid migrates towards the anode through the separation matrix and is retained at the collection matrix. The method may comprise placing the target nucleic acid, optionally while being bound to a solid phase, into the loading chamber of the device through an opening in the device;

applying the electric field, wherein the target nucleic acid migrates according to its charge in the electric field, passes through the separation matrix and is retained at the collection matrix;

optionally reversing the electric field; and collecting the purified target nucleic acid from the collection chamber through an opening in the device.

According to one embodiment, the target nucleic acid is placed into the passage of the device while being bound to a solid phase. After binding the target nucleic acid to a solid phase, the target nucleic acid is further purified by electrophoresis according to the present method. A major advantage compared to common isolation protocols is the possibility to omit extra pipetting and handling steps like the addition of washing and elution buffers or waste removal after the target nucleic acid was bound to the solid phase. The further purification and elution of the target nucleic acid can occur within the device and thus requires no further manual interaction. When the solid phase with the bound to nucleic acids is loaded into the device and subjected to the electric field, processing time may be fixed regardless of the amount of solid phase and/or the amount of target nucleic acid bound thereto or the original size and volume of the sample which is especially useful for large volume liquid samples. In this embodiment wherein the target nucleic acid is still bound to a solid phase (e.g. particles) the running solution additionally functions as elution solution. Accordingly, the running solution used in this embodiment is suitable to effect elution of the target nucleic acid from the solid phase wherein elution is optionally assisted by agitation and/or heating. In addition, it is advantageous to choose a running solution that is compatible with a subsequent nucleic acid analysis method, such as an amplification reaction. Suitable embodiments are described herein.

In this embodiment, wherein the target nucleic acid is placed into the passage of the device while being bound to a solid phase a separation matrix is preferably comprised in the passage. The separation matrix is preferably porous and has an average pore size that is smaller than the average size of a solid phase that is placed together with the target molecule to be purified into the passage of the device. The target nucleic acid either bound to the solid phase or eluted therefrom can be placed together with the solid phase into the passage of the device. In case particles such as magnetic particles are used as solid phase the average pore size of the separation matrix is smaller than the average diameter of the particles in order to efficiently prevent that the particles can pass or enter the separation matrix.

According to one embodiment, a device that is flooded with running solution can be provided and the solid phase, e.g. magnetic particles, with the bound nucleic acids, is placed as described into the passage of the device which comprises the running solution. The running solution may, however, also be introduced into the passage after the solid phase with the bound target nucleic was placed into the passage. The running solution supports in embodiments elution and elution can be assisted by heating and/or agitation. The device comprising the solid phase with the bound nucleic acids can e.g. be agitated, for example assisted by vortexing, the introduction of gas such as air into the mixture or by magnetic stirring, in order to mix the solid phase in the running solution to support elution. Such assistance (in particular by agitation) is in particular useful in case the target nucleic acid is large as is it the case e.g. with genomic DNA in order to ensure that it detaches from the solid phase. For smaller nucleic acids such as RNA or plasmids agitation is not required and this difference in the elution behavior can also be used in order to deplete e.g. undesired genomic contaminations in an RNA preparation when using the present method. The electric field may be generated afterwards. According to one embodiment, magnetic particles are used as solid phase. In this embodiment, a magnet can be used in order to support mixing of the magnetic particles within the loading chamber in order to assist the elution process. To assist elution, at least one magnetic stirring bar can be comprised in the loading chamber to assist the agitation of the magnetic particles that are used as solid phase (see e.g. DE 10 2007 045 474). Agitation is assisted by the use of at least one magnet, e.g. a permanent magnet or electromagnet, which is configured to interact with the magnetic material. The magnet is preferably located external of the device, e.g. in the electrophoresis chamber.

According to one embodiment, elution of the bound target nucleic acid is induced and/or is assisted by the electric field that is being applied. According to one embodiment, elution of the target nucleic acid at least partially occurs before the electric field is generated. The solid phase can be held back during the purification process by the separation matrix, if provided in the passage. In case magnetic particles are used as solid phase, the magnetic particles may be alternatively or additionally held back in the passage of the device by the aid of a magnet in order to allow the purification of the target nucleic acids free from the solid phase. The magnetic particles can be retained e.g. in the loading chamber.

The purified, eluted target nucleic acid that is retained by the collection matrix can be easily removed from the device using e.g. a pipette. According to one embodiment, the used device comprises a loading chamber, at least one collection chamber and at least one separation matrix in-between, wherein the loading chamber is separated from the cathode by the closing matrix and wherein the collection chamber is separated from the anode by the collection matrix. The method may comprise placing the solid phase with the bound target nucleic acid into the loading chamber of the device through an opening in the device wherein the target nucleic acid is eluted in the running solution;

applying an electric field either prior to or after elution, wherein the target nucleic acid migrates according to its charge in the electric field, passes through the separation matrix and is retained at the collection matrix;

optionally reversing the electric field; and collecting the purified target nucleic acid from the collection chamber through an opening in the device.

According to one embodiment, the solid phase with the bound target nucleic acid is separated from the remaining sample and is transferred to the device for further purification and elution of the target nucleic acid without performing one or more washing steps in advance.

According to a further embodiment, the target nucleic acid is placed into the passage of the device as part of an eluate. In this embodiment, the target nucleic acid is isolated according to conventional methods by binding it to a solid phase from which it is then also eluted. The eluate is then placed into the passage of the device. According to one embodiment, the eluate additionally comprises the solid phase that was used for isolating the target nucleic acid from the sample. E.g. the target nucleic acid that is bound to the solid phase, e.g. particles, is eluted from the solid phase by agitating the solid phase in the presence of a suitable elution liquid. The solid/liquid phase mixture (which may optionally comprise further additives such as e.g. RNase inhibitors, DNase etc.) is then placed into a passage of the device. As is demonstrated by the examples, this option is also feasible and reduces hands on time as the step of separating the eluate from the solid phase can be omitted. This embodiment is particularly suitable in order to ensure an efficient elution of the target nucleic acid, e.g. genomic DNA, from the solid phase. This embodiment can be used e.g. in conjunction with standard electrophoresis chambers.

The nucleic acid containing sample may be disrupted in order to release the nucleic acids. The term "disrupting" or "disruption" is used herein in broad sense and in particular encompasses the lysis of a sample. In a respective lysis step, nucleic acids are released from cells and/or can be freed from other sample components such as e.g. proteins, thereby rendering the nucleic acids accessible for isolation. Herein, it is referred to a respective disruption step also generally as lysis step, irrespective of whether nucleic acids are released from cells or whether the lysis is performed in order to release nucleic acids e.g. from proteins or other substances comprised in the sample. Different methods can be used in order to lyse a sample and suitable lysis methods are well-known in the prior art. Non-limiting examples are described in the following. The sample can be contacted for disruption, respectively lysis, with one or more lysing agents. These can be contained in a disruption reagent such as a lysis solution, e.g. a lysis buffer. RNA should be protected during lysis from degradation by nucleases. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. According to one embodiment, at least one chaotropic agent, such as preferably at least one chaotropic salt, is used for lysing and hence disrupting the sample. Suitable chaotropic agents and in particular suitable chaotropic salts are known to the skilled person and are also described herein. Using a chaotropic salt for lysis has the advantage that it allows to introduce a chaotropic salt which may additionally support or already establish suitable nucleic acid binding conditions. Such methods are likewise well-known in the prior art.

For binding a target nucleic acid (e.g. DNA and/or RNA) to a solid phase, methods known in the prior art may be used. Examples of suitable isolation methods include but are not limited to silica-based purification methods, magnetic particle-based purification methods, chromatography based purification procedures, anion-exchange chromatography (using anion-exchange surfaces, such as columns or magnetic particles) and combinations thereof. The target nucleic acid such as DNA and/or RNA is isolated from the optionally disrupted sample by binding the nucleic acid to a solid phase using appropriate binding conditions. Suitable binding conditions are known to the skilled person. The solid phase may e.g. provide a silica binding surface or may carry anion exchange functional groups which can bind the nucleic acid of interest. Non-limiting examples of suitable solid phases and binding conditions are also described herein. A preferred embodiment uses magnetic particles as solid phase, in particular magnetic particles with a silicon containing surface.

According to one embodiment, disruption of the sample involves the use of a chaotropic agent, preferably a chaotropic salt in order to release the target biomolecule, e.g. a target nucleic acid. The chaotropic salt can be comprised in the lysis mixture, which contains the sample, in a concentration selected from the group consisting of 0.1 M to saturation, 0.5M to 5M, 0.75 M to 4.5M and 1M to 4.25M. Chaotropic salts include but are not limited to guanidinium salts such as guanidinium hydrochloride, guanidinium thiocyanate (or guanidinium isothiocyanate (GITC)) or chaotropic salts comprising thiocyanate, iodide, perchlorate, trichloroacetate or trifluroacetate and the like. Such chaotropic salts can be provided e.g. as sodium or potassium salts. Urea may also be used. One or more other additives can also be added for lysis such as detergents, chelating agents, nuclease inhibitors, in particular RNase inhibitors or DNase inhibitors and the like. The disrupted sample may also optionally be further processed prior to the actual nucleic acid binding step. For example, the lysate can be homogenized; homogenization may also occur during the disruption/lysis process itself. Furthermore, the lysate can be cleared in order to remove cell debris. Lysis can also involve a proteolytic digest using a proteolytic enzyme. As is demonstrated by the examples, in embodiments, the lysate is directly applied to the passage of the device, e.g. to a loading chamber.

According to one embodiment, the target nucleic acid is bound to a solid phase in the presence of a salt, e.g. a chaotropic salt, wherein the solid phase provides a silicon containing surface. It is well-known that binding of the target nucleic acid to a solid phase can be enhanced by including a salt, preferably a chaotropic salt, in the binding mixture. Suitable conditions for binding nucleic acids to such a solid phase in the presence of a salt, in particular a chaotropic salt, are well-known to the skilled person. Non-limiting embodiments are also described herein.

The binding mixture may comprise one or more salts in a concentration which lies in a range of 0.1M up to the saturation limit to achieve or enhance binding of the target nucleic acid to the solid phase. The concentration may be selected from 0.1 M to saturation, 0.5M to 5M, 0.75 M to 4.5M and 1M to 4.25M. A higher concentration of a salt, in particular a chaotropic salt, can be favourable to ensure a good nucleic acid yield.

Binding of the target nucleic acid to the solid phase may be assisted by a suitable water-miscible organic solvent such as an alcohol. It may be a branched or unbranched aliphatic alcohol with 1 to 5 carbon atoms and may be selected from methanol, ethanol, propanol, isopropanol and butanol and mixtures thereof. Preferably, isopropanol and/or ethanol is used. Alternatively, a non-alcoholic, water miscible organic solvent such as acetone, THF, DMSO or the like can be used to assist binding. Such methods are well-known in the art. Suitable concentration ranges for the water-miscible organic solvent in the binding mixture, if used, include but are not limited to $\geq 10\%$) to $\leq 80\%$ (v/v), $\geq 15\%$ (v/v) to $\leq 75\%$ (v/v), $\geq 20\%$ (v/v) to $\leq 70\%$ (v/v) and $\geq 25\%$ (v/v) to $\leq 65\%$ (v/v). These concentration ranges are particularly preferred for an alcohol, such as ethanol or isopropanol.

Solid phases suitable for nucleic acid binding are known to the skilled person; exemplary suitable nucleic acid binding solid phases are described herein. As solid phase, a variety of materials capable of binding nucleic acids under appropriate conditions can be used. Any solid phase can be used for binding the nucleic acids. When the target nucleic acid is introduced into the passage of the device while being bound to a solid phase, the used solid phase allows release of the bound nucleic acids under the conditions that are provided by the running solution, optionally assisted by heating, shaking and/or the electric field that is applied for electrophoresis. A silica material is particularly preferred. Exemplary solid phases that can be used in conjunction with the present invention include, but are not limited to, compounds comprising silicon, including but not limited to, silica materials such as silica particles, silica fibres, glass fibres, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; minerals, zirconia; alumina; polymeric supports, organic polymers, diethylaminoethyl- and triethylaminoethyl-derivatized supports, hydrophobic chromatography resins and the like. The term solid phase is not intended to imply any limitation regarding its form or design. Thus, the term solid phase encompasses appropriate materials that are porous or non-porous, permeable or impermeable, including but not limited to membranes, filters, sheets, particles, magnetic particles, beads, powders, fibers and the like. According to one embodiment, the surface of the solid phase such as e.g. a silica solid phase is not modified and is, e.g., not modified with functional groups. Particularly preferred is the use of silicon containing materials such as silica and polysilicic acid materials, borosilicates, silicates and anorganic glasses as solid phase. Here, the solid phase preferably provides a silica surface for interaction with the nucleic acid which may be bound by precipitation and/or adsorption. The term "silica surface" as used herein includes surfaces comprising or consisting of silicon dioxide and/or other silicon oxides, diatomaceous earth, silica silanes, glass, zeolithe, bentonite, alkylsilica, aluminum silicate and borosilicate. The silica surface is preferably unmodified. Therefore, the surface is not modified with nucleic acid binding ligands or other nucleic acid binding groups. According to one embodiment, the silica surface does not comprise any functional groups besides its silanol groups or other oxidized forms of silicon, like oxides. Exemplary solid phases that can be used in conjunction with the present invention include, but are not limited to, solid phases comprising a silica surface, including but not limited to, silica particles, silica fibres, glass materials such as e.g. glass powder, glass fibres, glass particles or controlled pore glass, silicon dioxide, glass or silica in particulate form such as powder, beads or frits.

According to the present invention, the use of particles, in particular magnetic particles, is preferred as such particles can be easily transferred into the device. Silica based nucleic acid isolation methods are broadly used in the prior art for isolating nucleic acids such as DNA and/or RNA and work particularly well if the binding mixture contains at least one salt, preferably a chaotropic salt and optionally an alcohol. According to one embodiment, silica particles are used that may have the form of beads. Preferably, said particles have a size of about 0.02 to 30 µm, more preferred 0.05 to 15 µm and most preferred of 0.1 to 10 µm. To ease the processing of the nucleic acid binding solid phase, preferably magnetic silica particles may be used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Further suitable silica particles are also known from the prior art and are e.g. described in WO 98/31840, WO 98/31461, EP 1 260 595, WO 96/41811 and EP 0 343 934 and also include for example magnetic silica glass particles. The use of magnetic particles is convenient, because the magnetic particles including the bound target nucleic acid can be processed easily by the aid of a magnetic field, e.g. by using a permanent magnet. This embodiment is compatible with established robotic systems capable of processing magnetic particles and also manual tools exist for processing magnetic particles. According to one embodiment, a device comprising at least one retractable magnet covered by an inert polymer that does not adsorb or retain any biological molecules or magnetic particles for transferring the nucleic acid-binding support material, e.g. a Pick-Pen® Magnet.

The above described nucleic acid binding solid phases are generally suitable for binding DNA and/or RNA depending on the used binding conditions as is known to the skilled person. Optionally, one or more washing steps can be performed after the target nucleic acid was bound to the solid phase. Suitable washing buffers are described in the literature and well-known to those skilled in the art. However, preferably, no washing step is performed prior to placing the target nucleic acid into the passage of the device. This avoids extra handling steps.

As is demonstrated by the examples, the method allows to purify a target nucleic acid such as DNA and RNA from various biological samples. In addition, it is also possible to separate a target nucleic acid, in particular DNA, according to its conformation. E.g. as is demonstrated by the examples, the present method allows easy separation of supercoiled from linear plasmid DNA. The method also allows to isolate nucleic acids according to their size, e.g. using a collection matrix having an appropriate MWCO. If the size of the target nucleic acid is, for example, very short, two or more collection matrices can be used, wherein the pore size of the matrices decreases. Large nucleic acids can be retained, for example, by a first matrix, the smaller target nucleic acid can pass this matrix. The smaller target nucleic acid can then be retained, for example, by a second or third collection matrix with smaller pore size. Another way to collect nucleic acids of different sizes using the method is the time of electrophoresis. If the electrophoresis is short, smaller nucleic acid fragments are collected at the collection matrix, since the larger nucleic acids have not yet migrated through the whole electric field.

According to one embodiment, RNA is purified as target nucleic acid. It was found that it is challenging to use a method that is based on electrophoresis for purifying RNA. RNA is a sensitive target molecule which is prone to degradation by RNases. RNA is commonly isolated by binding the RNA to the solid phase in presence of a high concentration of a salt, such as a denaturing chaotropic salt. This inhibits RNases which can be present e.g. in the sample from which the RNA is isolated. There is also a risk to introduce RNases during handling. When the solid support with the bound RNA is placed into the electrophoretic device and comes in contact with the running solution, a dilution effect occurs which can reactivate RNases that are co-transferred with the solid phase, e.g. with sample residuals. This risk in particular exists if washing steps are omitted after separating the solid phase with the bound target nucleic acid from the sample to reduce handling steps. The presence of RNases in the loading chamber can lead to destruction of RNA so that no or only degraded RNA is recovered. In order to prevent that RNA is attacked by RNases during the electrophoresis separation process, different advantageous embodiments are described herein.

According to one embodiment, the RNA is contacted with one or more RNase inhibitors in the loading chamber. The RNase inhibitor can be preloaded in the loading chamber, or the RNA, optionally while being bound to a solid phase, can be contacted with a RNase inhibitor prior to placing it in the loading chamber. Non limiting examples include RNasin®, vanadyl complexes, antibodies and the like. The used RNase inhibitor is preferably not a salt and is compatible with the electric field based separation process. As soon as the RNA is eluted and the electric field is applied, the RNA migrates to the separation matrix and is collected in the collection chamber. RNases which might have been co-transferred together with the bound RNA into the device are retained in the loading chamber and e.g. migrate to the cathode.

It was moreover found that the isolation of RNA using the method of the invention can be significantly improved with respect to yield and quality, when introducing the RNA to the passage of the device while being bound to a solid phase, such as e.g. particles, preferably magnetic particles. The solid phase with the bound RNA is present in the loading chamber of the device in a liquid medium which comprises at least one water-miscible organic solvent. The solid phase with the bound RNA can either be contacted with said liquid medium prior to loading to the device and/or the liquid medium can be present in the loading chamber before the solid phase with the bound target nucleic acid is added. The RNA remains bound to the solid phase in said liquid medium, thereby preventing an early release of the RNA from the solid phase. This protects the RNA from coming into substantial contact with RNases present in the loading chamber. The liquid medium prevents the RNA from free diffusion in the loading chamber and therefore, prevents that the RNA is an easy target for RNases. The running solution dilutes the liquid medium comprised in the loading chamber over time when the electric field is applied resulting in elution of the bound RNA. E.g. after applying the electric field liquid currents can be induced in the passage of the device. This results in a liquid exchange between the loading chamber and the surrounding, which comprises the running solution. The running solution dilutes the liquid medium and generates elution conditions for the target nucleic acid. As soon as the RNA is eluted it follows the electric field lines as other charged molecules such as RNases do. RNases, which are basic proteins with a positive charge, migrate towards the cathode while RNA migrates towards the anode. Without wishing to be bound in theory, it is believed that RNAses that were co-transferred e.g. with sample residuals start to migrate essentially directly to the cathode when the electric field is applied. The bound RNA, however, can only migrate to the anode upon elution which occurs delayed due to the liquid medium which first must become diluted with running solution to create elution conditions. Therefore, there is no free diffusion of the RNA and RNases in the loading chamber when the electric field is applied which prevents the contact between RNases and RNA. The eluted target nucleic acid migrates according to its charge in the electric field through the optionally present separation matrix towards the anode and is retained by the collection matrix where it can be collected. As is demonstrated by the examples, this set-up effectively prevents a degradation of RNA. It is believed that the delayed elution of the RNA that is achieved with the liquid medium which comprises the water-miscible organic solvent as taught herein effectively prevents or reduces the contact between RNases and RNA. This embodiment is cost-effective as it does not require expensive compounds for protecting RNA such as RNase inhibitors. Thereby, an improved method for the fast and simple isolation of RNA from biological samples is provided. In this embodiment, the method preferably comprises (a) binding RNA to a solid phase;
(b) placing the solid phase with the bound RNA into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the RNA remains bound to the solid phase in said liquid medium;
(c) generating an electric field between a cathode and an anode and using a running solution that conducts the electric current, wherein the running solution dilutes the liquid medium comprised in the loading chamber resulting in elution of the bound RNA, and wherein the eluted RNA migrates according to its charge in the electric field and is retained by the collection matrix;
(d) collecting the purified RNA.

Step (a) of this embodiment may comprise optionally lysing the sample and binding the target nucleic acid to the solid phase in the presence of a salt, wherein binding is optionally assisted by at least one water-miscible organic solvent. Suitable methods for lysing a biological sample and binding the RNA to a solid support are known to the skilled person and suitable methods involving e.g. the use of a chaotropic salt are also described herein.

The organic solvent comprised in the liquid medium can be a water-miscible organic solvent, preferably selected from aprotic polar solvents and protic solvents. Also combinations of solvents may be used as water-miscible organic solvent for the purpose of the invention. The water-miscible organic solvent may have an inhibitory effect on a RNA degrading enzyme, e.g. RNase, e.g. by exhibiting protein denaturing properties. According to a preferred embodiment, the organic solvent is a protic solvent. Polar protic solvents that can be used include linear or branched C1-C5 alcohols. Water-miscible aliphatic C1-C5 alcohols such as isopropanol and ethanol are preferred and can be used as organic solvent. Also methanol is an alcohol miscible in water.

According to one embodiment, the water-miscible organic solvent is an aprotic polar solvent. Examples of such organic solvents include but are not limited to sulfoxides such as dimethylsulfoxide (DMSO), ketones such as acetone, nitriles such as acetonitrile, cyclic ethers such as tetrahydrofurane (THF) and 1,4 dioxane, lactams such as 1-methyl-2-pyrolidone (NMP) and tertiary carboxylic acid amides such as dimethyl-formamide (DMF). Such aprotic polar solvents are miscible in water. Thus, the aprotic polar solvent may be selected from sulfoxides, ketones, nitriles, cyclic or aliphatic ethers, lactames and tertiary carboxylic acid amides and preferably is selected from dimethylsulfoxide (DMSO), acetone, acetonitrile, tetrahydrofuran (THF), dioxane, respectively 1,4 dioxane, 1-methyl-2-pyrolidone (NMP) and dimethyl-formamide (DMF). Further examples include acetylacetone, diethylketone, methylethylketone, methylpropylketone, isobutylmethylketone, gamma-butyrolactone, gamma-valerolactone and propylene carbonate. The water-miscible aprotic polar solvent may be selected from the group consisting of acetone, acetonitrile, dimethyl sulfoxide (DMSO), tetrahydrofuran (THF), dioxane, and dimethylformamide (DMF), or combinations thereof. According to one embodiment, the water-miscible organic solvent is a non-alcoholic organic solvent. Examples were already mentioned above. Examples of such non-alcoholic organic solvents are aliphatic ethers, aliphatic esters, and aliphatic ketones. It is preferred that the aliphatic ethers, aliphatic esters, and aliphatic ketones comprise 2 to 10 carbon atoms. The aliphatic ether can for example be selected from the group consisting of ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran and 1,4-dioxane, or a combination thereof. The aliphatic ester can for example be selected from the group consisting of propylene glycol monomethyl ether acetate and ethyl lactate, or a combination thereof. The aliphatic ketone can for example be selected from the group consisting of acetone, hydroxyacetone, and methyl ketone, or a combination thereof. The organic solvent can be a water-miscible, non-acidic organic solvent as disclosed in U.S. Pat. No. 7,329,491 B1.

The liquid medium used in this embodiment preferably comprises the at least one water-miscible organic solvent in a concentration selected from 25% to 95% (v/v), 30% to 90% (v/v) and more preferably 35% to 85% (v/v), such as 40% to 80% (v/v). Also two or more water-miscible organic solvents can be present in the liquid medium. In this case, the indicated concentrations preferably refer to the total concentration of the contained water-miscible organic solvents.

The liquid medium is capable of conducting the electric current. It is preferably an aqueous medium. It may optionally comprise a buffering agent. E.g. buffers like MOPS, Tris, TAE, TE and TBE can be used. Generally, buffers used in electrophoresis can be used which are supplemented with a water-miscible organic solvent to provide the liquid medium. Further suitable buffers are also described herein and are known to the skilled person. A buffering agent may be comprised in a concentration of at least 0.5 mM, at least 2 mM or at least 5 mM. Ranges include 0.5 mM to 100 mM, 1 mM to 50 mM, 1.5 mM to 25 mM and 2 mM to 10 mM. A suitable concentration can be determined by the skilled person. The aqueous medium used as liquid medium may also comprise a salt, e.g. an alkali metal salt such as a halide, e.g. a chloride or an acetate, citrate, or phosphate. The salt may be comprised in a concentration from 100 mM to 1 mM, 75 mM to 5 mM, or 50 mM to 10 mM. The liquid medium may also comprise a chelating agent like EDTA or EGTA. The pH of the liquid medium may lie in a range selected from 6 to 9, 6.5 to 8.5 and 6.75 to 8. The pH also depends on the target nucleic acid and suitable pH values for processing target nucleic acids such as DNA and RNA are known to the skilled person.

According to one embodiment, the liquid medium is present in the loading chamber before the solid phase with the bound RNA is added. The loading chamber is prefilled with the liquid medium. The remaining part of the passage of the device may be pre-filled with running solution. The running solution may, however, also be introduced after the solid phase with the bound RNA was placed in the loading chamber. According to one embodiment, the solid phase with the bound RNA is contacted with the liquid medium outside the device. The liquid medium comprising the solid phase with the bound RNA is then placed into the loading chamber of the device. Thereby it is also achieved that the solid phase with the bound RNA is present in the loading chamber in the liquid medium which prevents, respectively delays elution of the RNA when the electric field is applied.

Suitable methods for lysing a biological sample and binding the RNA to a solid support are known to the skilled person and suitable methods involving e.g. the use of a chaotropic salt are also described herein. This embodiment for isolating RNA as target molecule may comprise:

(a) lysing the biological sample in the presence of at least one chaotropic salt and binding RNA to particles providing a silicon containing surface, wherein binding occurs in the presence of the at least one chaotropic salt and optionally at least one water-miscible organic solvent, (b) placing the solid phase with the bound RNA into a loading chamber of a device, wherein the device comprises a passage which comprises the loading chamber at one end, a liquid permeable separation matrix adjacent to the loading chamber and a liquid permeable collection matrix at the other end and wherein the solid phase with the bound RNA is present in the loading chamber in an aqueous liquid medium comprising at least one water-miscible organic solvent in a concentration that lies in the range of 30% to 90% (v/v) and wherein the RNA remains bound to the solid phase in said aqueous medium;

(c) generating an electric field between a cathode and an anode and using a running solution that conducts the electric current, wherein the running solution dilutes the aqueous liquid medium in the loading chamber resulting in elution of the bound RNA upon dilution of the aqueous liquid medium, and wherein the eluted RNA migrates according to its charge in the electric field through the separation matrix and is retained by the collection matrix;

(d) optionally reversing the electric field and collecting the purified RNA.

The embodiment wherein a liquid medium comprising a water-miscible organic solvent is used to delay elution of the bound target nucleic acid, preferably RNA, is described in further detail in European patent application EP 15 170 167.9 "Electrophoresis assisted method for purifying a target nucleic acid using a delayed elution approach", which was filed on the same day as the present application and which content is herewith incorporated by reference in its entirety.

According to one embodiment, a DNase is added when isolating RNA, e.g. to the loading chamber or the collection chamber. The DNase may also be included in the liquid medium.

The purified target nucleic acid can be used or analyzed e.g. to identify, detect, screen for, monitor or exclude a disease or other characteristic. The analytical methods will depend on the target nucleic acid of interest and include but are not limited to amplification technologies, polymerase chain reaction (PCR), mass spectrometry, hybridization assays, RNA or DNA sequencing, next generation sequencing, restriction analysis, reverse transcription, or any combination thereof. According to one embodiment, the purified target nucleic acid is used in an amplification reaction and the running solution is thus compatible with such use.

Device

According to a second aspect, the present invention also provides a device suitable to be placed in an electrophoresis chamber for use in a method for purifying a charged target molecule, preferably a nucleic acid, by electrophoresis, the device comprising a first end region and a second end region and a passage between the first end region and the second end region wherein the passage is closed at the second end region by a liquid permeable collection matrix. It can be used in the method according to the first aspect in order to purify a charged target molecule, preferably a negatively charged target molecule such as a nucleic acid. Details of the device were also already described in conjunction with the method according to the first aspect and it is referred to the respective disclosure. In operation, the device comprises a running solution and an electric field is generated to impose a force on the charged target molecule. The device is preferably a cartridge. All embodiments described herein referring to the device in general also specifically apply to the embodiment, wherein the device is a cartridge.

The device, respectively the cartridge, can be of any geometrical shape. In a preferred embodiment, it is an elongated device that generally extends along a longitudinal axis. The device preferably comprises openings at both ends, which preferably oppose each other, wherein one end opening is closed by the collection matrix and the other end opening is preferably closed by a liquid permeable closing matrix. When used in an electrophoresis chamber during electrophoresis, the device according to the invention can be used in such a way and orientation that solids and/or fluids inside the passage can be made to travel towards one or the other electrode that will typically be provided for generating an electric field in an electrophoresis chamber. If the cartridge is designed to generally extend along a longitudinal axis, the passage can in a preferred embodiment also be designed to generally extend along this longitudinal axis, which can facilitate the movement of the solids and/or fluids in the passage.

The passage of the device can be directly or indirectly in fluid communication with the exterior of the device via the closing matrix and the collection matrix, such that a liquid can enter and exit the device through the closing matrix and the collection matrix.

Preferably, the device does not comprise any electrodes for generating an electric field. It is preferred that the device, respectively cartridge, is placed in an electrophoresis chamber and that the electrodes for providing the electric field in the electrophoresis chamber are part of the electrophoresis chamber. This allows to design the cartridge as consumable that can be used in combination with an electrophoresis chamber and is cost-efficient. Devices which comprise the electrodes for generating the electric field as described in the prior art have disadvantages. If such device is designed small, what is convenient with respect to handling and costs, there is a risk that the pH of the running solution is significantly lowered during operation of the system because there is not sufficient running buffer to buffer the reduction in pH that occurs when the electric field is applied. Nucleic acids can be damaged at a low, acidic pH values. If, however, the device is designed large to allow the reception of a larger volume of running solution, this has the drawback that the device is expensive and inconvenient to handle. These issues are avoided with a device of the present invention which is free of electrodes. The device can be designed small and due to the omission of the electrodes also simple which reduces the manufacturing costs. Circuit points and other elements are not required. Because the device is placed in an electrophoresis chamber, a larger reservoir is provided within the electrophoresis chamber for the running solution, which preferably is a running buffer. This larger amount of running solution prevents a rapid or significant reduction of the pH value during operation of the system. As described herein, the device is preferably a disposable cartridge for single use. The device can be loaded with the charged target molecule without being placed in the electrophoresis chamber in which the electrodes are provided. The device may be prepared, handled and processed before insertion of the device into the chamber comprising the electrodes. However, it may also be placed inside the electrophoresis chamber prior to adding the target molecule to be purified. Advantageously, the device can be prepared and handled independently from the electrophoresis chamber.

The device can be provided as a discrete and thus independent body separate from the electrophoresis chamber, also referred to herein as unit. The term "unit" or "discrete body" does not define that the device is formed from a single piece. Instead, it can be formed or assembled from multiple parts or from a single piece as is demonstrated by the examples. Thus, the device can be provided as a one piece unit or as a multi-part unit. Moreover, the device can be provided as part of a device assembly which comprises a plurality of identical devices according to the second aspect of the invention. This allows processing several nucleic acid containing materials/samples in parallel. The devices can be arranged such in the assembly, that they can be loaded with a multi-pipette which can also be used for removal of the eluted nucleic acids or a device with multi retractable magnets as described above, e.g. a PickPen® 8M.

In a preferred embodiment, the device has a basic body, preferably a one-piece basic body. The one-piece basic body can be obtained by molding or 3D printing, for example. In a preferred embodiment, the passage is arranged inside the basic body. The basic body may comprise one or more apertures, preferably located at the top, to allow entry and removal of the charged target molecule.

Further, the device can in embodiments be made without parts or elements which have to move during operation, i.e. when applying the electric field. Moveable parts can be omitted which is a further advantage over prior art systems.

The passage formed in the device can comprise a closing matrix, a separation matrix and the collection matrix in the afore-mentioned order. Details of these elements were already described above in conjunction with the method according to the first aspect and it is referred to the respective disclosure which also applies here.

The device is preferably provided as a replaceable unit which lacks electrodes and can be placed in an electrophoresis chamber for applying an electric field between two electrodes when the electrophoresis chamber is filled with running buffer.

The device can be prepared or pre-filled with the closing matrix, the separation matrix and the collection matrix. Closing matrix, separation matrix and the collection matrix can be fixed relative to each other. The closing matrix is positioned in the region of one end of the device and the collection matrix is positioned in the region of another end of the device (also referred to as rear end and front end). The closing matrix and the collection matrix form a barrier for the charged target molecule in the respective ends of the passage. This prevents a loss of target molecule. Closing matrix and collection matrix preferably terminate the passage with regard to the fluidic transfer into and out of the device and therefore control the liquid flow into and out of the passage.

The passage may be formed between two openings of the device. Preferably, the device is elongated between the two openings wherein the rear end opening is closed by the closing matrix and the front end is closed by the collection matrix. The device is preferably a hollow elongated tube. Along the longitudinal axis of the device an electric field can be applied. It crosses the closing matrix, the separation matrix (if present) and the collection matrix when the passage of the device comprises the running solution which conducts the electric current. Preferably, the device comprises at least when placed in the electrophoresis chamber for operation a longitudinal axis which extends from one of the openings through the closing matrix, the separation matrix and the collection matrix to the other opening, the longitudinal axis being a straight line. As described herein, the electrodes comprised in the electrophoresis chamber are in one embodiment also an axial extension of the device. In case the body of the device is tapered, e.g. to allow a concentration of the nucleic acid in the running solution at the collection matrix, this can be achieved e.g. by furnishing the device with one or more supporting bases to level the device decline and to position the device. In a further embodiment, only the inner cross section respectively diameter of the passage is tapered, while the body and hence the outer cross section of the device is substantially the same as it is also shown in the figures. In a preferred embodiment the closing matrix, the loading chamber, the separation matrix, the collection chamber and the collection matrix are arranged on the same axis.

The closing matrix and collection matrix can be positioned at the openings of the cartridge which are opposed to each other. In a preferred embodiment, the two openings of the cartridge—positioned in a row near or at both ends—can be connected by a straight line which can be identical to or parallel to the longitudinal axis of the cartridge. By an arrangement along a straight line a small voltage can be applied to the electrode which is important because the voltage is proportional to the input power. Further openings, also referred to herein as apertures, can be formed in the device in order to simplify loading of the sample and removal of the purified target nucleic acid. They can especially extend to a connection line between the two end openings of the device, preferably vertical.

Preferably, the device comprises a loading chamber that is formed at least in part by the closing matrix and the separation matrix and comprises a collection chamber that is formed at least in part by the separation matrix and the collection matrix. The target molecule containing sample material is introduced into the loading chamber. During operation, the target molecule migrates from the loading chamber through the separation matrix into the collection chamber wherein the target molecule is retained by the collection matrix. The purified target molecule can then be conveniently removed from the collection chamber. The loading chamber preferably comprises at least one opening in order to facilitate loading of the target molecule. The collection chamber may comprise at least one opening in order to simplify removal of the target molecule. These openings are particularly advantageous if the device is provided as hollow body, such as an elongated tube. The openings are at the top of the device and may have a "collar" to balance volume variations due to temperature or flow effects.

The device can be designed as tube-shaped elongated body. This allows a simple construction of the device. The term "tube" according to the invention encompasses a hollow cylinder of any outer contour and any inner contour. Preferably, the inner contour of the tube-shaped elongated body is shaped like a circle in at least one section of the tube-shaped elongated body in the direction of the longitudinal axis. Most preferred the inner contour is shaped like a circle over the whole length of the body, wherein the diameter of the inner contour over the length of the device can vary as it is shown in the examples. Preferably, the outer contour of the tube-shaped elongated body is shaped like a circle in at least one section of the tube-shaped elongated body in the direction of the longitudinal axis. Most preferred the outer contour is shaped like a circle over the whole length of the body. The diameter of the outer contour of the device can vary over the longitudinal axis of the device.

In one preferred embodiment, the cross section of the loading chamber is greater than the cross section of the separation matrix. The cross section of the separation matrix can be greater than the cross section of the collection matrix. The passage may be shaped in a tapered manner reducing the cross section along the passage from the loading chamber to the separation matrix and optionally also to the collection matrix. This geometry simplifies the assembly of the elements of the cartridge. It may also support the purpose of the separation matrix of filtering contaminating compounds and may support the concentration of the nucleic acids at the collection matrix. The cross section of the loading chamber can be in the range between about 5 mm to about 15 mm, preferred between about 6 mm to about 10 mm. The cross section of the separation section in which the separation matrix can be positioned can be in the range between about 3 mm to about 10 mm, preferred between about 4 mm to about 8 mm. The cross section is preferably determined at the narrowest point. Where the device is a tube and the cross section is substantially round, the indicated length of the cross section refers to the diameter. According to one embodiment, the device has at one end, namely the end region where the collection chamber is located, at least a portion of reduced cross sectional area. According to one embodiment, the cross section of the collection chamber is smaller than the cross section of the separation matrix. The cross section of the collection chamber is according to one embodiment smaller than the cross section of the loading chamber. According to a preferred embodiment, the volume that can be received by the collection chamber is smaller than the volume that can be received by the loading chamber. The volume of the collection chamber can be 70% or less, 50% or less, 40% or less or 30% or less than the volume of the loading chamber.

The device is preferably a hollow construction. The device may comprise a hollow elongated casing, preferably tube-shaped as described above, which comprises the passage and wherein the two ends of the device are opposed to each other. The casing of elongated form can be circular, rectangular or in any other appropriate form. Preferably, it is substantially circular at least over 50%, more preferred over 70% of its length. The closing matrix, separation matrix and collection matrix extend into the passage, preferably across the entire width or cross section of the passage. By providing a tight fit between the casing of the device and the matrixes, applying the sample to the loading chamber will not result in that the sample accidently exits the device or bypasses the separation matrix. Instead, the sample is forced to pass through the separation matrix upon application of an electric field. As it is also shown in the cross sections in FIGS. 1 to 7, the device is hollow and may incorporate within the formed passage a closing matrix and a separation matrix which together with the casing form a loading chamber for the nucleic acid containing material. A collection chamber may be formed by the separation matrix and the closing matrix together with the casing.

The device may comprise a supporting base which may be formed as a pedestal. The supporting base can be adapted to form contacting points that preferably lie substantially in a plane. By providing the contacting points substantially in a plane, it is possible that the device can be placed conveniently in the electrophoresis chamber. Additional structural elements are not required. This is also advantageous e.g. where the device is shaped in a tapered manner as the supporting base can compensate the tapering. Alternatively, it is also feasible that a mounting is provided in the electrophoresis chamber that compensates the tapering and ensures that the longitudinal axis of the device extends to and matches the electrodes.

The supporting base can be adapted with regard to the inclination and/or orientation of the device to the bottom of the electrophoresis chamber or a structural element on the bottom of the electrophoresis chamber. The supporting base can be detachably or undetachably attached to the device. The supporting base can also be formed together with the device as a single piece. The device can also be hinged into one or more mountings to properly place the device into the electrophoresis chamber.

The device may comprise a handle. The handle may be formed as a fin or rib extending from the device. The handle may comprise at least one section which extends substantially perpendicular to the outer surface of the device. The handle allows for an easy manner to carry the device as well as to place the device into the electrophoresis chamber. The handle can be detachably or undetachably attached to the device. The handle can also be formed together with the device as a single piece. The handle can be used as a positioning or aligning element such that the handle can be positioned with regard to at least one reference point provided in or on the electrophoresis chamber which comprises the electrodes. In a preferred embodiment the electrodes can serve as reference points and the handle extending in the longitudinal axis of the device can be positioned such that the handle is aligned to the connecting line of the two electrodes.

In a preferred embodiment the length of the device is 1.25 cm to about 7 cm, preferred about 1.5 cm to about 6 cm, more preferred about 1.75 cm to 5 cm, and even more preferred about 2 cm to 4 cm, e.g. 2.5 cm to 3 cm. A small size simplifies the handling of the device and allows that the system can be operated with relatively high field strength.

The device may comprise the closing matrix, the separation matrix and/or the collection matrix as discrete bodies. Means can be provided to hold the closing matrix, the separation matrix and/or the collection matrix in place. According to one embodiment, the closing matrix and the separation matrix are provided in form of a single element also referred to as loading pad. Such device is e.g. described in the examples.

Suitable and preferred characteristics of the collection matrix were already described above in conjunction with the method of the present invention and it is referred to this disclosure which also applies here.

Suitable and preferred characteristics of the closing matrix were already described above in conjunction with the method of the present invention and it is referred to this disclosure which also applies here.

Suitable and preferred characteristics of the separation matrix were already described above in conjunction with the method according to the first aspect and it is referred to this disclosure which also applies here. A liquid such as the running solution is freely mobile within the passage between the closing matrix and the collection matrix. It is preferred that the separation matrix does not form a substantial barrier against induced flows, such as an electroosmotic flow. Such flow may go into the opposite direction than the charged target molecule migrates in the electric field as is shown in the examples. Depending on the choice of the matrixes, in particular the collection matrix, the induced flow may, however, also go into the same direction as was explained above. According to one embodiment, the separation matrix provides for maximized pressure equalization. As discussed above, it is preferred that the separation matrix is made of a porous material that achieves that result. Alternatively or additionally, at least one narrow channel can be provided in the separation matrix to allow pressure equalization within the device in the event of electroosmotic flow. These one or more channels are preferably located in the upper third, preferably upper quarter of the separation matrix.

Suitable and preferred combinations of collection matrix, closing matrix and/or separation matrix were also described above in conjunction with the method according to the first aspect and it is referred to the above disclosure.

In one embodiment the collection matrix is inserted into an opening at the end region of the device and held by a retainer. The closing matrix may be mounted the same fashion. The manufacture of such a device is simple and the possibility to use different collection matrixes arises and makes the device flexible regarding characteristics of the target nucleic acid (e.g. size or topoisomerism). In addition, it allows a reuse of the device body by inserting new matrixes after use.

In a preferred embodiment the separation matrix, the collection matrix and the closing matrix are adapted to each other to influence flow characteristics within the device and/or allow pressure equalization. An overflow of running buffer can thereby be prevented in the chambers. Suitable combinations of the collection matrix with the closing matrix and/or the separation matrix were already described above in conjunction with the method according to the first aspect and it is referred to the respective disclosure which also applies here. The described combinations allow to adapt the flow characteristics and allow e.g. to induce a flow in the passage of the device which can support the purification of the target molecule as it allows the separation of the target molecule according to its charge and charge density (flow-assisted sub-aspect) or allow to substantially suppress flows within the passage (electro-kinetic sub-aspect). According to one embodiment, the collection matrix and the closing matrix are adapted to each other with regard to porosity in order to prevent migration of the target nucleic acid into the direction of the cathode when the device is in use. According to one embodiment, the collection matrix and the closing matrix are those elements with the highest flow resistance and therefore control the entry and exit of liquid into and out of the cartridge. In order to suppress inner-tube flow effects, such as an electroosmotic flow induced by the collection matrix, in one embodiment a membrane having a small pore size is used as closing matrix. E.g. ultrafiltration membranes can be used as closing matrix and as collection matrix which both may have a MWCO in the range of 1 kDa to 500 kDA, 3 kDa to 300 kDa, 5 kDa to 200 kDa or 7 kDa to 100 kDa. Such ultrafiltration membranes are preferably used in combination with a separation matrix which has macropores in the micrometer range. According to a further embodiment, the closing matrix is a siliceous material having an average pore size that lies in the range of 0.1 µm to 100 µm, preferably selected from 0.5 µm to 10 µm, 0.75 µm to 7.5 µm, 0.75 µm to 5 µm and preferably 1 µm to 3.5 µm. It can be used in combination with an ultrafiltration membrane as collection matrix. Details were described above in conjunction with the method according to the first aspect and it is referred to that disclosure.

In a preferred embodiment at least one aperture (also referred to as opening herein) that extends parallel to the longitudinal axis of the passage is positioned in the region of the loading chamber. The loading chamber lies beneath this aperture. The aperture can be used for introducing the sample into the loading chamber of the device. This simplifies placing the material or eluate containing a target molecule, e.g. a solid phase with bound nucleic acid or a nucleic acid containing lysate, into the loading chamber. The material can be placed into the loading chamber through the aperture while the device is horizontally oriented with its longitudinal axis. According to one embodiment, the aperture also extends at least partially over the separation section to allow release of air to avoid air bubbles in the device after the device was flooded with running solution. Thus, this opening can also fulfill a venting function.

In a preferred embodiment at least one aperture which extends parallel to the longitudinal axis of the passage is positioned in the region of the collection chamber. The collection chamber lies beneath the aperture. The purified target molecule can be removed from the collection chamber and/or the collection matrix through this aperture. The target molecule can be introduced and removed from the device from above. According to one embodiment, the aperture also extends at least partially over the separation section to allow release of air to avoid air bubbles in the device after the device was flooded with running solution. Thus, this opening can also fulfill a venting function.

According to one embodiment, an aperture that extends parallel to the longitudinal axis of the passage is positioned in or in the region of the separation matrix and/or between the separation matrix and the loading chamber. The aperture can serve the purpose of a vent to allow release of air to avoid air bubbles in the device after flooding of the device with buffer. At least one additional vent opening may be formed.

Preferably, the at least one aperture for removing the purified target molecule, the at least one opening for release of air when flooding the device and/or the at least one aperture for loading the target molecule into the loading chamber extend in substantially the same direction. According to one embodiment, the apertures are located at the top of the device and are designed such that they are not covered with running solution when the device is placed into an electrophoresis chamber.

The apertures provided for entry and removal of the target molecule and/or venting can be smaller than the end openings of the passage. According to one embodiment, the aperture for entry of the target molecule is larger than the aperture for removing the target molecule.

According to one embodiment, at least one or all openings and apertures along the longitudinal axis of the passage are surrounded by a collar at the outer surface of the surface of the device. The collar can prevent entry of liquid (e.g. running solution) through the opening/aperture that are preferably located at the top of the device. The height of the device should be adapted to the electrophoresis chamber so that the running solution when filled in the electrophoresis chamber levels with the above outer surface of the device. As described herein, the device is flooded with the running solution to allow an electrophoresis assisted purification of the nucleic acid. Preferably, the running solution is below the at least one openings/apertures which extend transverse to the longitudinal axis of the passage and substantially perpendicular to the bottom of the chamber of the device. The device may also comprise means for closing and/or sealing the apertures to avoid leaking during operation.

According to one embodiment, the device comprises additionally at least two openings at opposed sides, wherein a connecting line between the at least two openings cuts the longitudinal axis of the device. The at least two openings can allow electric field based separation of charged molecules in a second or even a third dimension. In one embodiment, at least two openings with a connection line which is perpendicular to the longitudinal axis of the device allow electric field based separation in a second direction which is perpendicular to the electric field based separation along the longitudinal axis of the device.

The casing of the device, also referred to housing herein, can be molded in one or according to another embodiment in two or more parts which can be securely fasten together. According to one embodiment, the housing of the device is fastened together after the separation matrix and/or collection matrix were put in place. The collection matrix can also be incorporated in advance. According to one embodiment, the collection matrix is a matrix that is removably inserted into the device and thus can be exchanged. The function of the device can also be achieved if the device is made up of several parts, as long as the parts can be positioned to each other such, that the function of the device can be performed. The device can e.g. be assembled from an assembly set according to the fourth aspect of the invention. As discussed above, the device may also form a part of a larger assembly which comprises a plurality of identical devices according to the second aspect of the invention.

The casing of the device can be made of a plastics material, preferably polypropylene, polyethylene, polycarbonate, or silicone. The material of the casing is a liquid impervious solid material. The casing is preferably moldered from plastics material, e.g. by injection molding or 3D printing. At least the inner wall of the device/casing or the device as such has insulating properties.

The target molecule containing material that can be inserted into the device can be e.g. a liquid sample or a solid phase to which the target nucleic acid to be purified is bound or a suspension comprising a solid phase to which the target nucleic acid to be purified is bound. Suitable samples were described in conjunction with the method according to the first aspect and it is referred to the respective disclosure which also applies here. The sample can be a biological sample. Biological samples are usually processed for isolating the nucleic acids involving the use of salts, for example during lysis. With the device according to the invention, a lysate which comprises a high amount of salt can be subjected directly to the passage of the device when using e.g. the flow-assisted aspect of the invention as is demonstrated by the examples. The high ionic strength of the lysate does in these embodiments not disturb an electrophoretic field based separation. Moreover, one can subject a lysate comprising a low salt concentration to the device. For example, a lysate can be used that is obtained after mechanically destroying the sample and applying directly the lysed biological samples. Therefore, it is not required that the nucleic acids are first bound to the solid support. In particular, a low ionic strength sample can be directly subjected to the device for performing an electrophoretic separation. A liquid sample can be introduced e.g. into the loading chamber and/or can be applied to a loading pad in order to ensure a targeted application of the sample to the device. According to one embodiment, the nucleic acid to be purified is bound to a solid phase and the solid phase with the bound nucleic acid is placed into the device. Details were described above in conjunction with the method according to the first aspect and it is referred to the respective disclosure.

According to one embodiment, the device comprises a loading pad in the loading chamber, the loading pad being preferably spaced apart from the separation matrix. The loading pad can absorb the target molecule containing material, in particular a liquid nucleic acid containing sample, wherein this absorption can be assisted or induced by capillary action. It is preferably hydrophilic. The loading pad can be used in order to simplify the application of a liquid target molecule containing sample to the device. Because of its absorbing characteristics, it can basically suck up the liquid sample e.g. from the pipette. Therefore, the loading pad is able to generate a lateral flow. The sample can be sucked up by capillary forces. The loading pad can prevent that a liquid nucleic acid containing material distributes freely inside the device. In one embodiment, the loading pad also functions as closing matrix. The loading pad can be made from any bibulous, porous or fibrous material capable of adsorbing liquid rapidly. The porosity of the material can be unidirectional (i.e. with pores or fibres running wholly or predominantly parallel to an axis of the loading pad) or multidirectional (omnidirectional, so that the loading pad has an amorphous sponge-like structure). Porous plastic materials, such as polypropylene, polyethylene (preferably of very high molecular weight), polyvinylidene fluoride, ethylene vinylacetate, acrylonitrile and polyetrafluoro-ethylene can be used. The loading pad may also be made from paper or other cellulosic materials, such as nitro-cellulose. The loading pad can be shaped or extruded in a variety of lengths and cross sections appropriate in the context of the invention. According to one embodiment, the material of the loading pad is chosen such that it can be saturated with aqueous liquid within a matter of seconds. Preferably, the material remains robust when moist. Nucleic acids contained in the sample can permeate freely out of the loading pad, at least when the electric field is applied.

Further characteristics of the device are also described in conjunction with the method according to the first aspect and the figures and it is referred to the respective disclosure.

Use

In a third aspect, the present invention pertains to the use of the device according to the second aspect for purifying a charged target molecule, preferably a nucleic acid, using electrophoresis, wherein the device is placed in an electrophoresis chamber for electrophoresis and wherein the electrophoresis chamber comprises the electrodes for generating the electric field. In particular, the device is for use in the method according to the first aspect and it is referred to the above disclosure.

According to one embodiment, the electrophoresis chamber comprises discoid electrodes. The electrodes are placed or present in the electrophoresis chamber so that they are located near the end of the device when the device is placed in the electrophoresis chamber. Details were described above and it is referred to the respective disclosure.

Assembly Set

In a fourth aspect, an assembly set for a device for use in a method for separating a charged molecule acid by electrophoresis is provided, wherein the assembly set comprises at least two containers, each of the at least two containers having at least two openings, wherein the at least two containers are connectable to form a passage, one of the containers comprising a liquid-permeable separation matrix and/or a liquid-permeable collection matrix and the other container comprising a liquid permeable closing matrix. A device according to the second aspect can be assembled from the assembly set. Details of said device which preferably is a cartridge that lacks electrodes are described above and it is referred to the respective disclosure which also applies here. The assembly set can comprise all features, embodiments and arrangements described above in relationship with the device and it is referred to the above disclosure which also applies here. The containers can be connected by a plug-in connection in which the outer contour of one of the containers fits into the inner contour of the other container. The containers can be screwed together. The plug-in and/or screwing connection between the containers can be supported by an adhesive and/or a sealing element.

In one embodiment, the assembly set comprises three containers being connectable to form a passage comprising the separation matrix, the collection chamber and the collection matrix. One of the containers can comprise the loading chamber, wherein one of the remaining two containers can comprise the separation matrix and the other the collection chamber with the collection matrix.

Method

In a fifth aspect, a method for purifying a charged target molecule, preferably a nucleic acid, by electrophoresis is provided, comprising the step of inserting a device according to the second aspect or a device assembled from the assembly set according to the fourth aspect which lacks electrodes into an electrophoresis chamber which is prefilled or adapted to be filled with a running solution and which comprises electrodes for generating an electric field. Details of the device and the assembly set were described above and it is referred to the respective disclosure. In addition, suitable and preferred embodiments of the electrophoresis chamber were already described above in conjunction with the method according to the first aspect and it is referred to the respective disclosure.

System

In a sixth aspect, a system is provided comprising the device according to the second aspect or an assembly set for a device according to the fourth aspect and an electrophoresis chamber which comprises electrodes for generating the electric field. As described above, the electrodes are preferably adapted with regard to shape and/or size to the device. Details of the device and the electrophoresis chamber are described in detail herein and it is referred to the respective disclosure. As is also demonstrated by the examples, different electrophoresis systems can be used as electrophoresis chamber. Thus, different electrophoresis systems comprising electrodes for generating an electric field can be used as electrophoresis chamber in conjunction with the present invention.

According to a preferred embodiment, a tube-shaped device is used which lacks electrodes and corresponding discoid electrodes are provided in the electrophoresis chamber so that they are located near the ends of the tube-shaped device when the device is placed in the electrophoresis chamber. The electrodes preferably are an axial extension of the tube and have identical dimensions (diameter) to avoid unnecessary input of energy.

Also disclosed are the following items:

1. An electrophoresis assisted method for purifying a charged target molecule, comprising
   placing the target molecule to be purified into the passage of a device, wherein said passage is closed at one end by a liquid permeable collection matrix;
   generating an electric field between a cathode and an anode in a running solution that conducts the electric current to impose a force onto the target molecule comprised in the passage, wherein the collection matrix forms a barrier for the target molecule;
   collecting the purified target molecule.

2. Method according to item 1, wherein the target molecule has one or more of the following characteristics
   a) it is a negatively charged molecule;
   b) it is a biomolecule;
   c) it is a nucleic acid;
   d) it is DNA;
   e) it is RNA.

3. Method according to item 1 or 2, wherein the target molecule is separated from impurities according to its charge and/or its charge density.

4. The method according to one or more of items 1 to 3, wherein the collection matrix has one or more of the following characteristics
   i) it is hydrophilic;
   ii) it comprises or consists of a charged, polarizable and/or dielectric material, preferably a negatively charged, negatively polarizable and/or dielectric material;
   iii) it is capable of inducing a flow in the running solution comprised in the passage of the device;
   iii) it is porous;
   iv) it is a filter or membrane;
   v) it is an ultrafiltration membrane;
   vi) it has a MWCO that lies in the range selected from 1 kDa to 500 kDa, 3 kDa to 300 kDa, 5 kDa to 200 kDa, 7 kDa to 100 kDa and 10 kDa to 50 kDa;
   vii) it does not bind the target molecule under the conditions that are used for electrophoretic purification of the target molecule; and/or
   viii) it comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrat, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein preferably the collection matrix comprises or consists of a material selected from a cellulose material, PES, nylon and PVDF, more preferably it comprises or consists of PES, regenerated cellulose, or a cellulose acetate material.

5. The method according to item 4, wherein the collection matrix induces a flow in the running buffer comprised in the passage that is directed to the cathode and wherein the target molecule is retained in the passage by the applied electric field due to its charge and/or charge density and preferably migrates to the collection matrix and wherein optionally, the induced flow flushes impurities out of the passage.

6. The method according to item 5, wherein the flow within the passage is adjusted and/or compensated by the choice of one or more of parameters selected from the group consisting of the collection matrix material or combination of materials, the pore size of the collection matrix material and/or the applied electric field strength.

7. The method according to one or more of items 1 to 6, wherein the passage of the device is closed at the other end by a liquid permeable closing matrix.

8. The method according to item 7, wherein a flow in the running buffer comprised in the passage of the device that is directed to the cathode is adjusted and/or compensated by the choice the closing matrix material and/or the pore size of the closing matrix and one or more parameters selected from the group consisting of the collecting matrix material, the pore size of the collection matrix material and/or the applied electric field strength.

9. The method according to item 7 or 8, wherein the closing matrix has one or more of the following characteristics:
   i) it is hydrophilic;
   ii) it is porous;
   iii) it is a filter or membrane;
   iv) it is an ultrafiltration membrane, a microfiltration membrane or a deep bed filter;
   v) it is porous and optionally has a pore size selected from the range of 0.1 µm to 100 µm, 0.25 µm to 50 µm, 0.5 µm to 25 µm, 0.6 µm to 15 µm and 0.7 µm to 10 µm, preferably selected from 0.8 µm to 7.5 µm, 0.9 µm to 5 µm and 1 µm to 3 µm;
   vi) it has a MWCO that lies in the range selected from 1 to 500 kDa, 5 kDa to 300 kDa, 10 kDa to 200 kDa, 10 kDa to 100 kDa and 10 kDa to 50 kDa;
   vii) it has a pore size that is larger than the pore size of the collection matrix;
   viii) it has a pore size that lies in the same range as the pore size of the collection matrix wherein said range is between 1 kDa and 300 kDa, preferably 10 kDa and 100 kDa; and/or
   ix) it comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrat, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein preferably the closing matrix comprises or consists of a material selected from cellulose materials, polyethersulfone (PES), a mineral oxide, silicon containing materials, such as siliceous materials, more preferably it comprises or consists of regenerated cellulose (RC), a cellulose acetate material or a siliceous material, preferably made of silica and/or glass.

10. The method according to one or more of items 1 to 9, wherein the passage comprises a liquid permeable separation matrix and which optionally is characterized by one or more of the following characteristics:
   i) the separation matrix is a filter or membrane;
   ii) the separation matrix extends within the passage of the device over a length of 0.1 mm to 25 mm, 0.5 mm to 20 mm, 1 mm to 15 mm or 1.5 mm to 10 mm;
   iii) the separation matrix is porous;
   iv) the separation matrix is porous and has an average pore size that is smaller than the average size of a solid phase that is placed together with the target molecule to be purified into the passage of the device, wherein in case particles are used as solid phase the average pore size of the separation matrix is smaller than the average diameter of the particles;
   v) the separation matrix is hydrophilic;
   vi) the separation matrix comprises or consists of a material selected from cellulose materials, such as cellulose, regenerated cellulose (RC), cellulose esters, preferably selected from cellulose acetate materials such as cellulose acetate, cellulose diacetate and cellulose triacetate and cellulose nitrat, silicones, polyamides, such as nylon, polyamide urea, polyvinylidene fluoride (PVDF), mineral oxides, silicon containing materials, such as siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamid;
   vii) the separation matrix comprises or consists of a material selected from cellulose materials, PP, PE, nylon or PVDF, preferably it comprises or consists of cellulose acetate or PE and optionally is provided by a hydrophilic PE filter such as a PE frit; and/or
   viii) the passage is closed by a liquid permeable closing matrix and the liquid permeable separation matrix is placed between the closing matrix and the collection matrix.

11. The method according to one or more of items 1 or 10, wherein the passage of the device comprises a liquid permeable closing matrix, a liquid permeable separation matrix and a liquid permeable collection matrix and wherein the target molecule is placed between the closing matrix and the separation matrix, wherein upon application of the electric field the target molecule migrates through the separation matrix and is retained at the collection matrix.

12. The method according to one or more of items 7 to 11, wherein the device comprises an ultrafiltration membrane as closing matrix and comprises an ultrafiltration membrane as collection matrix.

13. The method according to item 12, wherein the ultrafiltration membranes that are used as closing matrix and as collection matrix have a MWCO in the range of 1 kDa to 300 kDa, 1 kDa to 200 kDa, 3 kDa to 100 kDa or 5 kDa to 50 kDa, wherein the MWCO of the closing matrix and the collection matrix can be the same or may differ from each other.

14. The method according to item 12 or 13, wherein the material of the ultrafiltration membranes that are used as closing matrix and as collection matrix is selected from CA, CTA, RC and PES and wherein the material of the closing matrix and the collection matrix can be the same or may differ from each other.

15. The method according to one or more of items 7 to 11, wherein the device comprises a porous closing matrix that is made of a siliceous material, preferably silica or glass, and wherein the closing matrix has a pore size that lies in the range of 0.5 µm to 10 µm, 0.75 µm to 7.5 µm, 0.75 µm to 5 µm and preferably 1 µm to 3.5 µm.

16. The method according to item 15, wherein the device comprises an ultrafiltration membrane as collection matrix, which preferably has one or more of the following features:
   i) it has a MWCO in a range selected from 1 kDa to 300 kDa, 1 kDa to 200 kDa, 3 kDa to 100 kDa and 5 kDa to 50 kDa; and/or ii) the material is selected from PES and a cellulose material, preferably selected from PES, CA, CTA and RC.

17. The method according to one or more of items 1 to 16, wherein the method is for purifying a target nucleic acid from a nucleic acid containing sample and wherein the target nucleic to be purified is placed into the passage of the device
   a) as part of a lysate;
   b) bound to a solid phase; or
   c) as part of an eluate, optionally in combination with the solid phase that was used for isolating the target nucleic acid from the sample.

18. The method according to item 17, wherein the method comprises binding the target nucleic acid contained in the sample to a solid phase, separating the bound nucleic acid from the sample and placing the target nucleic acid, optionally while being bound to the solid phase, into the passage of the device.

19. The method according to item 17 or 18, wherein the passage of the device comprises a liquid permeable closing matrix, a liquid permeable separation matrix and a liquid permeable collection matrix and wherein the target nucleic acid is placed between the closing matrix and the separation matrix, wherein upon application of the electric field the target nucleic acid migrates towards the anode through the separation matrix and is retained at the collection matrix.

20. The method according to one or more of items 1 to 19, wherein the running solution has one or more of the following characteristics:
   a) it is suitable to effect elution of the target molecule, such as a nucleic acid, from the solid phase if the target molecule is placed into the passage of the device while being bound to the solid phase;
   b) it comprises a buffering agent, preferably Tris or MOPS;
   c) it comprises a buffering agent in a concentration selected from 10 mM to 100 mM, 15 mM to 75 mM, 20 mM to 70 mM, 25 mM to 60 mM and 30 mM to 55 mM;
   d) it comprises a salt, preferably an alkali metal salt, preferably in a concentration of 100 mM or less or 75 mM or less;
   e) it is selected from
      i) a running buffer comprising Tris in a concentration of 10 mM to 25 mM and having a pH in the range of 7.5 to 8.5, preferably pH 8; and
      ii) a running buffer comprising Tris in a concentration of 30 mM to 60 mM, preferably 30 mM to 50 mM and having a pH in the range of 7.5 to 8.5, preferably pH 8; and
      iii) a running buffer comprising MOPS in a concentration of 5 mM to 50 mM, preferably 10 mM to 25 mM, and having a pH in the range of 6.5 to 7.5, wherein said running buffer optionally comprises a salt in a concentration selected from 5 mM to 100 mM, 10 mM to 75 mM and 15 mM to 60 mM;
   and/or
   f) it is compatible with a subsequent nucleic acid analysis method, which preferably is an amplification reaction.

21. The method according to one or more of items 1 to 20, wherein the device is a discrete body, preferably a cartridge, that does not comprise electrodes for generating the electric field and wherein the device is at least during the electrophoretic separation step placed into an electrophoresis chamber which comprises the electrodes for generating the electric field and wherein the passage of the device is via the collection matrix and the closing matrix, if a closing matrix is present, in fluid communication with the electrophoresis chamber.

22. The method according to item 21, wherein the device is a hollow tube and a liquid permeable closing matrix is located at one end region of the tube and the collection matrix is located at the other end region of the tube whereby the passage is formed between the closing matrix and the collection matrix and wherein the closing matrix is located in the region of the cathode and the collection matrix is located in the region of the anode and wherein preferably, the electrodes of the electrophoresis chamber are parallel to the closing matrix and the collection matrix of the device and wherein preferably, the electrodes are adapted in dimension and shape to fit the dimension and shape of the closing matrix and the collection matrix.

23. The method according to one or more of items 1 to 22, wherein the device has an elongated body, preferably tube-shaped, which comprises in the passage a loading chamber that is formed at least in part by a liquid permeable closing matrix and a liquid permeable separation matrix and wherein a target nucleic acid is placed into the loading chamber, optionally while being bound to a solid phase, through an opening and wherein the device comprises in the passage a collection chamber that is formed at least in part by the separation matrix and the collection matrix and wherein the eluted nucleic acids are collected from the collection chamber through an opening.

24. The method according to item 23, wherein the method comprises
   placing the target nucleic acid, optionally while being bound to a solid phase, into the loading chamber of the device through an opening in the device;
   applying the electric field, wherein the target nucleic acid migrates according to its charge in the electric field, passes through the separation matrix and is retained at the collection matrix;
   optionally reversing the electric field; and
   collecting the purified target nucleic acid from the collection chamber through an opening in the device.

25. The method according to one or more of items 1 to 24, having one of more of the following characteristics:
   a) the electric field strength used for generating the electric field is selected from 1 to 20 V/cm, 3 to 17 V/cm, 5 to 15 V/cm and 7 to 12 V/cm, preferably 10 V/cm; and/or
   b) the passage has a cross section in the mm to cm range.

26. The method according to one or more of items 17 to 25, for isolating RNA as target nucleic acid, wherein the method comprises
   (a) binding RNA to a solid phase;
   (b) placing the solid phase with the bound RNA into a loading chamber of a device, wherein the device comprises a passage which comprises the loading chamber, optionally a liquid permeable separation matrix adjacent to the loading chamber, and a liquid permeable collection matrix and wherein the solid phase with the bound target nucleic acid is present in the loading chamber in a liquid medium comprising at least one water-miscible organic solvent and wherein the RNA remains bound to the solid phase in said liquid medium, wherein preferably, particles, more preferred magnetic particles are used as solid phase;
   (c) generating an electric field between a cathode and an anode and using a running solution that conducts the electric current, wherein the running solution dilutes the liquid medium comprised in the loading chamber resulting in elution of the bound RNA, and wherein the eluted RNA migrates according to its charge in the electric field and is retained by the collection matrix;

(d) collecting the purified RNA.

27. The method according to item 26, wherein the liquid medium comprises the at least one water-miscible organic solvent in a concentration selected from 25% to 95% (v/v), 30% to 90% (v/v) and 35% to 85% (v/v).

28. The method according to item 26 or 27, wherein the water-miscible organic solvent comprised in the liquid medium has one or more of the following characteristics:
   i) it is selected from aprotic polar solvents and protic solvents;
   ii) it is selected from aliphatic, short chained branched or unbranched alcohols with preferably one to five carbon atoms, preferably selected from methanol, ethanol, propanol, isopropanol and butanol, more preferably selected from ethanol and isopropanol; and/or
   iii) it is selected from sulfoxides, ketones, nitriles, cyclic or aliphatic ethers, lactams and tertiary carboxylic acid amides and is preferably selected from the group consisting of acetone, acetonitrile, dimethyl sulfoxide (DMSO), tetrahydrofuran (THF), dioxane and dimethylformamide (DMF).

29. The method according to one or more of items 26 to 28, comprising
   (a) lysing the biological sample in the presence of at least one chaotropic salt and binding RNA to particles providing a silicon containing surface, wherein binding occurs in the presence of the at least one chaotropic salt and optionally at least one water-miscible organic solvent,
   (b) placing the solid phase with the bound RNA into a loading chamber of a device, wherein the device comprises a passage which comprises the loading chamber at one end, a liquid permeable separation matrix adjacent to the loading chamber and a liquid permeable collection matrix at the other end and wherein the solid phase with the bound RNA is present in the loading chamber in an aqueous liquid medium comprising at least one water-miscible organic solvent in a concentration that lies in the range of 30% to 90% (v/v) and wherein the RNA remains bound to the solid phase in said aqueous medium;
   (c) generating an electric field between a cathode and an anode and using a running solution that conducts the electric current, wherein the running solution dilutes the aqueous liquid medium in the loading chamber resulting in elution of the bound RNA upon dilution of the aqueous liquid medium, and wherein the eluted RNA migrates according to its charge in the electric field through the separation matrix and is retained by the collection matrix;
   (d) optionally reversing the electric field and collecting the purified RNA.

30. The method according to one or more of items 1 to 29, wherein the device is a device according to one or more of items 31 to 37 and wherein preferably, the device is a device according to one or more of items 33 to 37 and is placed in an electrophoresis chamber comprising electrodes for generating the electric field.

31. A device suitable to be placed in an electrophoresis chamber for use in a method for purifying a charged target molecule by electrophoresis, the device comprising a first end region and a second end region and a passage between the first end region and the second end region wherein the passage is closed at the second end region by a liquid permeable collection matrix.

32. Device according to item 31, wherein the device is a cartridge.

33. Device according to item 31 or 32, wherein the device does not comprise electrodes for generating an electric field.

34. Device according to one or more of items 31 to 33, having one or more of the following characteristics:
   a) the collection matrix has one or more of the characteristics as defined in item 4;
   b) the passage is closed at the first end region by a liquid permeable closing matrix, wherein optionally the closing matrix has one or more of the characteristics as defined in item 9,
   c) the passage comprises a liquid permeable separation matrix, wherein optionally the separation matrix has one or more of the characteristics as defined in item 10;
   d) the passage is closed at the first end region by a liquid permeable closing matrix and a liquid permeable separation matrix is placed between the closing matrix and the collection matrix, wherein preferably, the closing matrix, the separation matrix and the collection matrix are provided as discrete bodies that are spaced apart in the passage;
   e) it comprises at least one supporting base;
   f) it comprises at least one handle;
   g) it has a length of 1.25 cm to about 5 cm, 1.5 cm to about 4 cm, 1.75 cm to 3.5 cm or 2 cm to 3.0 cm; and/or
   h) the device has one or more features as defined in items 12 to 16 and 21 to 22.

35. The device according to one or more of items 31 to 34, wherein the device has an hollow elongated casing which comprises the passage and wherein the two ends of the device are opposed to each other and wherein the passage is closed at the first end region by a liquid permeable closing matrix and a liquid permeable separation matrix is placed between the closing matrix and the collection matrix, wherein the closing matrix, the separation matrix and the collection matrix are provided as discrete bodies that are spaced apart in the passage, whereby a loading chamber is formed at least in part by the closing matrix and the separation matrix and a collection chamber is formed at least in part by the separation matrix and the collection matrix.

36. The device according to item 35, wherein the device has one or more of the following characteristics
   a) it comprises an aperture being positioned in the region of the loading chamber;
   b) it comprises an aperture in the region of the collection chamber;
   c) it comprises an aperture in the region of the separation matrix and/or between the separation matrix and the loading chamber;
   d) the cross section of the loading chamber is
      i) greater than the cross section of the separation matrix and wherein optionally, the cross section of the separation matrix is greater than the cross section of the collection matrix, and/or
      ii) the passage is shaped in a tapered manner reducing the cross section along the passage from the loading chamber to the separation matrix and optionally to the collection matrix; or iii) the cross section of the passage is substantially the same from the first end region to the second end region;
and/or
e) it comprises a loading pad in the loading chamber, the loading pad preferably being spaced apart from the separation matrix, wherein the loading pad can absorb a liquid.

37. The device according to item 35 or 36, having one or more of the following characteristics
   a) the volume that can be received by the collection chamber of the device is smaller than the volume that can be received by the loading chamber of the device and wherein optionally, the volume of the collection chamber is 70% or less, 50% or less, 40% or less or 30% or less than the volume of the loading chamber;
   b) apertures provided in the device for entry and removal of the target molecule and/or venting are smaller than the end openings of the passage; and/or
   c) the aperture in the region of the loading chamber is larger than the aperture in the region of the collection chamber.

38. Use of a device according to any one of items 31 to 37 in a method according to any one of items 1 to 30.

39. Use of a device according to any one of items 33 to 37 for purifying a charged target molecule, preferably a nucleic acid, using electrophoresis, wherein the device is placed in an electrophoresis chamber for electrophoresis and wherein the electrophoresis chamber comprises the electrodes for generating the electric field.

40. Assembly set for a device according to any one of items 31 to 37, wherein the assembly set comprises at least two containers, each of the at least two containers having at least two openings, wherein the at least two containers are connectable to form a passage, one of the containers comprising a liquid-permeable separation matrix and/or a liquid-permeable collection matrix and the other container comprising a liquid permeable closing matrix.

41. A method for purifying a charged target molecule, preferably a nucleic acid, by electrophoresis, comprising the step of inserting a device according to any one of items 33 to 37 into an electrophoresis chamber which is prefilled or adapted to be filled with a running solution and which chamber comprises electrodes for generating an electric field.

42. A system comprising the device according to any one of items 33 to 37 and an electrophoresis chamber which comprises electrodes for generating an electric field.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Thus, for example, reference to "a separation matrix" includes a single separation matrix, as well as two or more separation matrices. Likewise, reference to "an opening, "an aperture" and the like includes single entities and combinations of two or more of such entities. Reference to "the disclosure" and "the invention" and the like includes single or multiple aspects taught herein; and so forth. Aspects taught herein are encompassed by the term "invention".

The term "solution" as used herein in particular refers to a liquid composition, preferably an aqueous composition. It may be a homogenous mixture of only one phase or a suspension of two immiscible liquids but it is also within the scope of the present invention that a solution comprises solid constituents such as e.g. precipitates or nucleic acid binding particles.

According to one embodiment, subject matter described herein as comprising certain steps in the case of methods or as comprising certain elements in the case of devices or systems, refers to subject matter consisting of the respective steps or elements. It is preferred to select and combine preferred embodiments described herein and the specific subject-matter arising from a respective combination of preferred embodiments also belongs to the present disclosure.

DESCRIPTION OF THE FIGURES

Examples of the invention and in particular the device will now be described with reference to the accompanying drawings. The described features are general design elements of the device. This also follows from the associated advantages. Therefore, even if a feature is described in conjunction with a specific embodiment of the device it is to be noted that said feature can also be used in conjunction with a different embodiment of the device, which differs with respect to other features.

FIG. 1 shows a schematic drawing of a device 1 according to the invention when placed in an electrophoresis chamber. The device 1 is positioned between two electrodes 2, 3 that are located in an electrophoresis chamber 4. When an electric field is generated, electrode 2 provides the cathode and electrode 3 provides the anode in the shown set-up. The device 1 comprises a casing 5 forming a hollow body which provides a passage inside. An opening 6, 7 is formed at each end region 66, 77. The size and shape of the electrodes 2, 3 preferably correspond to the size and shape of the openings 6, 7 of the device. The passage of the device 1 comprises at the end region 66 which is oriented to electrode 2 a porous, liquid-permeable closing matrix 8 and at the end region 77 which is oriented to electrode 3 a porous, liquid-permeable collection matrix 9. Additionally, the passage of the device 1 comprises a porous, liquid permeable separation matrix 10. The closing matrix 8 forms with the casing 5 and the separation matrix 10 a loading chamber 11 which receives the nucleic acid containing material, which preferably is a solid phase comprising bound nucleic acids. The separation matrix 10 forms with the casing 5 and the closing matrix 9 a collection chamber 12 which retains the purified nucleic acids. The device 1 and the electrophoresis chamber 4 are filled with a running buffer (not shown) which is in contact with the electrodes 2, 3. Upon application of an electric field, the nucleic acids migrate from the loading chamber 11 through the separation matrix 10 into the collection chamber 12 where they are retained by the collection matrix 9. The large arrow indicates the migration direction of the nucleic acids in the electric field.

Figure 2:
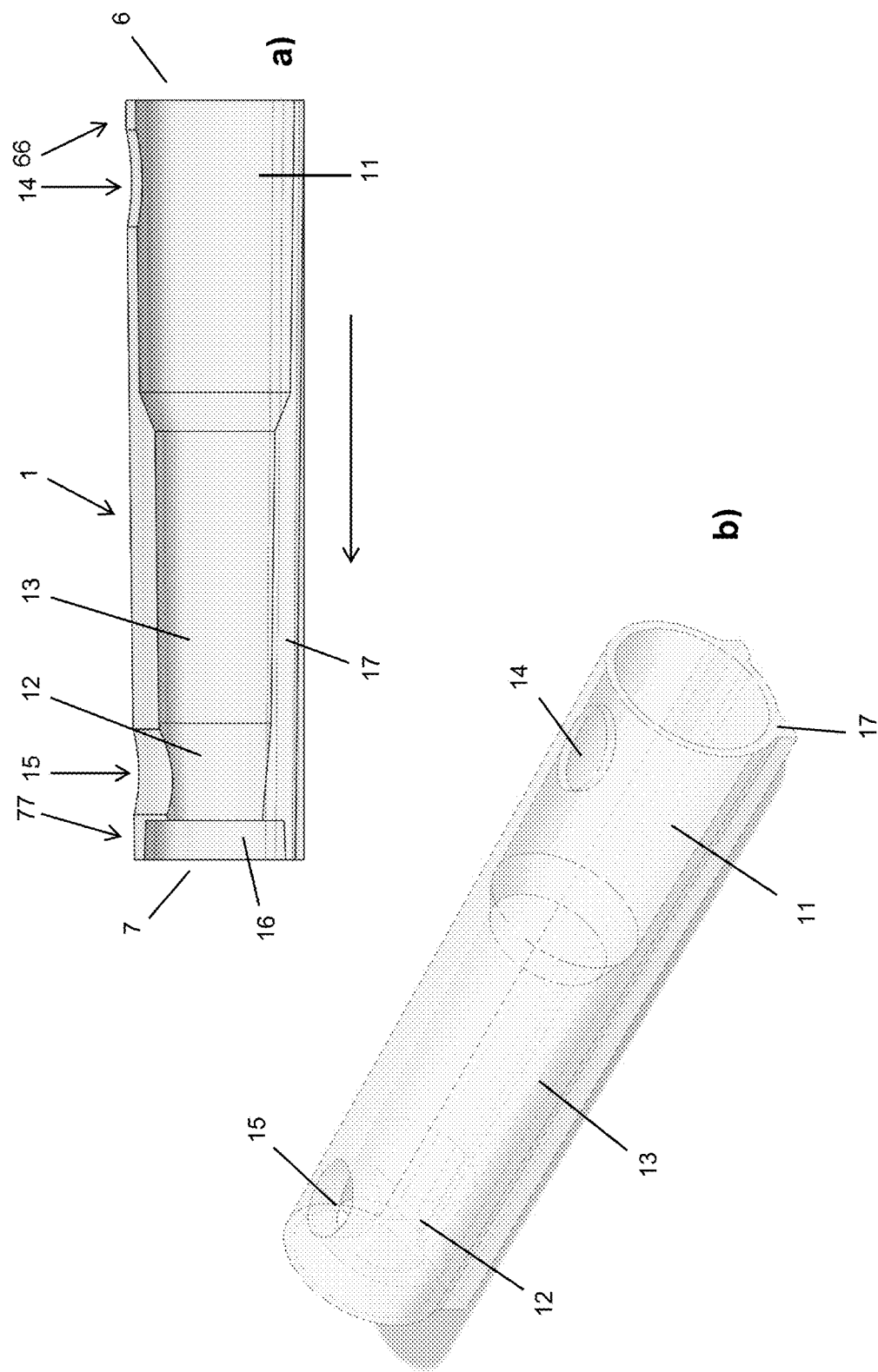

FIG. 2 shows an embodiment of a device, wherein FIG. 2a is a transparent isometric view and FIG. 2b is a longitudinal section view. In the embodiment shown in FIG. 2 the cross section of the passage is reduced from the loading section to the separation section to the elution or collection section. The device 1 has two openings 6, 7 at the two opposed end regions 66 and 77. The closing matrix, the separation matrix and the collection matrix are not shown. The device 1 has an elongated tube-shaped body what is preferred in the context of the invention. The cross section (here diameter) of the loading chamber 11 is greater than the cross section (here diameter) of the region for the separation matrix, herein referred to as the separation section 13. The cross section (here diameter) of the separation section 13 is greater than the cross section (here diameter) of the collection chamber 12 from which the eluted nucleic acids are collected. In the region of the loading chamber 11 an opening/aperture 14 is formed. The nucleic acid containing material can be placed into the loading chamber 11 of the device 1 via said opening/aperture 14. This simplifies loading of the device from the top. In the region of the collection chamber 12 an opening/aperture 15 is formed. The purified charged target molecule is retained by the collection matrix in the collection chamber 12 can be removed from the collection chamber through this opening 15, e.g. using a pipette. This simplifies the collection. In the end region 77 a retainer is formed for mounting the collection matrix. In the shown embodiment, a circle-shaped block 16 is formed in the housing of the device against which the collection matrix can rest, thereby fixing the collection matrix within the device. The collection matrix can for example be hold in the position of abutment against the block 16 by a ring. The device comprises in the shown embodiment a supporting base 17 in the shape of a pedestal. This supporting base simplifies secure placement of the device in an electrophoresis chamber. The loading chamber 11 may be larger than the collection chamber 12, as it is shown in the embodiment of FIG. 2. A small collection chamber is advantageous as it concentrates the purified target molecule in the collection chamber 12 because the running solution volume in which the target molecule is contained is reduced.

Figure 3:
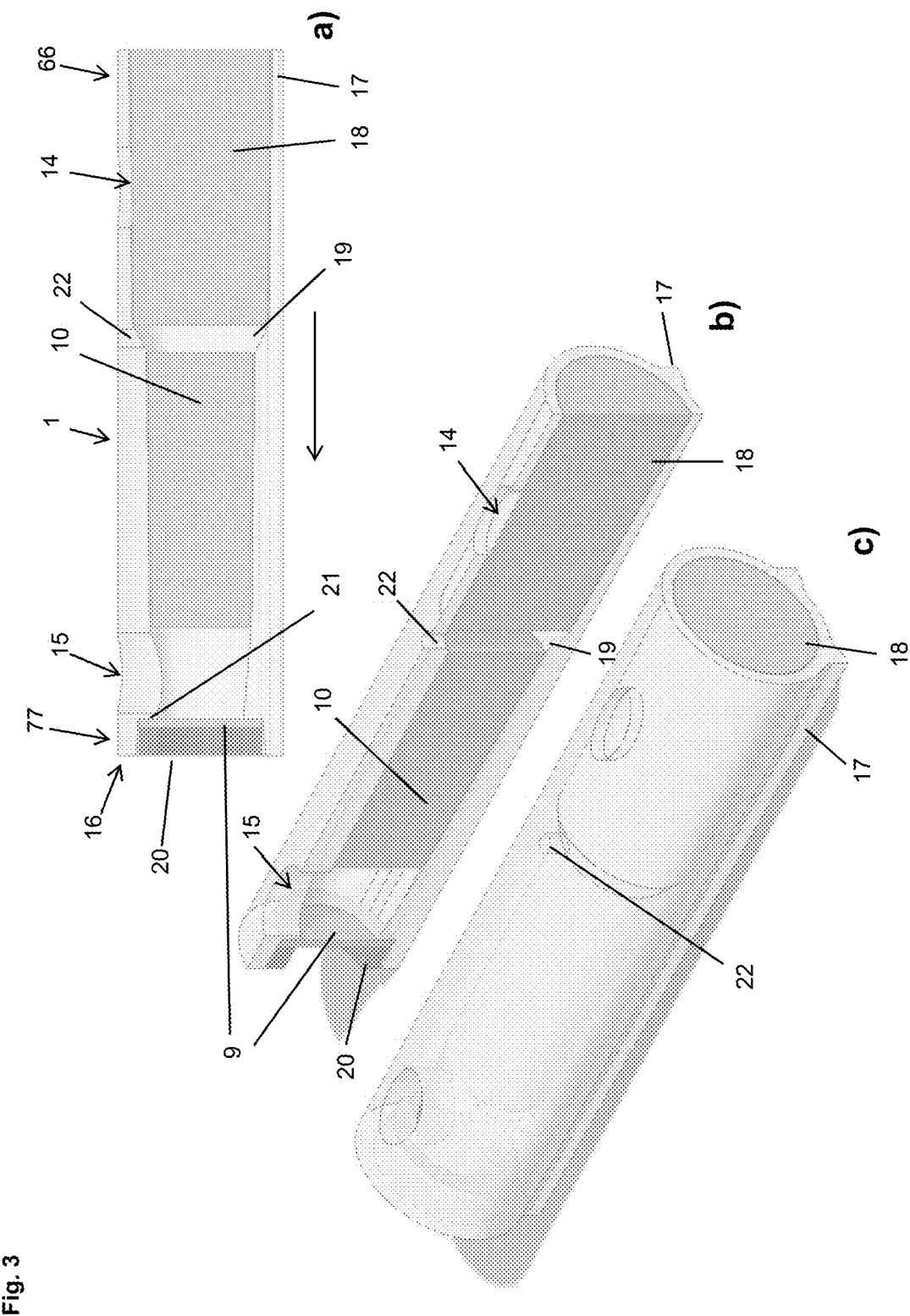

FIG. 3 shows a further embodiment of the device, wherein FIG. 3a is a transparent isometric view, FIG. 3b is an isometric longitudinal section view; and FIG. 3c is a longitudinal section view. FIG. 3 shows the device 1 according to an embodiment wherein the loading chamber comprises a loading pad 18 which functions at the same time as closing matrix. The loading pad 18 which essentially fills the loading chamber simplifies the introduction of a target molecule containing liquid material, as it is described in detail in the general description. The separation section comprises a separation matrix 10 and the device 1 additionally comprises a collection matrix 9 for retaining the purified target molecule in the collection chamber. A gap 19 is present between the loading pad 18 and the separation matrix 10. This gap 19 prevents or reduces diffusion from the loading pad 18 into the separation matrix 10. The collection matrix 9 is close fitting with block 16 and the collection matrix 9 is held by a ring-shaped retainer, i.e. retainer ring, 20. To hold the collection matrix 9 in place, the device comprises a restriction 21 which serves as "counter-retainer ring". Additionally, the device comprises a vent opening 22 which extends in the same direction as the loading and collection openings 14, 15. The vent opening allows air to exit the device, when the device is filled with running solution. As is shown in FIG. 3, the gap 19 is preferably located beneath the vent opening 22.

Figure 4:
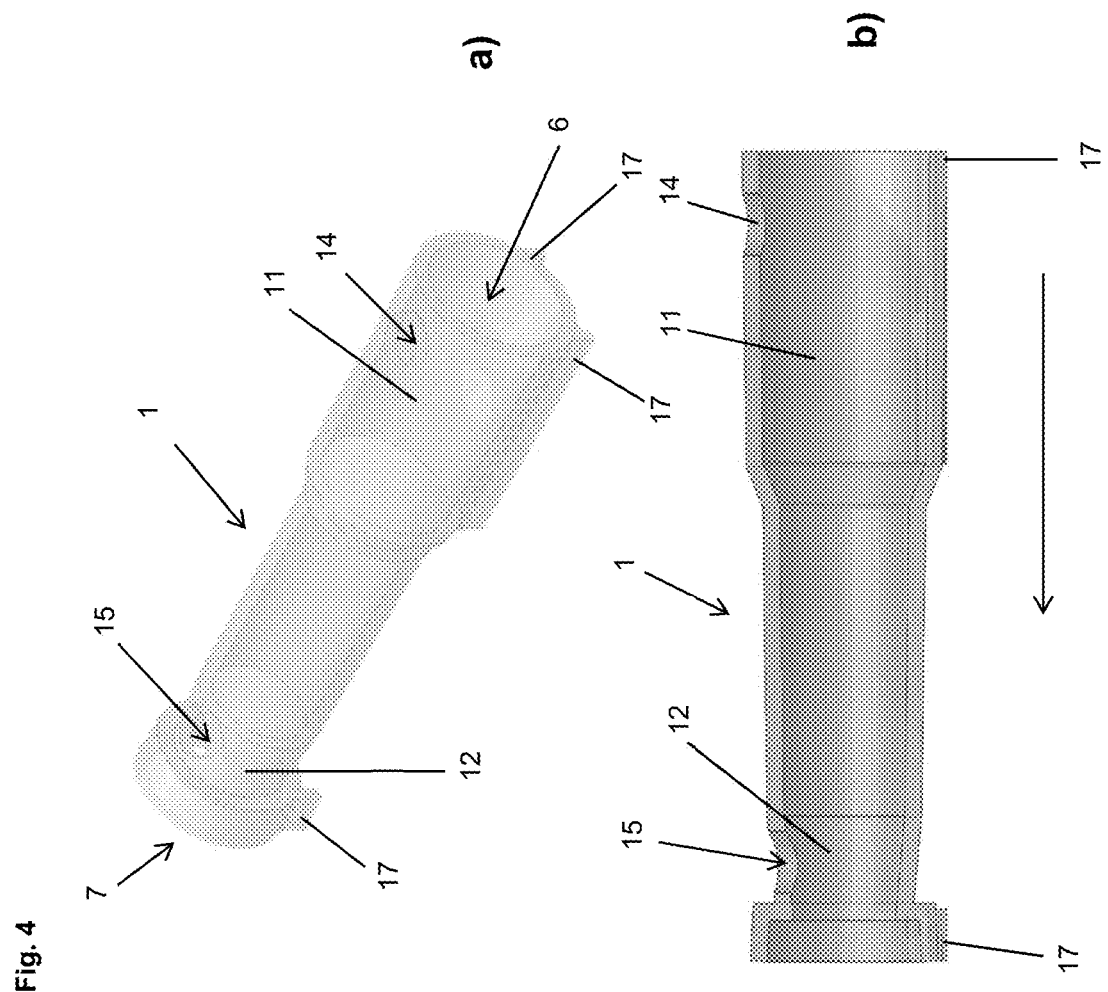

FIG. 4 shows a further embodiment of the device, wherein FIG. 4a is a transparent isometric view and FIG. 4b is a longitudinal section view. In the embodiment shown in FIG. 4 the housing of the device 1 has a wall thickness with substantially the same thickness along the longitudinal axis of the device. The device and accordingly the passage formed inside is tapered into the direction of the collection chamber 12 from which the purified target molecule, preferably a nucleic acid, can be removed through the opening 15. Supporting bases 17 are positioned at the end regions 6 and 7 under the loading chamber 11 and under the region which receives the collection matrix. The supporting base(s) 17 can be formed as one element or can be provided by multiple elements. The device may thus comprise more than one supporting base 17. In the shown embodiment, the supporting base is provided as pedestal which inter alia level the tube decline and allow positioning of the device in the electrophoresis chamber.

Figure 5:
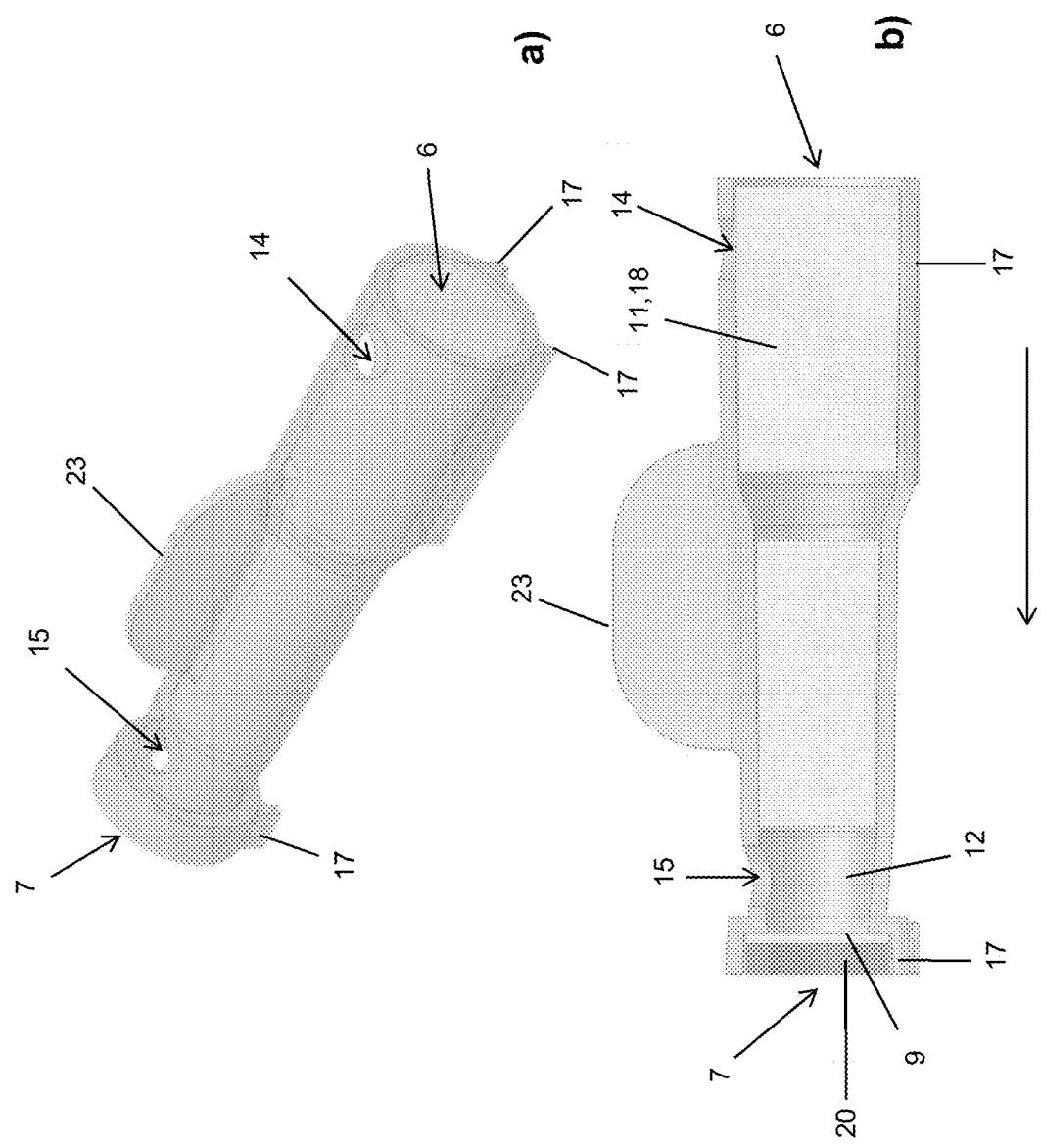

FIG. 5 shows a further embodiment of the device, wherein FIG. 5a is a transparent isometric view and FIG. 5b is a longitudinal section view. The shown embodiment comprises a handle 23 in the shape of a rib or a fin. The handle 23 is formed as an appendix extending in the direction of the openings 6, 7. The handle 23 can also be used to place the device into electrophoresis chamber in the right direction. The loading chamber 11 may comprise a loading pad 18 which can be provided as filter having a diameter of e.g. 8 mm. The separation section may comprise a separation matrix 10 which may also be a filter. The diameter of the separation matrix is preferably smaller than the diameter of the loading pad 18, e.g. 6 mm. The collection matrix 9 is held in place by a retainer ring 20.

Figure 6:
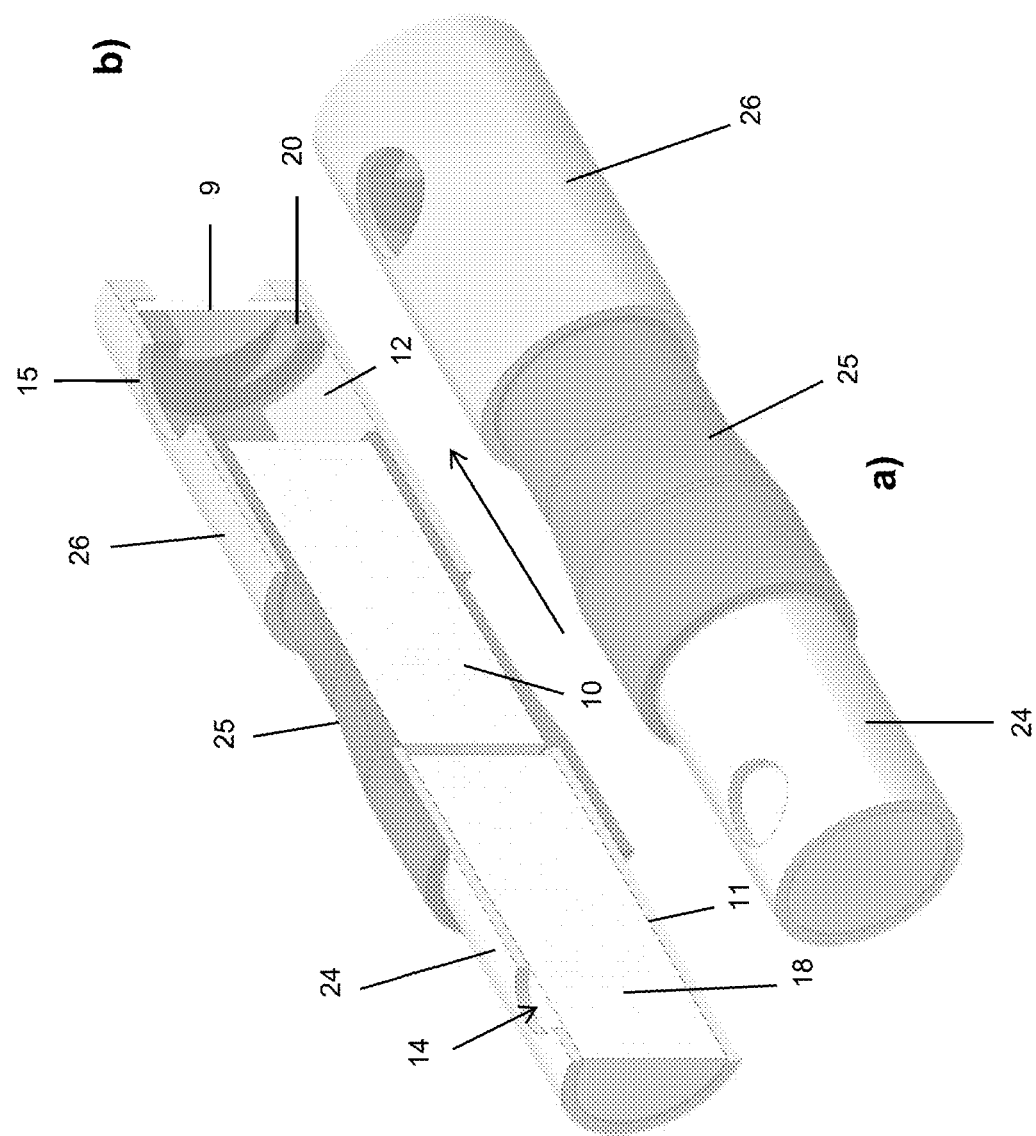

FIG. 6 shows a device according to the invention assembled from an assembly set, wherein FIG. 6a is an isometric view and FIG. 6b is an isometric longitudinal section view. FIG. 6 shows a device 1 which is assembled from an assembly set according to the invention. The assembly set comprises three containers 24, 25, 26 which are connected to each other. The container 24 comprises the loading chamber 11 which in the shown embodiment comprises a loading pad 18. The container 25 comprises the separation matrix 10. The container 26 comprises the collection chamber 12 and the collection matrix 9. The containers 24, 25 and 26 are adapted to each other with regard to the outer diameter and the inner diameter allowing to insert one of the containers into another. The container 24 can be inserted with one end into the container 25. The other end of the container 25 can be inserted into one end of the container 26. The containers can be pre-filled with a closing matrix and/or a loading pad 18, a separation matrix 10 and a collection matrix 9, respectively. In the shown embodiment, the collection matrix is held in place by a retainer ring 20. The closing matrix 8, the separation matrix 10 and the collection matrix 9 can be suitably adapted to each other with regard to the charged target molecule, which is to be separated, isolated and/or purified.

Figure 7:
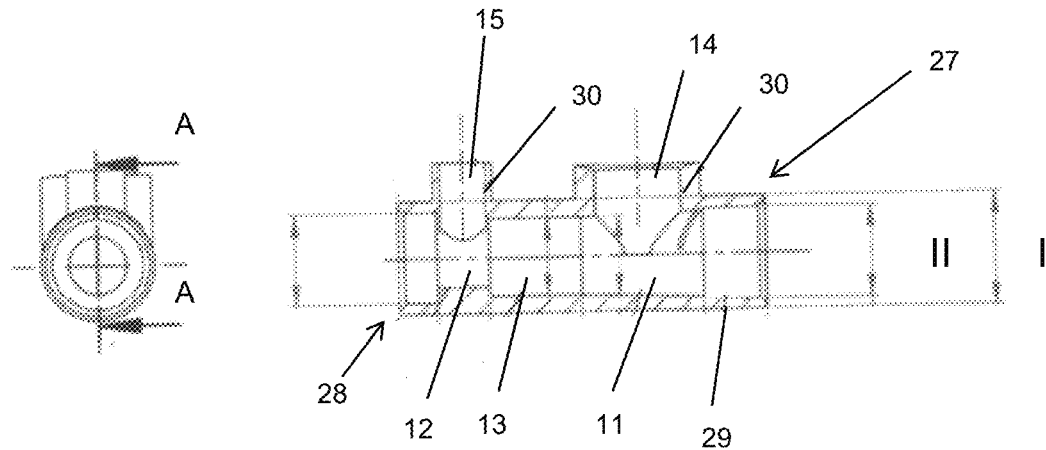

FIG. 7 shows a preferred embodiment of the device cut along A-A. The device is designed as elongated tube and receives a closing matrix, a separation matrix and the collection matrix (the matrices are not shown). The device may have an overall length in the range of 2.5 to 3.5 cm, in the shown embodiment 2.83 cm. The outer cross section I of the device (diameter in the shown embodiment) is the same over the complete device and hence at the rear end 27 and front end 28. At the rear end 27 a retainer is formed for mounting the closing matrix. In the shown embodiment, a circle-shaped block 29 is formed in the housing of the device which receives the closing matrix. The closing matrix confines together with the separation matrix and the device housing the loading chamber 11 into which the charged target molecule, which is preferably a negatively charged target molecule such as a nucleic acid, is introduced. An aperture 14 at the top of the device, above the loading chamber, is provided for loading the target molecule. It has a collar 30 in order to prevent that running solution enters or exits the device during operations. Such collar 30 is also provided at aperture 15 for collecting the purified target molecule. The collars can extend in a tube-like fashion. Loading aperture 14 is preferably larger than collection aperture 15. The loading chamber 11 is substantially larger than the collection chamber 12. This is achieved in the shown embodiment by making the inner cross section of the passage section which provides the loading chamber 11 substantially larger than the inner cross section of the passage section that provides the collection chamber 12. In addition, the loading chamber 11 also stretches over a longer section of the passage than the collection chamber 12. Therefore, the loading chamber 11 can receive a larger amount of liquid than the collection chamber 12. This is advantageous, as it results in a concentration effect. Adjacent to the loading chamber 11 the separation section 13 is provided which receives in use the separation matrix. The collection chamber 12 is located adjacent to the separation matrix. An aperture 15 is provided at the top of the collection chamber 12 to simplify removal of the purified target molecule. At the front end 28 again a substantially circle-shaped block is formed in the housing of the device against which the collection matrix (not shown) can rest thereby fixing the collection matrix within the device as it is also described in FIG. 3. The collection matrix can again be hold in the position of abutment against the block by a retainer ring. The collection matrix confines together with the separation matrix and the housing of the device the collection chamber 12. The passage that is formed between the rear end 27, respectively the comprised closing matrix and the front end 28, respectively the provided collection matrix, has in the shown embodiment a cross section II which is reduced from the loading section to the separation section to the collection section, what is one optional design element of the device. The passage can also be tapered within a certain section as it is evident from the loading chamber 11. The passage or sections thereof may generally have a decline of approximately 3% to 5%, in particular 4%. The advantages of a tapered passage are described herein. The front end 28 which receives the collection matrix which can be held e.g. by a ring has again a larger diameter than the collection chamber 12. In the shown embodiment, the cross section of the opening at the front end 28 is the same as at the block 29 at the rear end 27. Therefore, the cross section enlarges again at the front end of the passage, respectively the device. This is advantageous, as thereby the rear end 27 and the front end 28 have substantially the same size and dimension which is favourable with respect to the electrodes that are used in the electrophoresis chamber in combination with this device. It allows to use electrodes that have the same size and dimension and also allows to place the device in different orientations to the electrophoresis chamber, depending on the charge of the target molecule to be purified. According to a preferred embodiment, the device is as is shown in FIG. 7 an elongated tube which preferably is except for the openings and apertures a closed tube. The inner diameter of the tube which provides the passage lies according to one embodiment in the range of 2.5 mm to 10 mm, preferably 3 mm to 9 mm, more preferably 3.5 mm to 8 mm. According to one embodiment, the separation section has a diameter within the passage that lies in a range of 4 mm to 8 mm, preferably 5 mm to 7 mm. As is shown, the diameter of the collection chamber 12 is smaller than the diameter in the separation section 13. At the front end 28, the device enlarges again and has the same diameter at the front end 28 as at the rear end 27.

Figure 8:
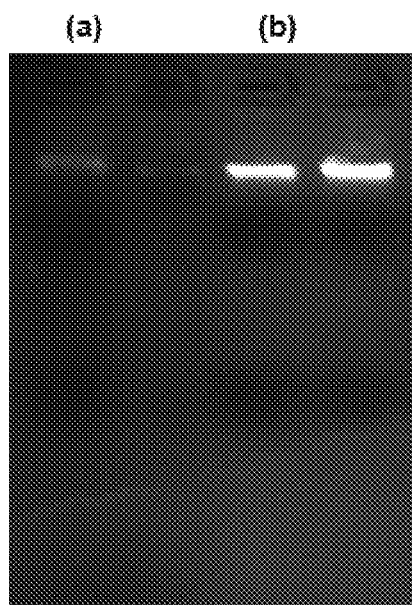

FIG. 8 shows eluates after electric field based separation: (a) high-salt lysate directly applied to the device; (b): procedure according to the invention wherein the nucleic acid is bond to a solid phase.

Figure 9:
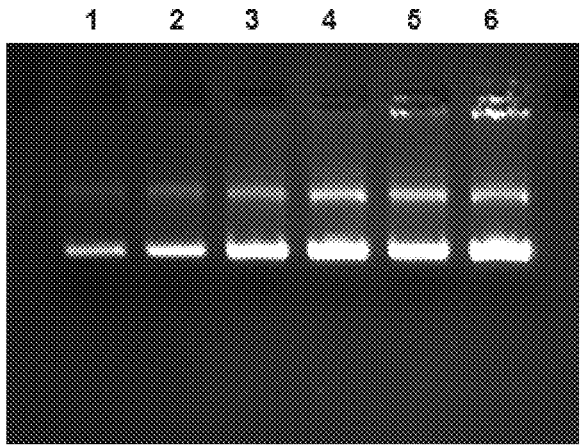

FIG. 9 shows an analytical agarose gel of plasmid DNA purified according to the present method with different membrane types in the device (lane 1+2: 100 kDa PES; lane 3+4: 10 kDa RC; 5+6: 10 kDa PES).

Figure 10:
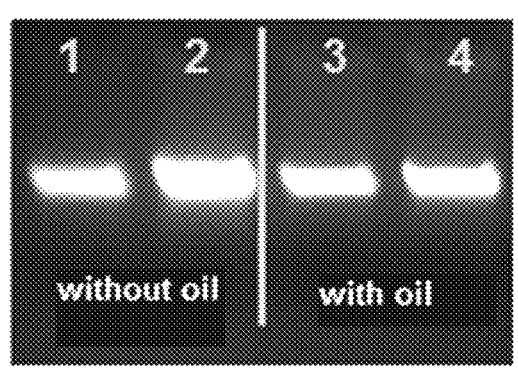

FIG. 10 shows an analytical agarose gel of pure gDNA isolated from E. coli cells w/o (1, 2) and with (3, 4) mineral oil for bead separation (duplicates). No DNA degradation or impurities like RNA are visible.

Figure 11:
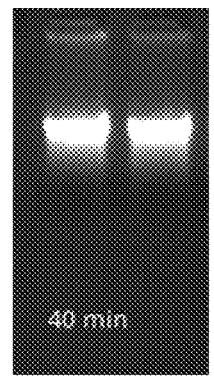

FIG. 11 shows an analytical agarose gel of pure gDNA isolated from rat kidney (duplicate). No DNA degradation or impurities like RNA are visible.

Figure 12:
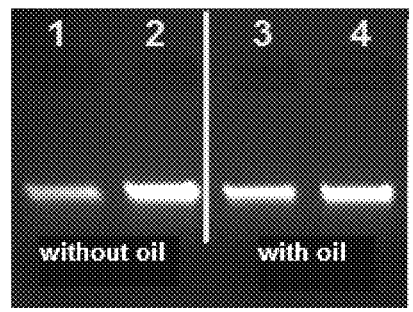

FIG. 12 shows an analytical agarose gel of pure gDNA isolated from human blood with and w/o mineral oil for bead separation (duplicates). No DNA degradation or impurities like RNA are visible.

Figure 13:
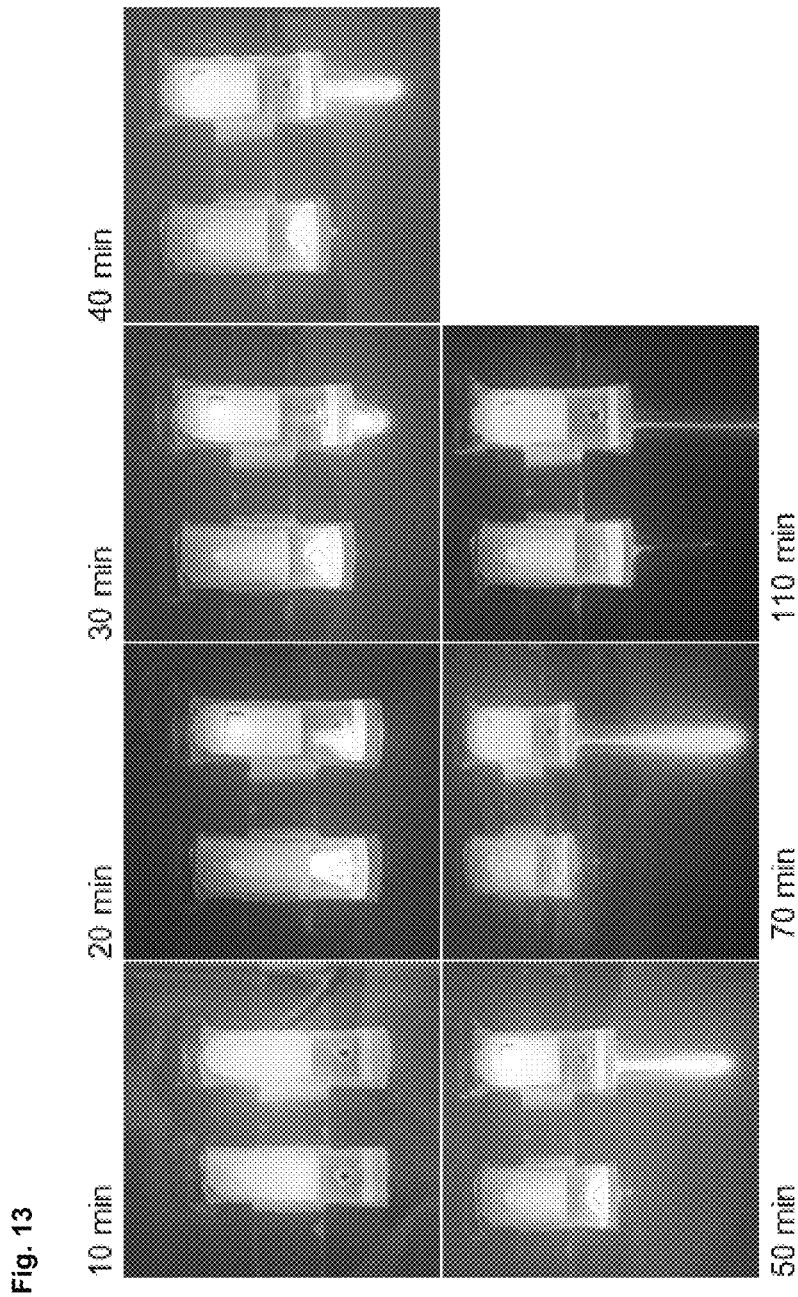

FIG. 13 shows original (mostly supercoiled; left device) and linearized (right device) plasmid DNA migrating due to the electric field in a device according to the invention.

Figure 14:
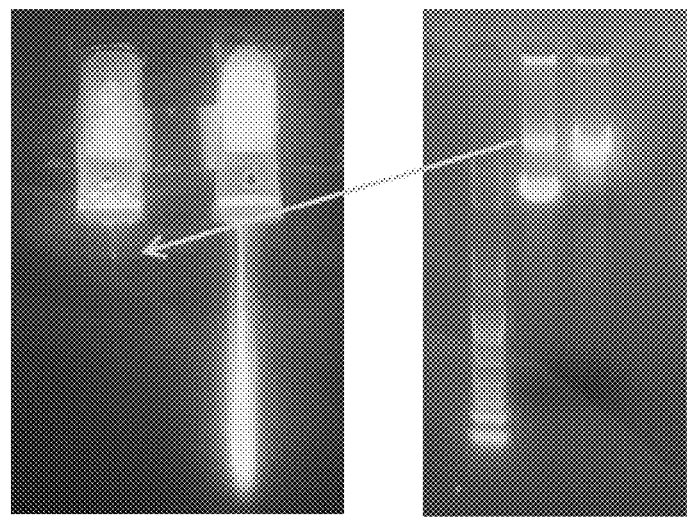

FIG. 14 shows original (left) and digested (right) plasmid DNA during the separation with devices according to the invention after 70 min (left picture) and agarose gel to demonstrate presence of non-supercoiled plasmid DNA in the original preparation (right picture).

Figure 15:
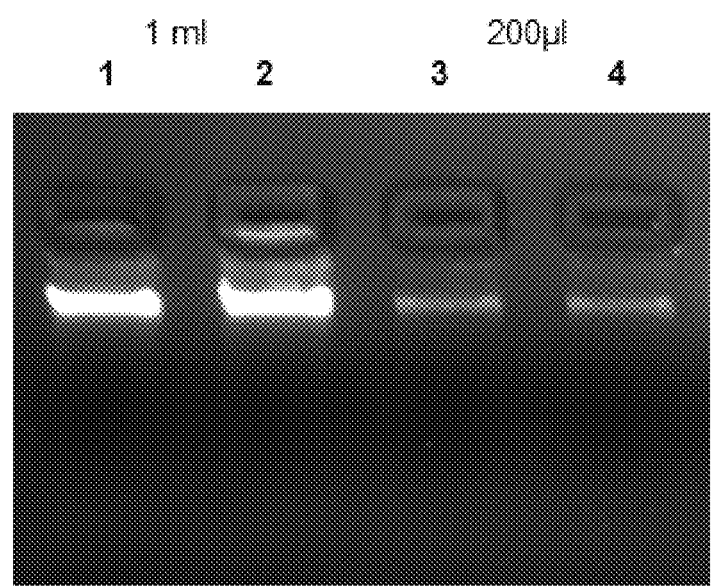

FIG. 15 shows equal volumes of eluates from 200 µl (lanes 3, 4) and 1 ml (lanes 1,2) samples were analyzed. Band intensity reflects the different sample input volumes demonstrating similar performance over different scales using identical configurations.

Figure 16:
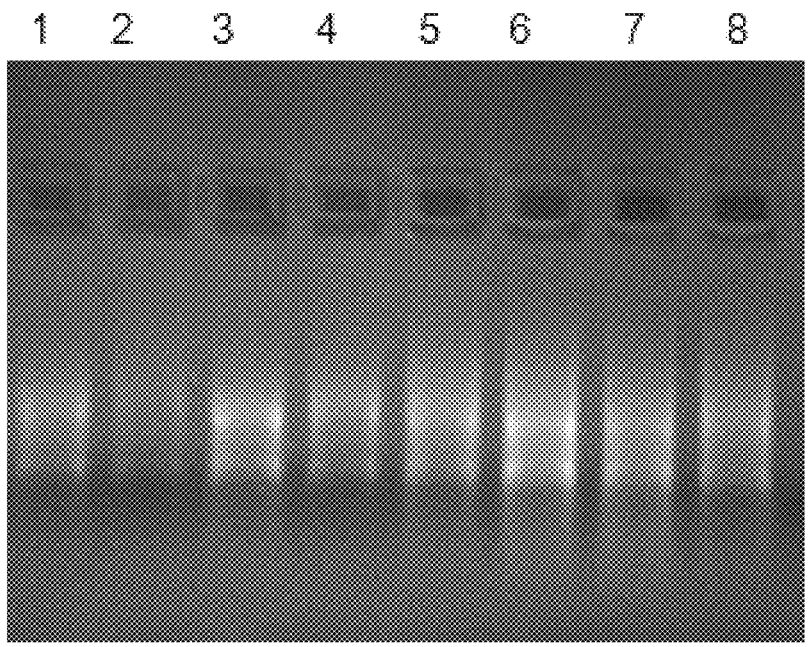

FIG. 16 shows eluates from RNA collected with an electrophoresis assisted procedure: lanes 1-4: 100 kDa membrane; lanes 4-8: 10 kDa membrane.

Figure 17:
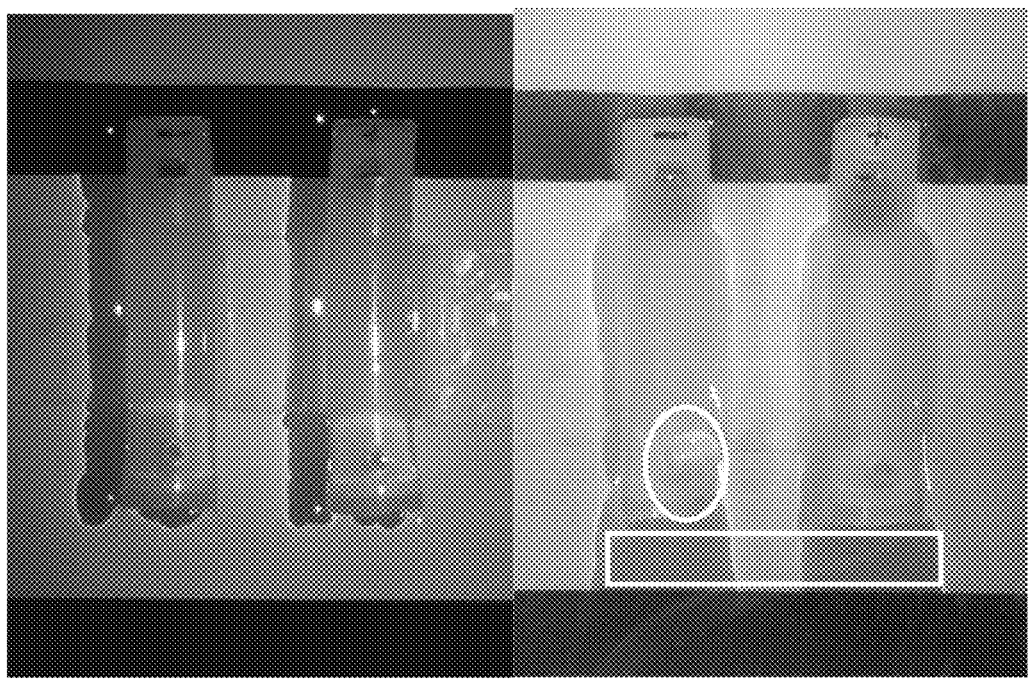

FIG. 17 shows the results of Example 8. Left: t=0 min; right t=8 min.

Figure 18:
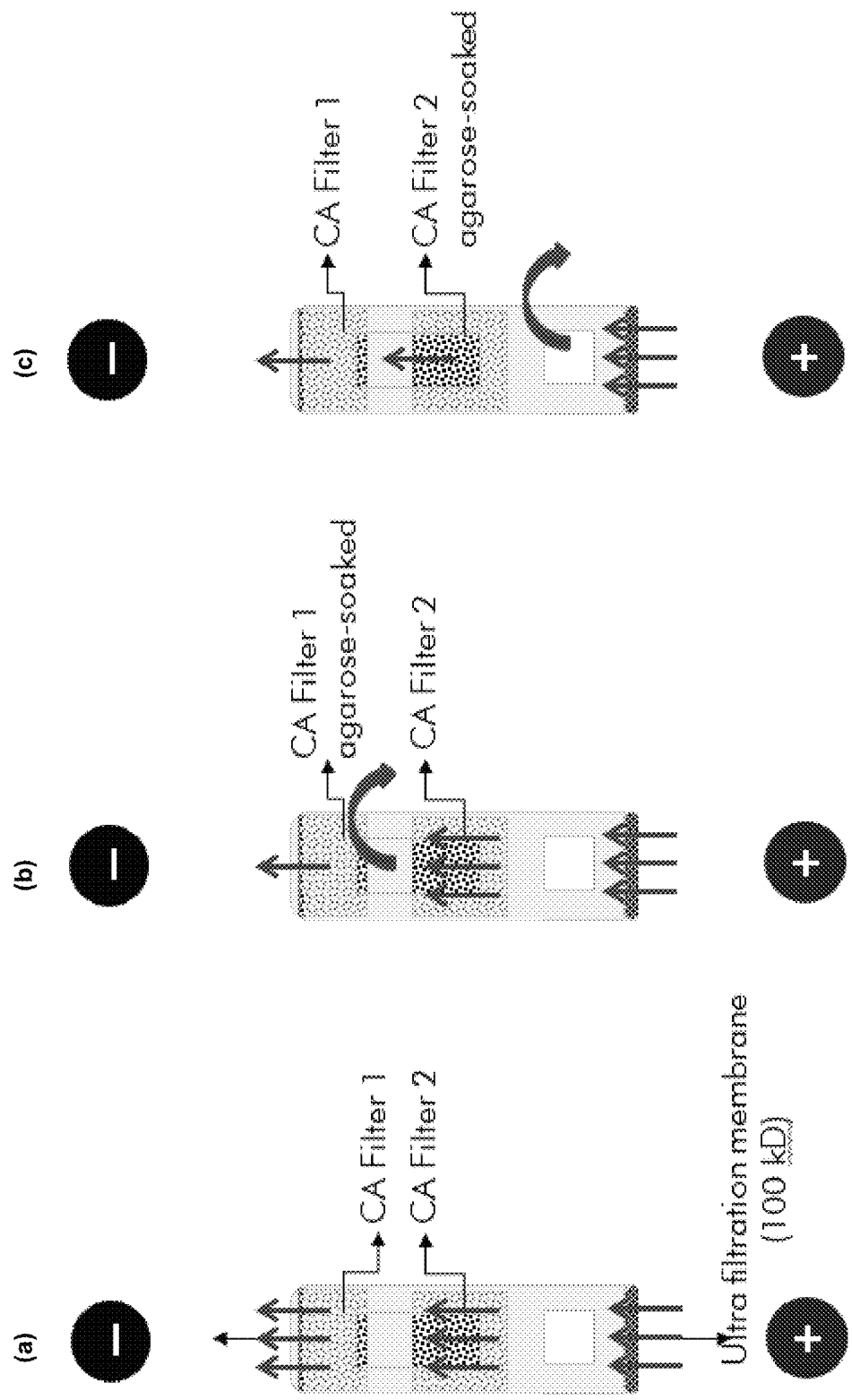

FIG. 18 demonstrates the direction of the induced flow in the passage of the device (see example 9).

Figure 19:
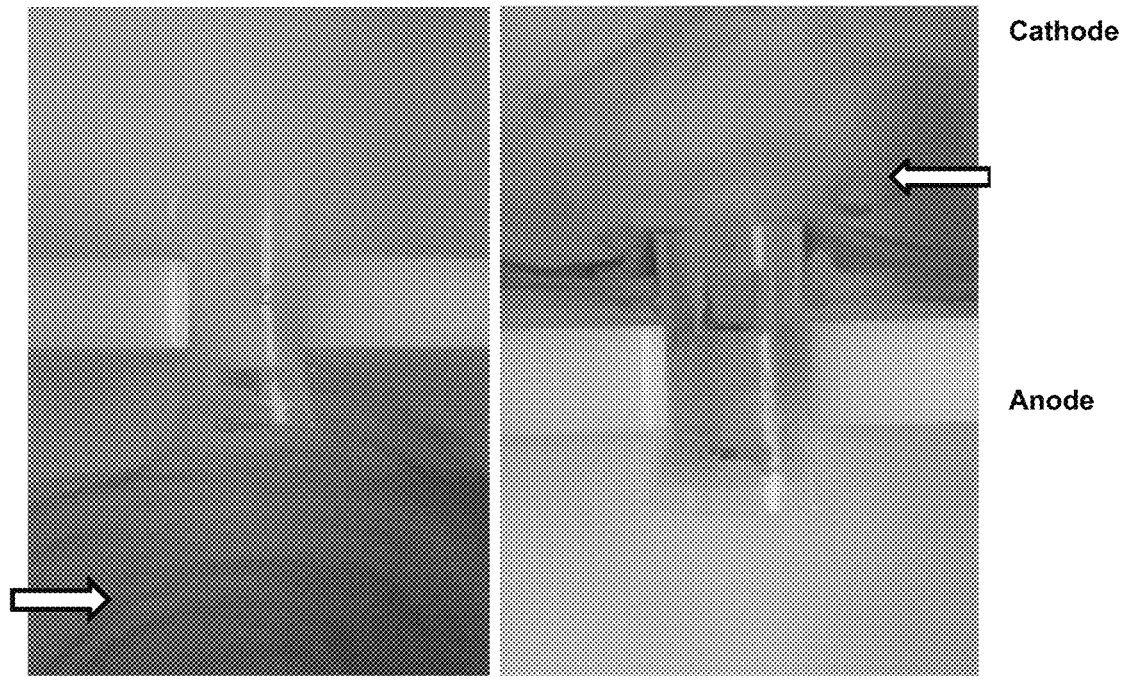

FIG. 19 shows the migration behavior of negatively charged dyes with different charge density (left: BPB; right: XC) at 15V/cm.

Figure 20:
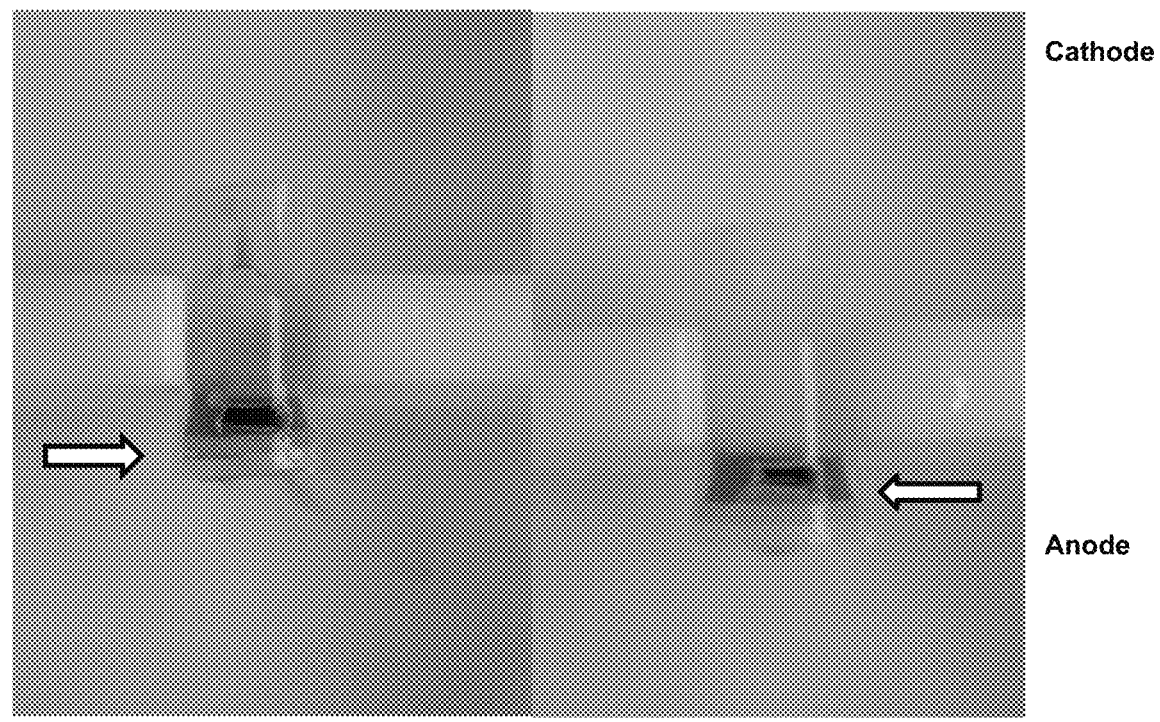

FIG. 20 shows the migration behavior of negatively charged dyes with different charge density (left: BPB; right: XC) at 5V/cm.

Figure 21:
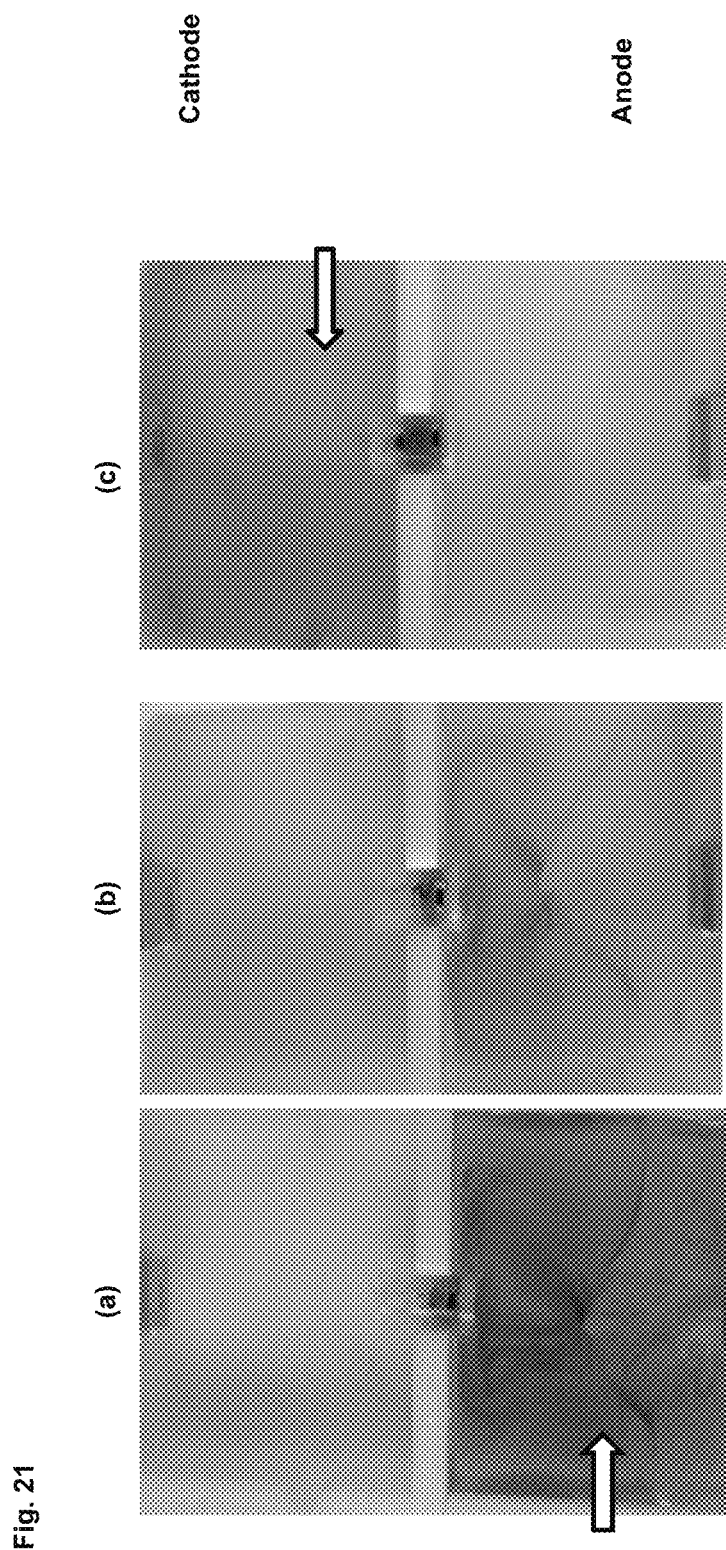

FIG. 21 shows the EOF-behavior of three different 10 kDa-UF membranes. (a): Millipore, RC; (b): Sartorius, CTA; (c): Sartorius, PES.

Figure 22:
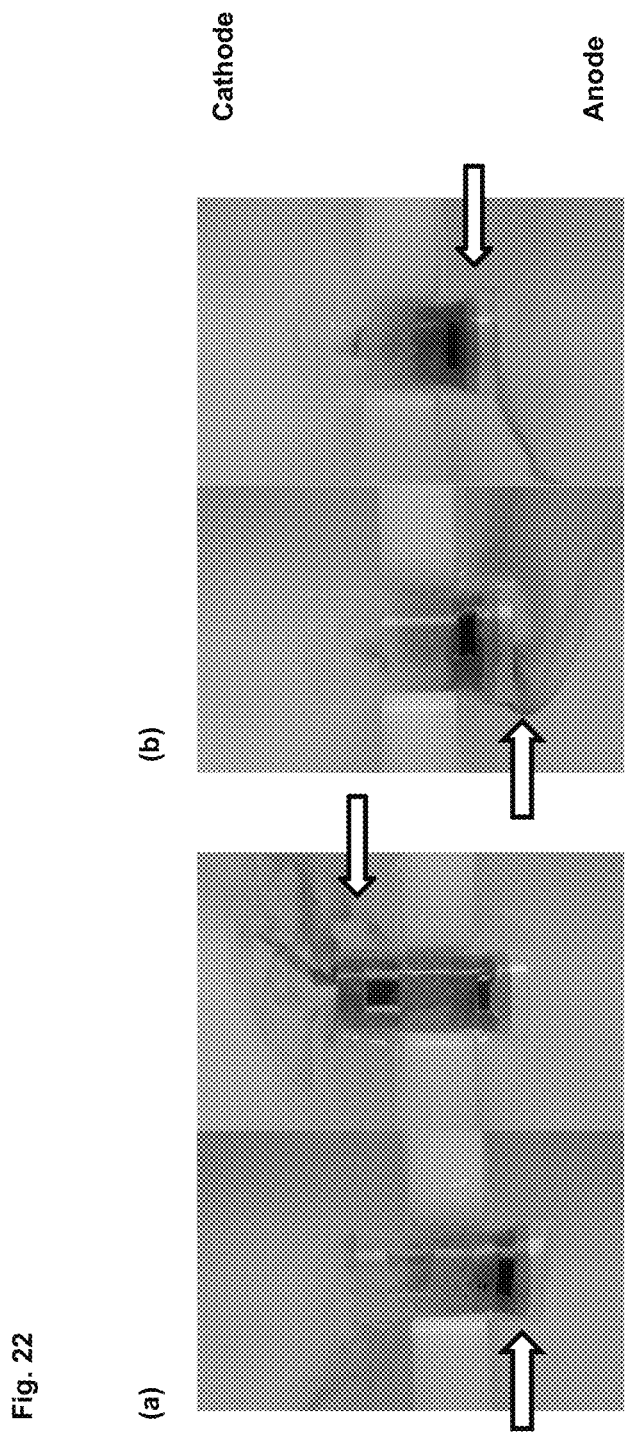

FIG. 22 shows the EOF-behavior of two PES membranes: (a): 100 kDa (left: BPB, right: XC); (b): 300 kDa (left: BPB, right: XC).

Figure 23:
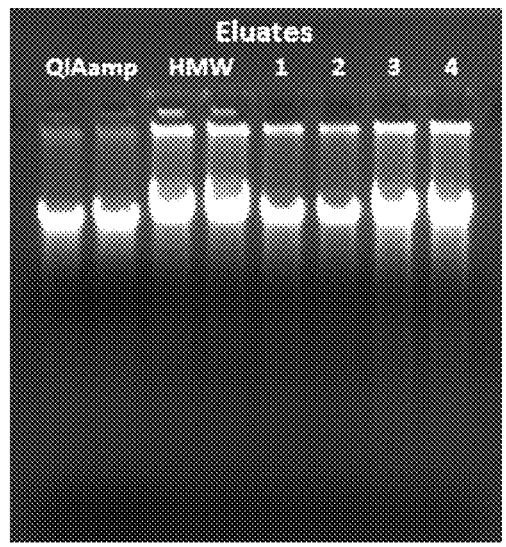

FIG. 23 shows the results of Example 12.

Figure 24:
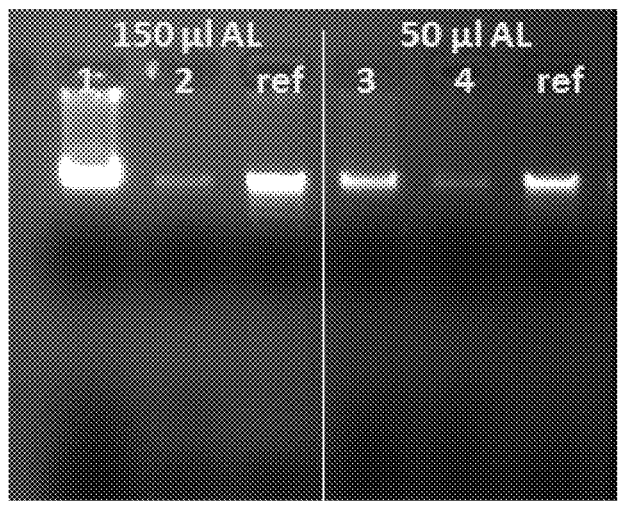

FIG. 24 shows the results of example 13 wherein DNA was isolated with a cartridge according to the invention under two different lysis conditions with two different EOF applied, regulated by the membranes used as closing matrix and collection matrix.

Figure 25:
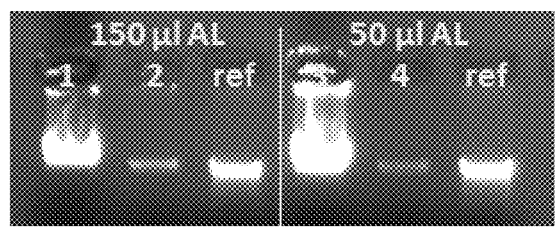

FIG. 25 shows the results using different cartridge set-up.

Figure 26:
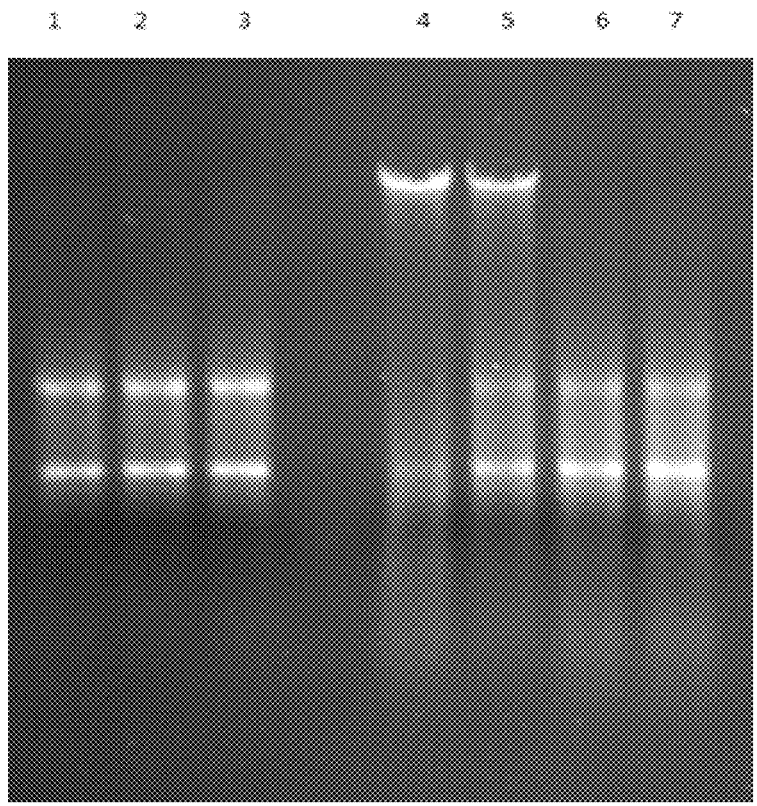

FIG. 26 shows the results of example 15 wherein RNA was purified inter alia with an electrophoresis assisted procedure using RNase inhibitors.

Figure 27:
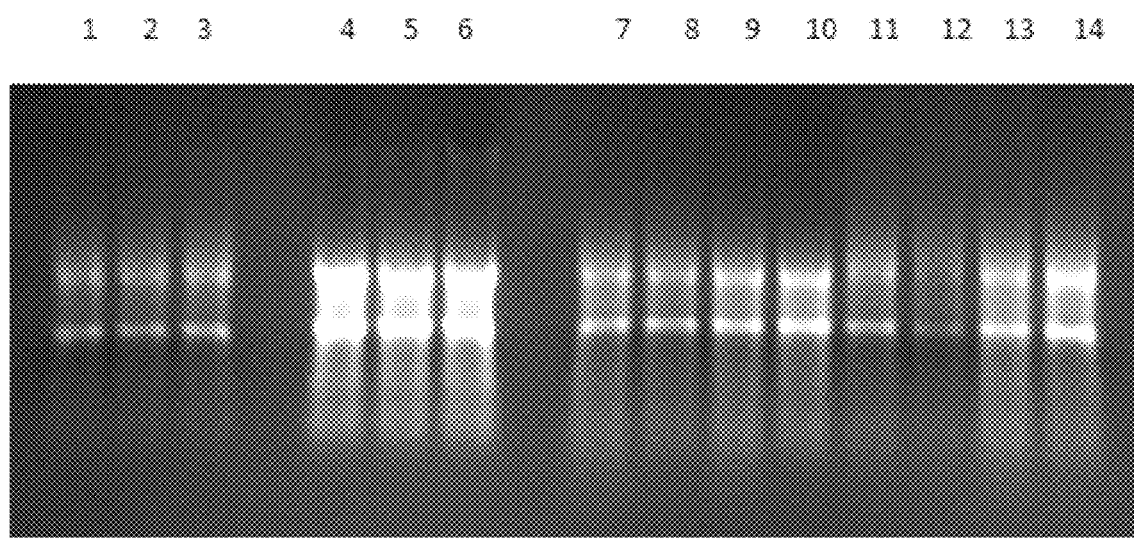

FIG. 27 shows the results of example 16 wherein RNA was purified inter alia using different electrophoresis assisted procedures with delayed elution.

Figure 28:
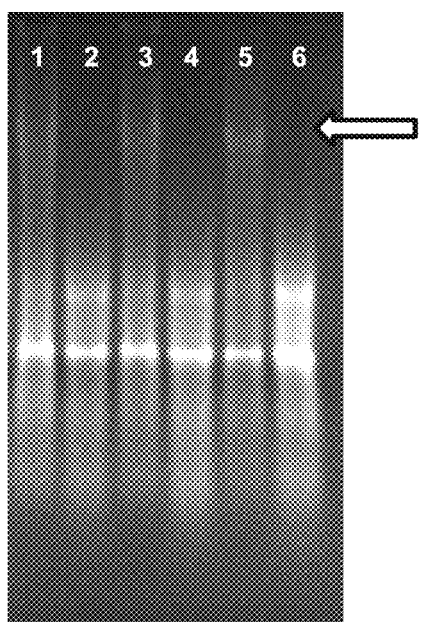

FIG. 28 shows a 1% formaldehyde agarose gel of total RNA preparations with an electrophoresis assisted procedure with delayed elution with and w/o DNaseI digestion (see example 17).

Figure 29:
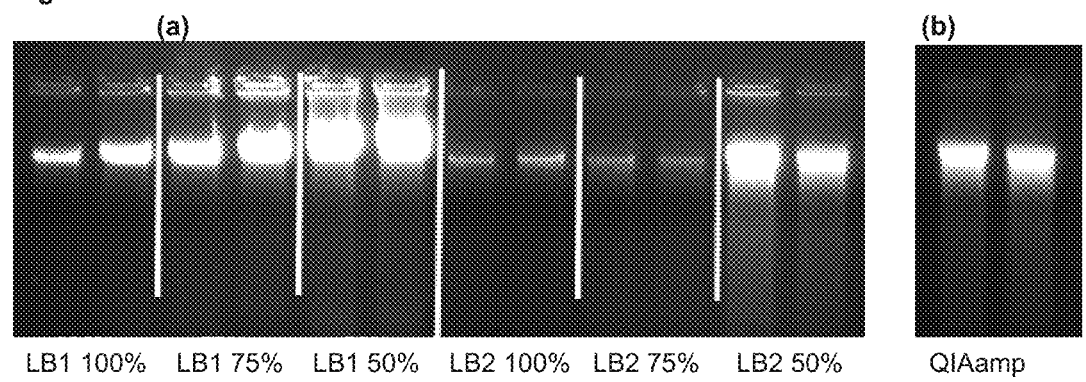

FIG. 29 (a) shows an agarose gel of eluates from buffer LB1 and buffer LB2 dilution series; FIG. 29 (b) shows the QIAamp reference (see example 19).

Figure 30:
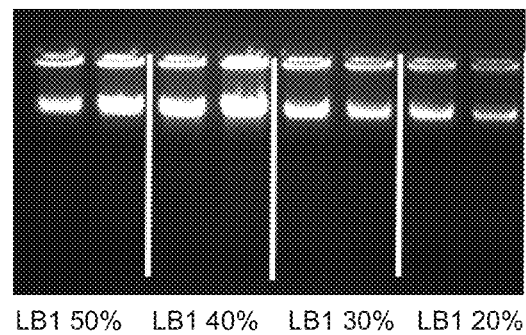

FIG. 30 shows an agarose gel of eluates from a buffer LB1 dilution series (see Example 20).

Figure 31:
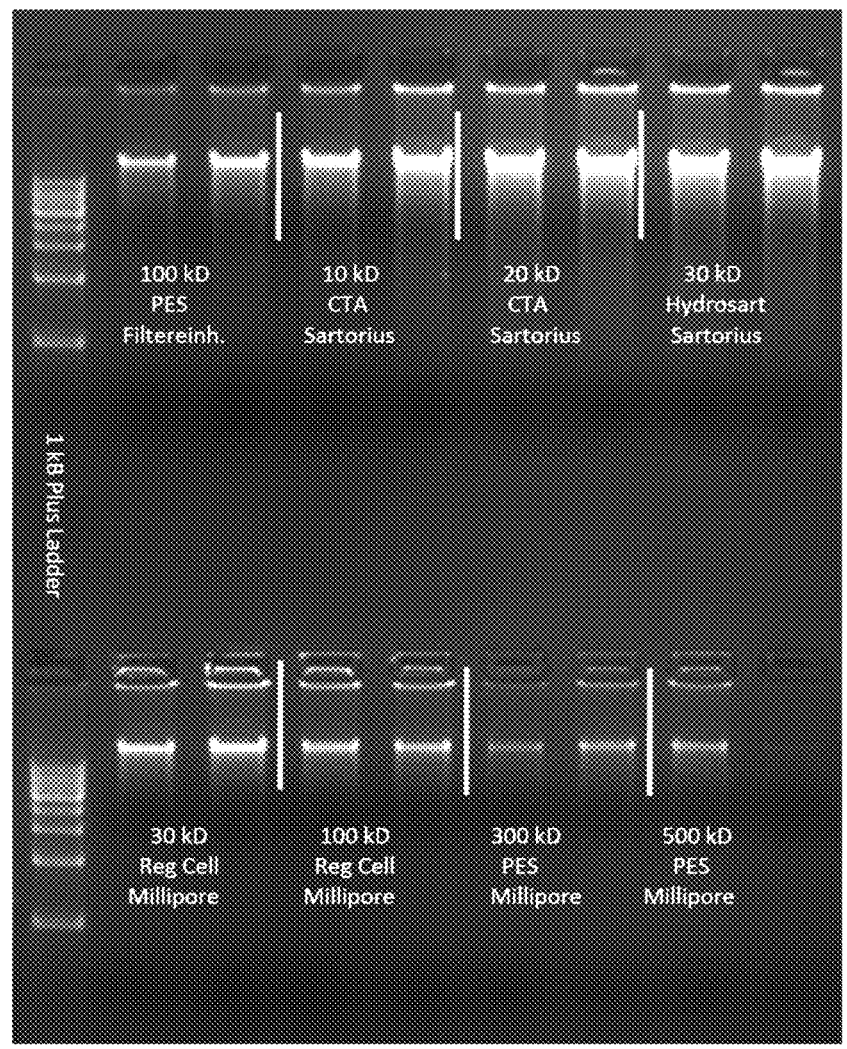

FIG. 31 shows an agarose gel of eluates obtained with flow tube cartridges comprising different collection matrices (see Example 21).

Figure 32:
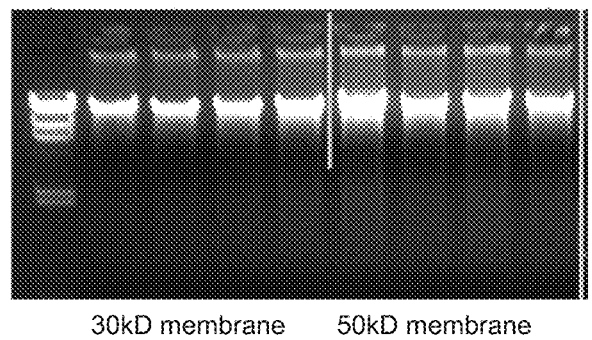

FIG. 32 shows an agarose gel of eluates obtained with flow tube cartridges comprising different collection matrices (see Example 22).

EXAMPLES

The following basic workflow was used in the examples for purifying a target nucleic acid from a sample unless it is indicated otherwise:
- Lyse sample as usual in a lysis buffer comprising a chaotropic salt and bind the target nucleic acids to magnetic particles;
- Place the device according to the invention in an electrophoresis chamber filled with running buffer;
- Transfer the magnetic particles with bound nucleic acid to the loading chamber of the device;
- Apply electric field; nucleic acids move according to their charge in the electric field, pass the separation matrix and are retained by the collection matrix of the device;
- Stop electric field and collect the purified target nucleic acid from the collection chamber of the device. The electric field may be reversed shortly in advance to move the purified target nucleic acid from the collection matrix into the eluate chamber to simplify collection.

ABBREVIATIONS

CTA: cellulose triacetate
CA: cellulose acetae
BPB: bromphenolblue
XC: xylenecyanol
UF: ultrafiltration
RC: regenerated cellulose
PES: polyethersulfone
MOPS: 1×MOPS buffer (20 mM MOPS (N-morpholino) propane sulfonic acid), 50 mM NaCl, 10 mM EDTA, pH 7.0)

Example 1: DNA Separation from High-Salt Solutions

Standard lysis was performed according to the MagAttract HMW DNA Kit from QIAGEN (cat. no. 67563) for isolation of genomic DNA (gDNA) from blood. 200 µl fresh blood (citrate stabilized) was mixed with 20 µl Proteinase K, 4 µl RNase A, and 150 µl Buffer AL (QIAGEN, comprises GuHCl). Then, 15 µl of MagAttract Suspension G were added to the sample followed by 280 µl Buffer MB (QIAGEN, comprising a chaotropic salt) and incubated in a thermomixer for 3 min at 1400 rpm to bind the DNA. Magnetic beads with bound DNA were then transferred to the loading chamber of the device which was pre-filled with running buffer (50 mM Tris pH 8.5). Alternatively, the complete lysate with the released DNA was directly transferred to the loading chamber of the device without prior binding of the DNA to a solid phase.

Cartridge Design:
- Closing matrix: CA filter soaked with 1% agarose
- Separation matrix: CA filter (cigarette filter)
- Collection matrix: PES, 100 kDa (Fa. Sartorius)

An electric field based separation was performed for 40 min at 10V/cm. DNA was collected at the collection matrix. To detach DNA from the collection matrix, the electric field was reversed for 1 min (10V/cm). The purified DNA was withdrawn from the eluate chamber with a pipette.

FIG. 8 shows the results. As can be seen, direct application of the high-salt lysate provided low DNA yields in the tested set up. The small amounts of DNA found in the eluate chamber were rather due to diffusion of the sample during the "no run" stage as monitored by the colored lysate. It is believed that the effect, that DNA does not migrate into and hence does not accumulate in the eluate chamber when a high salt lysate is applied directly to the loading chamber, is caused by excess ions which start to accumulate at the membrane. The effect is triggered by different ionic strengths of the sample and the surrounding running buffer and potentially is accelerated by inner-device flows. In contrast thereto, the embodiment of the invention, wherein the nucleic acids were bound to the beads rendered high amounts of pure DNA in the tested set-up. However, as is demonstrated by example 13 below, nucleic acids can also be directly purified from such lysate using the method of the invention, if a closing matrix is used providing a higher EOF e.g. due to larger pores or different material properties.

Example 2: Isolation of Plasmid DNA

*E. coli* culture: DH5α with pCMVβ; 1 ml; $OD_{600}$=2.7

Lysis was performed according to QIAprep Miniprep protocol (QIAGEN) as follows:
- Resuspend pelleted bacterial cells in 250 µl Buffer P1 and transfer to a micro-centrifuge tube.
- Add 250 µl Buffer P2 and mix thoroughly by inverting the tube gently 4-6 times.
- Add 350 µl Buffer N3 and mix immediately and thoroughly by inverting the tube 4-6 times.
- Centrifuge for 10 min at 13.000 rpm (~17.900×g) in a table-top microcentrifuge.
- Transfer the supernatant from step 4 to a new tube
- Add 15 µl of MagAttract Suspension G to the sample followed by 280 µl Buffer MB.
- Incubate in a thermomixer for 3 min at 1400 rpm to bind the plasmid DNA to the silica particles.

Afterwards, the bound plasmid DNA was purified using electrophoretic separation:
- Magnetic Beads with bound DNA were transferred to the loading chamber of the flooded device (pre-filled with electrophoresis running buffer—50 mM Tris pH 8.5)—that was placed in an electrophoresis chamber.
- Electric field based separation was performed for 40 min at 10 V/cm.
- DNA was collected at the collection matrix.
- To detach the plasmid DNA from the collection matrix the electric field was reversed for 1 min (10V/cm).
- Purified plasmid DNA was withdrawn from the eluate chamber with a pipette.

In this example, different membrane types were used as collection matrix in the cartridge, namely either 100 kDa or 10 kDa from different suppliers (100 kDa PES; 10 kDa RC, 10 kDa PES—from left to right in FIG. 9). Otherwise, the cartridge had the same design as described in example 1.

After the run the magnetic beads were withdrawn from the devices and subjected to a second elution step in order to confirm that the plasmid DNA was completely eluted from the beads. The results shown in FIG. 9 confirm that pure plasmid DNA with a good oc/ccc ratio was isolated. No residual DNA remained on the magnetic particles as was confirmed by the second elution step. Therefore, the electrophoretic field based purification method of the invention achieves good recovery rates.

Example 3: Isolation of gDNA

Standard lysis was performed according to the MagAttract HMW DNA Kit (QIAGEN, cat. no 67563) protocols. The device according to the invention had the structure as shown in FIG. 1. As separation matrix, a cellulose acetate filter was used and a 100 kDa PES collection membrane. A cellulose acetate filter soaked in agarose was used as closing matrix.

a) From E. coli $10^9$ E. coli cells were lysed in 360 µl buffer ATL and split (180 µl each). 20 µl Proteinase K was added, and the solutions incubated for 30 min in a mixer at 56° C. and shaking at 900 rpm. 4 µl RNase A was added to samples. Both samples were mixed and incubated again for 2 min at ambient temperature. 15 µl of MagAttract Suspension G was added to the samples followed by 280 µl Buffer MB and incubated in a thermomixer for 3 min at 1400 rpm. Samples were split again and half of the samples overlaid with mineral oil to improve bead separation (FIG. 10 "with oil"). Magnetic Beads with bound DNA were transferred to the loading chamber of the device that was flooded with the running buffer (50 mM Tris pH 8.5). Electric field based separation was performed for 40 min at 10 V/cm. The purified DNA was then collected at the collection matrix. To improve detachment of the DNA from the matrix the electric field was reversed for 1 min (10V/cm) and the purified DNA was withdrawn from the eluate chamber with a pipette. No DNA degradation or impurities like RNA could be identified using agarose gel analysis of the purified DNA (FIG. 10).

b) From Tissue 10 mg rat kidney tissue was lysed in 220 µl buffer ATL with 40 µl Proteinase K at 56° C. at 1400 rpm. 20 µl Proteinase K were added, and the solution incubated for 30 min on a mixer at 56° C. and shaking over night at 900 rpm. The lysate was centrifuged for 5 min at 18.000×g. 4 µl RNase A were added to the supernatant and incubated for 2 min at ambient temperature. 150 µl Buffer AL were added and mixed by repeated pipetting up and down. 280 µl Buffer MB plus 40 µl MagAttract Suspension G were added and mixed for 2 min at 1400 rpm. The magnetic silica particles with the bound DNA were transferred to the loading chamber of the device and an electric field based separation was performed for 40 min at 10 V/cm in 50 mM Tris pH 8.5. The DNA was collected at the collection matrix. To detach DNA from the matrix the electric field was again reversed for 1 min (10V/cm) and the purified DNA was withdrawn from the eluate chamber with a pipette. No DNA degradation or impurities like RNA could be identified using agarose gel analysis of the purified DNA (FIG. 11).

c) From Blood

200 µl fresh blood (citrate stabilized) was mixed with 20 µl Proteinase K, 4 µl RNase A, and 150 µl Buffer AL. 15 µl of MagAttract Suspension G were added to the sample followed by 280 µl Buffer MB and incubated for 3 min at 1400 rpm. Two samples were prepared and split to overlay half of the samples with mineral oil to improve bead separation (FIG. 12 "with oil"). Magnetic Beads with bound DNA were transferred to the loading chamber of the flooded device. Electric field based separation was performed for 40 min at 10 V/cm in 50 mM Tris pH 8.5. DNA was collected at the collection matrix. To detach DNA from the collection matrix, the electric field was reversed for 1 min (10V/cm). Purified DNA was withdrawn from the eluate chamber with a pipette. No DNA degradation or impurities like RNA could be identified using agarose gel analysis of the purified DNA (FIG. 12).

d) PCR Analysis from Isolated DNA

After isolating the DNA using the method according to the invention the magnetic beads were eluted again with 200 µl Buffer EB for 10 min at 50° C. (second elution). The isolated DNA and DNA from the second elution were analyzed by real-time PCR.

PCR Set-Up:

| Mastermix (73 reactions) | | Program cycler | |
|---|---|---|---|
| 2x QF SG PCR MM | 730 µl | 95° C.; 5 min | |
| S16 Primer 1520/1521 | 146 µl (1 µM final) | 95° C.; 10 sec | 40x |
| H2O | 219 µl | 60° C.; 30 sec | |
| PCR reaction: 15 µl MM + 5 µl Template | | Melt | |

The DNA that was purified using the method of the invention showed no inhibition in the PCR, thereby demonstrating efficient removal/depletion of inhibitors.

Example 4: Separation of Topoisomers

The cartridge used had a silicone tube housing with an inner/outer diameter: 6/10 mm. A cellulose-acetate (CA) filter served at the same time as closing matrix, loading pad and separation matrix. A 100 kD membrane PES (Sartorius, Gottingen, Germany) was used as collection matrix fixed by retainer rings. A collection/eluate chamber was formed between the collection matrix and the CA filter. Two devices were embedded in a 1% agarose gel in buffer TAE and stained with GelStar (Lonza Bioscience) to monitor the DNA after leaving the device. Plasmid pCMVα (7.2 kb) was linearized by digestion with XhoI restriction enzyme (NEB Biolabs). Original and linearized plasmid DNA was prestained with GelStar by incubation in the dark for 15 min. DNA was injected in the CA-filter with a needle and an electric field was applied (4V/cm). DNA migration was monitored with blue light for 110 minutes.

The results are shown in FIGS. 13 and 14. After 20 min both plasmid configurations have reached the collection membrane. After 30 min the linearized DNA is passing through the filter, whereas the supercoiled DNA is retained at the collection membrane. Therefore, the method is suitable to purify DNA according to its topoisomerie and allowed to isolate the desired supercoiled plasmid DNA. After 40 min a small amount of "supercoiled" DNA seems to pass the filter. Subsequent analysis demonstrated that this was attributable to a small amount of non-supercoiled DNA present in the original DNA preparation which is able to migrate through the collection membrane.

Example 5: Isolation of gDNA from Large Volume Samples (Blood)

Typically, in a mini-prep scale an input volume of 200 µl is used because larger sample volumes in combination with a mini-spin column (loading volume 7-800 µl) lead—due to the additional volume of lysis buffer—to multiple loading steps. This makes this protocol cumbersome and time-consuming. Alternatively, the usage of larger spin columns require larger centrifuges and result in more diluted eluates (larger membrane areas) with a higher risk of alcohol contamination (reduced centrifugal force) compared to mini-spin columns. When using magnetic particles, larger sample input volumes require larger amounts of particles which necessarily results in a higher volume of elution buffer to ensure sufficient wetting and resolution of the nucleic acids from the particles. This again leads to more diluted eluates. The present method overcomes these problems, because in essence the same device and (elution) volumes can be used over a very broad range of sample input volumes. In this example, different sample input volumes were used in order to demonstrate a similar performance over different scales using the same set-up. The protocol was performed as follows:

- 200 µl/1000 µl fresh blood (citrate stabilized) was mixed with 20 µl/100 µl Proteinase K, 4 µl/20 µl RNase A, and 150 µl/750 µl Buffer AL (QIAGEN).
- 15 µl/75 µl of MagAttract Suspension G was added to the sample followed by 280 µl/1400 µl Buffer MB and incubated for 3 min at 1400 rpm.
- The magnetic particles with bound DNA were transferred to the loading chamber of the device.
- Electric field based separation was performed for 60 min at 8 V/cm in 50 mM Tris pH 8.5 running buffer.
- DNA was collected at the closing matrix. To detach the purified DNA from the closing matrix the electric field was reversed for 1 min (10V/cm).
- The purified DNA was withdrawn from the eluate chamber with a pipette (total volume each: 100 µl)

The results are shown in FIG. 15 and demonstrate a similar performance over different scales using identical configurations.

Example 6: Collection of Total RNA

To demonstrate that the present method is also suitable for isolating RNA, 10 µg of total RNA was spiked into lysis buffer RLT (QIAGEN, comprises a chaotropic salt) to a total volume of 350 µl. Then, 350 µl of 70% ethanol was added and mixed with 15 µl of MAS G for 3 min at 1400 rpm. Magnetic particles with bound RNA were transferred to the loading chamber of the flooded device. The housing of said device was provided by a silicon tube (inner/outer diameter: 6/10 mm). A 100 kD (Fa. Sartorius, PES) or a 10 kDa (Fa. Millipore, RC) collection membrane was fixed at the front end by retainer rings. As closing matrix, an agarose-soaked cellulose-Acetate (CA) filter was used.

The electric field based separation was performed for 40 min at 10 V/cm in 50 mM Tris pH 8.5 running buffer. The RNA was collected at the collecting membrane and the purified RNA was withdrawn from the eluate chamber with a pipette (total volume each: 200 µl). The results are shown in FIG. 16. As can be seen, the method is suitable to isolate RNA. However, the used set-up was not optimized for RNA and the pH of the running buffer was too high for RNA. A MOPS running buffer pH 7 provides better results.

Example 7: Induced Flow Effects

To avoid leakage or drainage of the target nucleic acid from the device flows within the passage of the device are according to one embodiment minimized and the pressure equalization within the passage is maximized to avoid inner-tube flow effects which are believed to be caused by an EOF that is induced by the collection membrane. As discussed herein, such flows can result in that the loading chamber and/or the collection chamber overflows or runs empty which is detrimental for the separation process and can lead to loss of the target nucleic acid. To minimize such flows within the passage, ultrafiltration (UF) membranes are preferably used at both ends of the device to reduce a liquid transfer into and out of the passage of the device as much as possible. To avoid unwanted inner-tube EOF based flow effects, a filter having macropores in the µm range may be used as separation matrix.

To demonstrate the flow effects within the cartridge, 20 µl of a slightly negative dye was loaded into devices with different settings. Depending on the predominant effect (electro-kinetic force vs. induced flow) the dye will migrate to the anodic (electric force driven) or cathodic side (flow driven). E=10V/cm; Running buffer: 50 mM Tris, pH 8. Using the device of the invention wherein the open endings of the passage are closed by the ultrafiltration membranes, the migration of the slightly negatively charged dye is more or less undisturbed showing no streaming within the tube thus allowing an efficient electro-kinetic separation by charge. It needed about 10 min to observe significant migration according to charge. Little amount of the dye migrated to the cathode as a result of presumably a diffusion effect in combination with a weak induced flow. In case of a strong induced flow, in spite of its negative charge, the dye moves into the opposite direction to the cathode, thus overcoming the electric force. In this configuration with a strong induced flow an electro-kinetic based separation of a molecule having a charge density as the tested dye is not possible.

Example 8: Effects of the Induced Flow

An induced flow that goes in the opposite direction than the electric field, such as in particular an electroosmotic flow, can lead to an unwanted loss of the target molecule during operation of the system, if the charge density of the target molecule is too low to still allow an electro-kinetic separation. To trace the induced flow in the device, the free flow within the device was blocked with agarose. Leakage of buffer and location of leakage indicates unequal liquid flow and blocking points within the device. To demonstrate that a significant liquid flow within a device occurs without appropriate pressure balance two devices were compared one with and one without channels for pressure balance for analysis purposes. The passage of the device comprised an agarose gel, wherein a loading slot was cut out to allow introduction of the sample. The anodic side of the passage was closed by a collection matrix (100 kDa PES UF membrane (Sartorius) and a collection chamber was formed between the agarose gel and the collection membrane. In one cartridge, small pressure balance channels extended through the agarose gel (upper third) to connect the loading slot with the collection chamber. The other cartridge had the same design, however, without pressure balance channels.

~10 µg of plasmid DNA was incubated with GelStar fluorescent dye (Biozym Diagnostic GmbH) for 10 min in the dark. Two devices with a 100 kDa UF-membrane (Sartorius) as collection matrix were embedded in an agarose gel, flooded with TAE buffer. Fluorescent dye labeled plasmid DNAs were applied to the loading cavity. The fluorescent probe fluorescein was additionally applied in the elution cavity to visualize buffer movement independently from the DNA. An electric field was applied (4V/cm) and DNA migration was monitored with blue light. The results presented in FIG. 17 show that without pressure balance channels (left) undirected running buffer flows followed by leakage out of the opening of the elution cavity occurs (in white circle). This is not seen where the separation matrix comprises pressure balance channels (right). In both cases the fluorescein label is passing the membrane driven by the electric field (white rectangle).

Example 9: Source of the Induced Flow

To analyze which and what type of device component contributes to the observed effects of the induced flow (electroosmotic flow) a "flowing reduction barrier" (an agarose soaked cellulose-acetate (CA) filter) was assembled in the device at different positions as shown in FIG. 18. The smaller arrows indicate the direction of the electroosmotic flow. The number of arrows represents the strength of the flow at the respective position. After applying an external electric field, running buffer is flowing into the device and is blocked by the agarose-soaked filter followed by leakage from the opening nearest to the barrier. Leakage is illustrated by the bend arrows in FIG. 18 (b) and (c). In contrast, when there is no barrier as shown in FIG. 18 (a), no leakage was observed.

The example clearly demonstrates the direction of the electroosmotic flow from the anode to the cathode opposed to the electrically driven direction of nucleic acids. This flow is caused by the collection matrix which is located at the anodic end. Therefore, in case a predominantly electro-kinetic force based separation is desired, it is recommendable to reduce this flow effect as good as possible e.g. to avoid loss of sample due to leakage.

However, the induced flow can also be used to assist the purification process as is demonstrated herein, e.g. by allowing the separation of target molecules according to their charge density and/or by flushing out impurities at the cathodic side of the cartridge as will be demonstrated in the following examples. Therefore, by appropriate adjustment or control of the flow that is induced by the collection matrix it is possible to separate a target molecule according to its charge and/or charge density.

Example 10: Different Migration Behavior of Dyes According to their Charge Density Depending on the Electric Field Strength Cartridge Design:
  Collection matrix: 100 kDa membrane, CTA (Sartorius; glossy side inwards)
  Closing matrix: none
  Separation matrix: CA filter (cigarette filter)

The cartridges were loaded with 10 µl of a BPB or a XC solution respectively in 50 mM Tris/Cl, pH 8. At this pH both molecules are negatively charged. The cartridges were placed in an electrophoresis chamber and an electric field was applied for 10 min (electric field strength: 15V/cm). 50 mM Tris/Cl, pH 8 was used as running solution. A flow occurred from the anode to the cathode. The results (see FIG. 19) demonstrate that in spite the fact that both molecules are negatively charged and hence should migrate in the applied electric field along the electric field lines towards the anode (electro-kinetic separation), they showed a different migration behavior depending on their charge density. BPB which has a higher charge density migrates to the anode, while XC, which has a lower charge density than BPB, migrates to the cathode. This difference in the migration behavior of the tested negatively charged molecules is attributable to a flow that is induced in the running buffer that is comprised in the passage and goes into the direction of the cathode. Said flow is believed to originate from an electroosmotic flow that is induced by the collection matrix.

The separation efficiency of the negatively charged molecules can be regulated and thus controlled by the applied electric field which influences the affected electro-kinetic force different to the EOF. The same cartridge set up was used, wherein the electric field strength was, however, 5V/cm. At this lower electric field strength, both negatively charged molecules migrate to the anode and accordingly were separated according to their charge as is shown in FIG. 20 (electro-kinetic based separation). Therefore, the method and cartridge of the invention allows the separation of biomolecules according to their charge and/or charge density in one run by applying appropriate electric field strength.

Example 11: Flow Creation by Different Collection Matrixes

The separation of negatively charged molecules can furthermore be influenced by the choice of the collecting matrix. Different collecting matrixes create different flow strength depending on the pore size and the material of the collection matrix. This can be used to adjust the flow within the passage of the device.

Cartridge Design:
  Collection matrix: 10 kDa ultrafiltration membrane made of (a) regenerated cellulose (Millipore, RC), (b) cellulose triacetate (Sartorius, CTA) or (c) polyethersulfone (Sartorius, PES)
  Closing matrix: none
  Separation matrix: CA filter The cartridges were loaded with 10 µl of a BPB or XC solution in 50 mM Tris/Cl, pH 8. The cartridges were placed in an electrophoresis chamber and an electric field was applied for 10 min (electric field strength: 15V/cm). 50 mM Tris/Cl, pH 8 was used as running solution. The three different ultrafiltration membranes with 10 kDa pore size that were used as collection matrix showed different flow behaviors as is shown in FIG. 21. Whereas with the RC membrane (a) the electro-kinetic separation force is dominating (the negatively charged dye (XC) migrates towards the anode) the flow induced separation of XC is dominating with the PES membrane (c). The CTA membrane (b) showed an intermediate behavior. Therefore, the method and cartridge of the invention allows the separation of biomolecules according to their charge and/or charge density in one run by choosing an appropriate material for the collecting matrix.

In addition to the material of the collection matrix, also the pore size of the collection matrix can be used to influence and hence adjust the flow inside the passage of the cartridge.

Cartridge Design:
  Collection matrix: PES having a pore size of (a) 100 kDa or (b) 300 kDa
  Closing matrix: none
  Separation matrix: CA filter The cartridges were loaded with 10 µl of a BPB or a XC solution respectively in 50 mM Tris/Cl, pH 8. The cartridges were placed in an electrophoresis chamber and an electric field was applied for 10 min (electric field strength: 10V/cm). 50 mM Tris/Cl, pH 8 was used as running solution. At an electric field strength of 10V/cm the membranes show different flow behaviors. With the 100 kDa collection matrix the electro-kinetic force is dominating for the molecule with the higher charge density (BPB) which accordingly, migrates towards the anode (see FIG. 22 (a), left). In contrast, the molecule with the lower charge density (XC) shows migration towards the cathode which is caused by the induced flow within the passage which dominates the electro-kinetic force (FIG. 22 (a), right). With the 300 kDa collection matrix both dyes migrate to the anode indicating that here the electro-kinetic effect is dominant over the flow effect (see FIG. 22 (b)).

Example 12: Isolation of DNA from Whole Blood with Intermediate Bead Binding

In example 12, the following procedures were compared:
QIAamp (QIAGEN, reference)
MagAttract HMW (QIAGEN, reference)
cartridge based approach with dominant electro-kinetic force (cartridge set up A: collection matrix: 10 kDa CTA membrane (Sartorius, glossy side inwards); separation matrix: CA filter; closing matrix: 10 kDa CTA membrane (Sartorius, glossy side outwards);
cartridge based approach with flow assistance to flush out impurities at the cathodic side (cartridge set up B: collection matrix: 10 kDa CTA membrane (Sartorius, glossy side inwards); separation matrix: CA filter; closing matrix: CA filter).

The reference protocols were performed according to the manufacturer's instructions. The cartridge based purification protocols were performed as follows:

A lysis mixture comprising 150 µl lysis buffer AL (QIAGEN), 20 µl Proteinase K, 4 µl RNase A and 200 µl blood was incubated for 10 min at 56° C. to digest the sample and release the DNA. 15 µl magnetic silica particles (MAS G) were added and 280 µl Buffer MB (QIAGEN) to establish the binding mixture which was incubated for 3 min at 1400 rpm on an Eppendorf Thermomixer. After binding, the beads with the bound DNA were transferred in 100 µl 50 mM Tris/Cl, pH 8 and shook for 3 min at 1400 rpm on an Eppendorf Thermomixer to pre-elute the DNA. The suspension was transferred into the cartridge. Each cartridge set up was tested in duplicate (A: 1, 2; B: 2, 3). The cartridges were placed into the electrophoresis chamber which was filled with running buffer. Cartridges 1 and 2 (set-up A) were flooded with running solution, cartridges 3 and 4 (set-up B) are flooded automatically during operation because of the collection matrix which pumps running buffer into the passage. The electric field (10 V/cm) was applied for 40 min and reversed for 1 min to simplify the collection of the purified DNA. 50 mM Tris/Cl, pH 8 was used as running solution. The results are shown in FIG. 23. The electro-kinetic approach (set-up A; 1+2) showed good yields identical to the established QIAamp reference; the flow assisted approach (set-up B; 3+4) gave significant higher yields in the range of the MagAttract HMW reference (see FIG. 23). However, compared to the reference, the method according to the invention achieves these high yields with significant less hands-on activities.

Samples from the loading and eluate chamber were visually inspected for the location of impurities. The obtained eluates were substantially clear for both cartridge set-ups A and B, demonstrating that both approaches render pure eluates. With the cartridge set-up A, the remaining solution in the loading chamber was colored, demonstrating that visible impurities from the sample (blood components) remained in the loading chamber. With the cartridge set-up B, the remaining solution in the loading chamber was also clear, indicating that such impurities were flushed out of the cartridge by the induced flow, which is as described, assumed to be an electroosmotic flow that is caused by the collection matrix.

Example 13: Isolation of DNA from Whole Blood without Intermediate Bead Binding

A lysis mixture comprising either 150 µl or 50 µl lysis buffer AL (QIAGEN), 20 µl Proteinase K, 4 µl RNase A and 200 µl blood was incubated for 10 min at 56° C. to digest the sample and release the DNA.

100 µl lysate were transferred into a flow assisted cartridge comprising a CA filter as closing matrix, a CA filter as separation matrix and different types of collection matrixes. The following collection matrixes and lysis condition set-ups were tested:

| Set up | Lysis buffer | Collection matrix |
|---|---|---|
| 1 | 150 µl AL | 10 kDa membrane CTA |
| 2 | 150 µl AL | 100 kDa membrane PES |
| 3 | 50 µl AL | 10 kDa membrane CTA |
| 4 | 50 µl AL | 100 kDa membrane PES |

The electric field (10 V/cm) was applied for 40 min and reversed for 1 min to simplify the collection of the purified DNA. 50 mM Tris/Cl, pH 8 was used as running solution. A standard QIAamp protocol was used as a reference (ref).

The results (see FIG. 24) demonstrated comparable or higher yields than the QIAamp reference with flow-tubes containing the 10 kDa membrane (samples 1+3, see lanes 1+4). With the 100 kDa PES membrane, the EOF was stronger than the electro-kinetic force under the tested conditions and DNA got lost through the cathodic side of the flow-tube. In addition, the coloration of eluates compared to the lysate was analyzed. The lysate is strongly colored (red/brown). The eluates obtained with the 100 kDa membrane were clear, demonstrating that the strong EOF flushes impurities out of the cartridge. With the 10 kDa membrane the impurities are almost completely removed, so that the eluates were only slightly colored.

The example was also performed with an identical cartridge set up, wherein, however, the separation matrix was omitted. The cartridge thus comprised a closing matrix (CA filter) and a collection matrix (see above). With this cartridge set up, the DNA yields were higher (see FIG. 25), however, the eluates were more strongly colored.

This example demonstrates that the method according to the invention allows the purification of nucleic acids from a lysate obtained from a complex and hence challenging biological sample (blood). There is no necessity to isolate the nucleic acids in advance by binding them to a solid phase such as e.g. particles. This can significantly reduce hands-on time even further. The protocol can be performed with few handling steps, namely lysis of the sample to release the nucleic acids, transfer of the lysate to the cartridge and collection of the eluate after performing the electric field based separation.

Example 14: Electric Field Based RNA Separation Analogous to DNA

Rat kidney tissue (RNAlater stabilized) was lysed according to the RNeasy protocol with buffer RLT and RTLplus (QIAGEN) and 2×15 s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred with a Pick-Pen into the loading chamber of a cartridge.

Cartridge Design:
Collection matrix: 10 kDa RC membrane (Millipore; Cat. No.: PLGC04710)
Separation matrix: CA-filter
Closing matrix: 10 kDa RC membrane (Millipore; Cat. No.: PLGC04710)

The cartridges were placed in an electrophoresis chamber. 1×MOPS was used as running buffer. The electric field (10 V/cm) was applied for 40 min and reversed for 1 min to simplify the collection of the purified RNA. An RNeasy protocol with RTL and RTLplus lysis buffer was used as a reference.

The eluates were analyzed on a 1% formaldehyde agarose gel. The results showed that the RNA was degraded in the eluates obtained from the cartridge based purification process. This loss in RNA is presumably due to the re-activation of RNases (in particular originating from the biological sample) after dilution of the chaotropic lysis buffer in the low-salt running buffer. Therefore, RNases would need to be destroyed during the lysis process, e.g. using proteinase K or other means. Alternative and improved solutions for isolating RNA are described in the following.

Example 15: Electric Field Based RNA Separation Using RNase Inhibitors

Rat kidney tissue (RNAlater stabilized) was lysed according to the RNeasy protocol with buffer RTLplus (QIAGEN) and 2×15 s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred to fresh tubes comprising the buffer with or w/o further additives, as indicated in the subsequent table. The magnetic particles were shaken for 3 min at 1400 rpm in a thermomixer to effectively elute the nucleic acids from the beads. The different suspensions comprising the beads and the eluted nucleic acids were then transferred into the prepared cartridges. The loading chambers were correspondingly pre-loaded with MOPS-buffer w/o or with different RNase inhibitors and with or w/o DNase as indicated.

| Set-up | Buffer and additives | Lane in FIG. 26 |
|---|---|---|
| 1 | 200 µl 1× MOPS | 4 |
| 2 | 180 µl 1× MOPS, 10 µl QIAGEN RNase inhibitor, 10 µl NEB RNase inhibitor | 5 |
| 3 | 180 µl 1× MOPS, 10 µl QIAGEN RNase Inhibitor + 10 µl NEB RNase Inhibitor; +10 µl DNase I solution | 6 |
| 4 | 180 µl 1× MOPS, 10 µl QIAGEN RNase Inhibitor + 10 µl NEB RNase Inhibitor; +10 µl DNase I solution | 7 |

Cartridge Design:
Collection matrix: 10 kDa RC membrane (Millipore; Cat. No.: PLGC04710)
Separation matrix: CA-filter
Closing matrix: CTA, glossy side outwards An RNeasy protocol with RTLplus lysis buffer was used as a reference.

The eluates obtained with the RNeasy references and the different cartridge set-ups were analyzed on a 1% formaldehyde agarose gel (lanes 1 to 3, RNeasy reference (5 µl); lanes 4 to 7 (eluates from set-ups 1 to 4 (20 µl)). The results are shown in FIG. 26. The gel shows for the cartridge based approaches RNA degradation in the eluates wherein no RNase inhibitors were used to protect the RNA (lane 4/set-up 1), DNA contamination in the eluates without DNase I (lanes 4 and 5/set-ups 1 and 2) and only slight degradation of the 28S rRNA in the eluates that were obtained with RNase inhibitors (lanes 5, 6, 7/set-ups 2, 3 and 4). Therefore, including an RNase inhibitor can prevent the degradation of RNA during the electric field based purification process. The additional use of DNase can improve the results.

Example 16: Electric Field Based RNA Separation with Delayed Elution

Rat kidney tissue (RNAlater stabilized) was lysed according to the RNeasy protocol with buffer RTL (QIAGEN) and 2×15 s homogenization with a TissueRaptor. Aliquots of 400 µl lysate were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The loading chambers of 8 cartridges were preloaded with different liquid media and the magnetic silica particles with the bound RNA were then transferred with a Pick-Pen into the loading chamber of a cartridge:

Cartridge Design:
Collection matrix: 10 kDa CTA membrane (Sartorius, Cat-No.: 14539-47-D)
Separation matrix: CA-filter
Closing matrix: glass fiber (GF/B) (cartridges 1 to 4) or 10 kDa CTA (cartridges 5 to 8)

Cartridges 1 and 5:
Loading chamber with buffer RPE (QIAGEN; 80% ethanol)

Cartridges 2 and 6:
Loading chamber with buffer RPE, 10 µl QIAGEN RNase inhibitor, 10 µl NEB RNase Inhibitor Cartridges 3 and 7:
Loading chamber with buffer RPE/water 1: 1 (=40% ethanol in the loading chamber)

Cartridges 4 and 8:
Loading chamber with buffer RPE/water 1: 1 (=40% ethanol in the loading chamber), 10 µl QIAGEN RNase inhibitor, 10 µl NEB RNase inhibitor The cartridges were placed in an electrophoresis chamber. 1×MOPS was used as running buffer. The electric field (10 V/cm) was applied for 40 min and reversed for 20 sec to simplify the collection of the purified RNA. An RNeasy protocol was used as a reference.

The eluates obtained with the RNeasy references and the different cartridge set-ups were analyzed on a 1% formaldehyde agarose gel. FIG. 27 shows the results. Lanes 1-6: RNeasy reference in triplicates, two different amounts of eluate Lanes 7-14: RNA isolated using a cartridge based purification approach as described above (cartridges 1 to 8).

The result demonstrates that cartridge based approaches allowed the isolation of RNA with a good 18 s/28S rRNA ratio which demonstrates the effectiveness of the new approach despite the simplicity of the procedure. Also apparent is the influence of the cartridge configuration on the RNA yield. Thus, by optimizing the combination of matrixes, total RNA yield can be increased.

The comparison of samples with and w/o RNase inhibitors also shows that there is no need for expensive RNase inhibitors to protect the RNA. Instead, it is possible to use a liquid medium which comprises a water-miscible organic solvent such as here 40-80% ethanol. The ethanol comprised in the liquid secures binding of the RNA to the particles when the electric field based separation begins. Thus, the RNA remains initially bound to the particles, while RNases, which are basic proteins with a positive charge, migrate towards the cathode. Upon dilution of the liquid medium in the loading chamber elution of the RNA is initiated. However, the delayed elution approach prevents a substantial contact between active/reactivated RNases and the RNA and hence prevents that the RNA is quickly degraded in the loading chamber. Therefore, the delayed elution approach described herein is highly effective in preserving the integrity of the RNA during preparation. The process is simple and does not rely on expensive substances such as RNase inhibitors. This makes an important contribution to the art.

Example 17: Quality Control of Electric Field Based RNA Separation with Delayed Elution Approx. 120 mg rat kidney tissue (RNAlater stabilized) was lysed in 4.8 ml buffer RLTplus with 240 Reagent DX according to the RNeasy Plus protocol and 2×15 s homogenization with a TissueRaptor. Aliquots of 400 µl lysate (=10 mg tissue) were used for each preparation. 300 µl ethanol was added to 400 µl lysate and 15 µl of magnetic silica particles (MASG, QIAGEN). The binding mixture was incubated for 3 min with 1400 rpm on an Eppendorf Thermomixer to allow binding of the RNA to the beads. The magnetic silica particles with the bound RNA were then transferred with a Pick-Pen into the loading chamber of a cartridge:
Cartridge Design:
  Collection matrix: 10 kDa CTA membrane
  Separation matrix: CA-filter (cigarette filter)
  Closing matrix: glass fiber (GF/B)
  The loading chambers were prefilled with
  Buffer RPE/water 1: 1 (=40% ethanol in the loading chamber)
  40% isopropanol in water or
  40% DMSO in water.

The cartridges were placed in an electrophoresis chamber. 1×MOPS was used as running buffer. The electric field (10 V/cm) was applied for 40 min and reversed for 20 sec to simplify the collection of the purified RNA. An RNeasy protocol with RTLplus lysis buffer was used as a reference. 3 µl of the eluates (cartridge based purification and RNeasy) were used for analysis on a RNA 6000 Nanochip with an Agilent Bioanalyzer according to the handbook. The electropherograms showed a good 28S/18S peak ratio and good RIN values. The additional use of RNase inhibitors showed no improvement (data not shown) demonstrating a sufficient inhibition of RNA-degrading enzyme by the organic solvents during the delayed elution step.

In an extension of this experiment the preparations with 40% of an organic solvent were also done with DNaseI and Buffer RDD (DNase reaction buffer, QIAGEN) also preloaded into the eluate chamber (10 µl DNase I plus 70 µl RDD). Otherwise, the conditions were the same.

The total RNA eluates obtained with the different cartridge set-ups and delayed elution approaches with and w/o DNase digestion were analyzed on a 1% formaldehyde agarose gel. FIG. 28 shows the results. Lane 1: 40% ethanol; Lane 2: 40% ethanol, DNase I; lane 3: 40% isopropanol; lane 4: 40% isopropanol, DNase I; lane 5: 40% DMSO; lane 6: 40% DMSO, DNase I. The arrow indicates DNA contamination in samples w/o DNase I digest.

The results demonstrate that the classical DNA removal by including a DNase digestion step in the protocol can also be applied in the cartridge based workflow and that this can further improve the quality of the RNA.

Example 18: Isolation of Small RNA Using a Collection Matrix Having a Low MWCO

The MWCO of the collection matrix influences the size of the recovered target nucleic acid. This is shown here for small RNA. Approx. 110 mg rat kidney tissue (RNAlater stabilized) was lysed in 4.4 ml buffer RLTplus (with beta-mercaptoethanol) with 22 µl Reagent DX according to the RNeasy Plus protocol and 2×15 s homogenization with a TissueRaptor. Aliquots of 400 µl lysate (=10 mg tissue) were used for each preparation. Each aliquot was contacted with 20 µl proteinase K and 25 µl of magnetic silica particles (MASG, QIAGEN). 300 µl ethanol was added and the binding mixture was incubated for 3 min with 1400 rpm on an Eppendorf Thermomixer to allow binding of the RNA to the beads. The magnetic silica particles with the bound RNA were then separated using a magnet and the supernatant discarded. The magnetic particles with the bound RNA was contacted with 180 µl MOPS+100 DNase 1, 10 µl QIAGEN RNase inhibitor, 10 µl RNase inhibitor NEB and shaked for 3 min at 1400 rpm to elute the nucleic acids from the beads. The suspension comprising the magnetic particles and the eluted target nucleic acids was then transferred into the loading chamber of a cartridge:
Cartridge Design:
  Collection matrix: Millipore Ultracell UF-membrane (RC), either 10 kDa, 5 kDa, 3 kDa and 1 kDa (each set up was tested in duplicate)
  Separation matrix: CA-filter (cigarette filter)
  Closing matrix: glass fiber (GF/B)

The cartridges were placed in an electrophoresis chamber. 1×MOPS was used as running buffer. The electric field (10 V/cm) was applied for 40 min (250V) and reversed for 20 sec to simplify the collection of the purified RNA. 100 ml eluate was collected from the collection chamber. The RNA containing eluate was subjected to a miScript Reverse Transcription and miScript PCR. Analysis of the CT values demonstrated that the recovery of small miRNA was improved when using a collection membrane with a lower cut-off value. The lowest Ct values were achieved with the 1 kDa ultrafiltration membrane, the Ct values rose with increasing MWCO. The difference between the 1 kDa collection membrane and the 10 kDa collection membrane was approx. 3 Cts. The results are summarized in the subsequent table:

| MWCO collection membrane | Ct miScript PCR with miR25 primer assay |
|---|---|
| 10 kDa | 28.98 |
| 5 kDa | 26.98 |
| 3 kDa | 26.39 |
| 1 kDa | 25.83 |

Example 19: Isolation of DNA from Tissue Samples

Two different alkaline lysis buffers were used to lyse 10 mg rat kidney tissue (fresh frozen). Lysis buffer 1 (LB1) comprised SDS and 100 mM sodium chloride (no chaotropic salt). Lysis buffer 2 (LB2) comprised SDS and 600 mM sodium chloride (no chaotropic salt).

The samples were lysed as follows:
a) 180 µl LB1+20 µl Proteinase K (Prot K) at 56° C. 100 µl rpm for approx. 16 h
b) 135 µl LB1+45 µl Wasser+20 µl Prot K at 56° C. 100 µl rpm for approx. 16 h
c) 9 µl µl LB1+90 µl Wasser+20 µl Prot K at 56° C. 100 µl rpm for approx. 16 h
d) 180 µl FTB+20 µl Prot K at 56° C. 1000 rpm for approx. 16 h
e) 135 µl FTB+45 µl Wasser+20 µl Prot K at 56° C. 1000 rpm for approx. 16 h
f) 90 µl FTB+90 µl Wasser+20 µl Prot K at 56° C. 1000 rpm for approx. 16 h 1000 rpm refers to the movement of an Eppendorf thermomixer. The performed dilution of the lysis buffers LB1 and FTB corresponds to 100%, 75%, and 50%. For comparison, the tissue samples were processed using the QIAamp kit (QIAGEN, reference).

Cartridge Design:
Housing: injection molded PE tube
Collection matrix: 10 kDa PES ultrafiltration membrane (Sartorius, glossy side inwards); fixed by retainer ring
Separation matrix: Hydrophilic PE frit (XM-0294) 18-40 µm pore size
Closing matrix: GF/D glass fiber filter; fixed by retainer ring The flow-tube cartridge was placed in an electrophoresis chamber and flooded with running buffer (50 mM Tris buffer pH 8.0). 200 µl lysate was pipetted into the loading chamber. The mixture of the lysate with the running buffer results in dilution of the lysate of approx. 50%. Electric field based separation was performed for 40 mins at 10 V/cm. The DNA was collected at the membrane. To simplify the collection, the electric field was reversed for 20 s to detach DNA from membrane. The purified DNA was withdrawn from the elution chamber with a pipette (approx. 100 µl).

The results are shown in FIG. 29. FIG. 29 (a) demonstrates that the DNA yield is increased with increasing dilution and accordingly decreasing ionic strength in the lysate and thus the mixture of lysate/running buffer when the lysate is loaded into the tube. With the highest dilution, even higher yields were obtained than with the QIAamp reference (see FIG. 29 (b)). Therefore, the DNA yield can be increased by decreasing the ionic strength in the lysate, respectively the lysate/running buffer mixture.

Example 20: Isolation of DNA from Tissue Samples

The lysis procedure from example 19 was repeated with higher lysis buffer LB1 dilutions (50%, 40%, 30% and 20%).

Cartridge Design:
Housing: injection molded PE tube
Collection matrix: 10 kDa PES ultrafiltration membrane (Sartorius, glossy side inwards); fixed by retainer ring
Separation matrix: cigarette filter (2.5 mm length, 6 mm diameter)
Closing matrix: GF/D glass fiber filter; fixed by retainer ring Electrophoresis assisted purification using the cartridge was performed as described in Example 19. The results are shown in FIG. 30. With higher dilutions, an increase in DNA yield was observed until 40%. With higher dilutions the yield decreased again which was probably the result of a reduced lysis capacity. This can be compensated by supporting the lysis of difficult samples (such as tissue samples) by other conventional lysis means that do not significantly increase the ionic strength of the lysate.

Examples 19 and 20 thus further demonstrate that the lysate can be directly processed in the cartridge of the invention and that there is no need to first bind the nucleic acids to a solid phase. High DNA yields can be achieved with an accordingly balanced lysis buffer between lysis capacity and ionic strength.

Example 21: Isolation of DNA from Blood Using Different Collection Matrices

20 µl Proteinase K was mixed with 200 µl blood and 150 µl lysis buffer AL (QIAGEN) and was maintained for 30 min at room temperature to lyse the blood sample. 4 µl RNase was added and the lysate was incubated at room temperature. Then, 280 µl binding buffer MB (QIAGEN) and 15 µl Mag G beads (QIAGEN) were added and agitated 3 min at 1400 rpm at room temperature to bind the DNA to the magnetic silica particles. The beads were transferred with a Pick Pen in 150 µl elution buffer EB (QIAGEN) and agitated for 3 min at 1400 rpm to elute the DNA from the magnetic silica particles.

Cartridge Design
Housing: injection molded PE tube
Collection matrix: The following materials were used as collection matrix; fixed by retainer ring:
  100 kD PES filter unit (flexible, glossy)
  10 kD CTA Sartorius (flexible, glossy)
  20 kD CTA Sartorius (flexible, glossy)
  30 kD Hydrosart Sartorius (rigid)
  100 kD regenerated cellulose Millipore (rigid)
  300 kD PES Millipore (rigid)
  500 kD PES Millipore (rigid)
Separation matrix: cigarette filter (2.5 mm length, 6 mm diameter)
Closing matrix: GF/D glass fiber filter; fixed by retainer ring The different flow-tube cartridges were placed in an electrophoresis chamber and flooded (except for the loading chamber) with running buffer (50 mM Tris buffer, pH 8.5). The pre-eluate comprising the DNA and the particles was transferred into the loading chamber of the cartridges. Electric field based separation in the cartridge was performed for 40 mins at 10 V/cm. The DNA was collected at the membrane. To simplify the collection, the electric field was reversed for 20 s to detach DNA from membrane. The purified DNA was withdrawn from the elution chamber with a pipette (~100 µl).

FIG. 31 shows the results. As can be seen, all tested collection matrices allowed the isolation of DNA. However, the yields were improved with the collection matrices having a MWCO of 100 kD or less.

Example 22: Isolation of DNA from Blood Using Different Collection Matrices

20 µl Proteinase K was mixed with 200 µl blood, 150 µl lysis buffer AL (QIAGEN) and 4 µl RNase and was maintained for 30 min at room temperature to lyse the blood sample. Then, 280 µl ethanol and 15 µl Mag G beads (QIAGEN) were added and agitated 3 min at 1400 rpm at room temperature to bind the DNA to the magnetic silica particles. The beads were transferred with a Pick Pen in 400 µl elution buffer EB (QIAGEN) and agitated for 3 min at 1400 rpm to elute the DNA from the magnetic silica particles.

Cartridge Design

Housing: injection molded PE tube

Collection matrix: The following materials were used as collection matrix; fixed by retainer ring:

30 kD PES membrane 50 kD PES membrane

Separation matrix: Hydrophilic PE frit (XM-0294) 18-40 µm pore size

Closing matrix: GF/D glass fiber filter; fixed by retainer ring

The different flow-tube cartridges were placed using a holder in an electrophoresis chamber (RunOne™, Embitec; distance between the electrodes: 12.5 cm) and flooded (except for the loading chamber) with running buffer (50 mM Tris buffer, pH 8). The pre-eluate comprising the DNA and the particles was transferred into the loading chamber of the cartridges. Electric field based separation in the cartridge was performed for 99 mins at 8 V/cm. The DNA was collected at the membrane. To simplify the collection, the cartridges were reversed for 20 s to detach DNA from membrane. 50 µl purified DNA eluate was withdrawn from the elution chamber with a pipette. 20 µl of the obtained eluate was analysed on an agarose gel. FIG. 32 shows the results; DNA was isolated with good yields. Therefore, the cartridges according to the present invention can be used with different electrophoresis systems as electrophoresis chamber.

The invention claimed is:

1. An electrophoresis assisted method for purifying a charged target molecule, comprising placing the target molecule to be purified into the passage of a device, wherein said passage is closed at one end by a liquid permeable collection matrix;

generating an electric field between a cathode and an anode in a running solution that conducts the electric current to impose a force onto the target molecule comprised in the passage, wherein the collection matrix forms a barrier for the target molecule;

collecting the purified target molecule;

wherein the collection matrix consists of a material selected from silicones, polyamides, optionally nylon, polyamide urea, polyvinylidene fluoride (PVDF), mineral oxides, silicon containing materials, optionally siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein optionally the collection matrix comprises or consists of a material selected from a PES, nylon and PVDF, optionally it consists of PES, and wherein the collection matrix has one or more of the following characteristics i) it is hydrophilic;

ii) it comprises or consists of a charged, polarizable and/or dielectric material, optionally a negatively charged, negatively polarizable and/or dielectric material;

iii) it is capable of inducing a flow in the running solution comprised in the passage of the device;

iii) it is porous;

iv) it is a filter or membrane;

v) it is an ultrafiltration membrane;

vi) it has a MWCO that lies in the range from 1 kDa to 500 kDa; and/or vii) it does not bind the target molecule under the conditions that are used for electrophoretic purification of the target molecule;

wherein the collection matrix induces a flow in the running buffer comprised in the passage that is directed to the cathode and wherein the target molecule is retained in the passage by the applied electric field due to its charge and/or charge density and optionally migrates to the collection matrix and wherein optionally, the induced flow flushes impurities out of the passage; and wherein the flow within the passage is adjusted and/or compensated by the choice of one or more of parameters selected from the group consisting of the collection matrix material or combination of materials, the pore size of the collection matrix material and/or the applied electric field strength.

2. Method according to claim 1, wherein the target molecule is separated from impurities according to its charge and/or its charge density and has one or more of the following characteristics a) it is a negatively charged molecule;

b) it is a biomolecule;

c) it is a nucleic acid;

d) it is DNA;

e) it is RNA.

3. The method according to claim 1, wherein the passage of the device is closed at the other end by a liquid permeable closing matrix and wherein the closing matrix has one or more of the following characteristics:

i) it is hydrophilic;

ii) it is porous;

iii) it is a filter or membrane;

iv) it is an ultrafiltration membrane, a microfiltration membrane or a deep bed filter;

v) it is porous and optionally has a pore size from 0.1 µm to 100 µm;

vi) it has a MWCO that lies in the range from 1 to 500 kDa;

vii) it has a pore size that is larger than the pore size of the collection matrix;

viii) it has a pore size that lies in the same range as the pore size of the collection matrix wherein said range is between 1 kDa and 300 kDa; and/or ix) it comprises or consists of a material selected from silicones, polyamides, optionally nylon, polyamide urea, polyvinylidene fluoride (PVDF), mineral oxides, silicon containing materials, optionally siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamide, wherein optionally the closing matrix comprises or consists of a material selected from polyethersulfone (PES), a mineral oxide, silicon containing materials, optionally siliceous materials, optionally it comprises or consists of a siliceous material, optionally made of silica and/or glass.

4. The method according to claim 3, wherein the device comprises an ultrafiltration membrane as closing matrix and comprises an ultrafiltration membrane as collection matrix and
   (1) wherein the ultrafiltration membranes that are used as closing matrix and as collection matrix have a MWCO in the range of 1 kDa to 300 kDa, wherein the MWCO of the closing matrix and the collection matrix can be the same or may differ from each other; and/or
   (2) wherein the material of the ultrafiltration membranes that are used as closing matrix and as collection matrix is selected from CA, CTA, RC and PES and wherein the material of the closing matrix and the collection matrix can be the same or may differ from each other.

5. The method according to claim 3, wherein the device comprises a porous closing matrix that is made of a siliceous material, optionally silica or glass, and wherein the closing matrix has a pore size that lies in the range of 0.5 μm to 10 μm and wherein the device comprises an ultrafiltration membrane as collection matrix, wherein
   i) the ultrafiltration membrane has a MWCO in a range from 1 kDa to 300 kDa; and/or
   ii) the material of the ultrafiltration membrane is selected from PES and a cellulose material, optionally selected from PES, CA, CTA and RC.

6. The method according to claim 3, wherein the device is a discrete body, optionally a cartridge, that does not comprise electrodes for generating the electric field and wherein the device is at least during the electrophoretic separation step placed into an electrophoresis chamber which comprises the electrodes for generating the electric field and wherein the passage of the device is via the collection matrix and the closing matrix in fluid communication with the electrophoresis chamber and wherein optionally, the device is a hollow tube and the liquid permeable closing matrix is located at one end region of the tube and the collection matrix is located at the other end region of the tube whereby the passage is formed between the closing matrix and the collection matrix and wherein the closing matrix is located in the region of the cathode and the collection matrix is located in the region of the anode.

7. The method according to claim 1, wherein the passage comprises a liquid permeable separation matrix which is characterized by one or more of the following characteristics:
   i) the separation matrix is a filter or membrane;
   ii) the separation matrix extends within the passage of the device over a length of 0.1 mm to 25 mm;
   iii) the separation matrix is porous;
   iv) the separation matrix is porous and has an average pore size that is smaller than the average size of a solid phase that is placed together with the target molecule to be purified into the passage of the device, wherein in case particles are used as solid phase the average pore size of the separation matrix is smaller than the average diameter of the particles;
   v) the separation matrix is hydrophilic;
   vi) the separation matrix comprises or consists of a material selected from cellulose materials, optionally cellulose, regenerated cellulose (RC), cellulose esters, optionally selected from cellulose acetate materials-optionally cellulose acetate, cellulose diacetate and cellulose triacetate and cellulose nitrat, silicones, polyamides, optionally nylon, polyamide urea, polyvinylidene fluoride (PVDF), mineral oxides, silicon containing materials, optionally siliceous materials, silica, glass, silicates, zeolites (aluminosilicates), polysulfones, polyethersulfone (PES), polyamideimide, polycarbonates, ceramics, stainless steel, silver, polyacrylonitrile (PAN), polyethylene (PE), polypropylene (PP), polytetrafluoroethylene (PTFE), polyvinyl chloride (PVC) and polypiperazinamid;
   vii) the separation matrix comprises or consists of a material selected from cellulose materials, PP, PE, nylon or PVDF, optionally it comprises or consists of cellulose acetate or PE and optionally is provided by a hydrophilic PE filter optionally a PE frit; and/or
   viii) the passage is closed by a liquid permeable closing matrix and the liquid permeable separation matrix is placed between the closing matrix and the collection matrix.

8. The method according to claim 1, wherein the passage of the device comprises a liquid permeable closing matrix, a liquid permeable separation matrix and a liquid permeable collection matrix and wherein the target molecule is a nucleic acid which is placed between the liquid permeable closing matrix and the separation matrix, wherein upon application of the electric field the target nucleic acid migrates through the separation matrix and is retained at the collection matrix.

9. The method according to claim 1, wherein the method is for purifying a target nucleic acid from a nucleic acid containing sample and wherein the target nucleic acid to be purified is placed into the passage of the device
   a) as part of a lysate;
   b) bound to a solid phase; or
   c) as part of an eluate, optionally in combination with the solid phase that was used for isolating the target nucleic acid from the sample.

10. The method according to claim 1, having one of more of the following characteristics:
   a) the electric field strength used for generating the electric field is from 1 to 20 V/cm;
   b) the passage has a cross section in the mm to cm range;
   c) the device is a device suitable to be placed in an electrophoresis chamber for use in a method for purifying a charged target molecule by electrophoresis, the device comprising a first end region and a second end region and a passage between the first end region and the second end region wherein the passage is closed at the second end region by the liquid permeable collection matrix; and/or
   d) the device is said device and is a cartridge which does not comprise electrodes for generating an electric field and is placed in an electrophoresis chamber comprising electrodes for generating the electric field.

11. The electrophoresis assisted method according to claim 1, wherein the collection matrix has two or more of the following characteristics
   i) it is hydrophilic;
   ii) it comprises or consists of a charged, polarizable and/or dielectric material, optionally a negatively charged, negatively polarizable and/or dielectric material;
   iii) it is capable of inducing a flow in the running solution comprised in the passage of the device;
   iii) it is porous;
   iv) it is a filter or membrane;
   v) it is an ultrafiltration membrane;
   vi) it has a MWCO that lies in the range from 1 kDa to 500 kDa; and/or vii) it does not bind the target molecule under the conditions that are used for electrophoretic purification of the target molecule.

12. The electrophoresis assisted method according to claim 1, wherein the collection matrix has three or more of the following characteristics
   i) it is hydrophilic;
   ii) it comprises or consists of a charged, polarizable and/or dielectric material, optionally a negatively charged, negatively polarizable and/or dielectric material;
   iii) it is capable of inducing a flow in the running solution comprised in the passage of the device;
   iii) it is porous;
   iv) it is a filter or membrane;
   v) it is an ultrafiltration membrane;
   vi) it has a MWCO that lies in the range from 1 kDa to 500 kDa; and/or
   vii) it does not bind the target molecule under the conditions that are used for electrophoretic purification of the target molecule.

* * * * *